US006864060B1

(12) United States Patent
Fowlkes et al.

(10) Patent No.: US 6,864,060 B1
(45) Date of Patent: Mar. 8, 2005

(54) YEAST CELLS EXPRESSING MODIFIED G PROTEINS AND METHODS OF USE THEREFOR

(75) Inventors: Dana M. Fowlkes, Chapel Hill, NC (US); James R. Broach, Princeton, NJ (US); John P. Manfredi, Ossining, NY (US); Jeremy I. Paul, Nyack, NY (US); Joshua Trueheart, South Nyack, NY (US); Christine A. Klein, Ossining, NY (US); Andrew J. M. Murphy, Montclair, NJ (US)

(73) Assignee: Cadus Technologies, Inc., New York, NY (US)

(*) Notice: Subject to any disclaimer, the term of this patent is extended or adjusted under 35 U.S.C. 154(b) by 0 days.

(21) Appl. No.: 08/946,298

(22) Filed: Oct. 7, 1997

Related U.S. Application Data

(63) Continuation-in-part of application No. 08/689,172, filed on Aug. 6, 1996, now abandoned, which is a continuation-in-part of application No. 08/582,333, filed on Jan. 17, 1996, now Pat. No. 6,255,059, which is a continuation-in-part of application No. 08/463,181, filed on Jun. 5, 1995, now abandoned, which is a continuation-in-part of application No. 08/322,137, filed on Oct. 13, 1994, now Pat. No. 6,100,042, which is a continuation-in-part of application No. 08/309,313, filed on Sep. 20, 1994, now abandoned, which is a continuation-in-part of application No. 08/190,328, filed on Jan. 31, 1994, now abandoned, which is a continuation-in-part of application No. 08/041,431, filed on Mar. 31, 1993, now abandoned.

(51) Int. Cl.$^7$ .................. G01N 33/569; G12N 15/81
(52) U.S. Cl. .................. 435/7.1; 435/69.1; 435/254.2; 435/320.1
(58) Field of Search .................. 435/7.1, 69.1, 435/254.2, 320.1

(56) References Cited

U.S. PATENT DOCUMENTS

| | | |
|---|---|---|
| 4,418,149 A | 11/1983 | Ptashne et al. |
| 4,833,080 A | 5/1989 | Brent et al. |
| 5,096,815 A | 3/1992 | Ladner et al. |
| 5,283,173 A | 2/1994 | Fields et al. |
| 5,284,746 A | 2/1994 | Sledziewski et al. |
| 5,401,629 A | 3/1995 | Harpold et al. |
| 5,436,128 A | 7/1995 | Harpold et al. |
| 5,468,614 A | 11/1995 | Fields et al. |
| 5,482,835 A | 1/1996 | King et al. ............ 435/6 |
| 5,573,944 A | 11/1996 | Kirschner et al. |
| 5,580,736 A | 12/1996 | Brent et al. |
| 5,691,188 A | 11/1997 | Pausch et al. ............ 435/254 |
| 5,739,029 A | 4/1998 | King et al. |
| 5,789,184 A | 8/1998 | Fowlkes et al. |
| 6,100,042 A | 8/2000 | Fowlkes et al. |
| 4,948,874 A1 | 8/2004 | Kronvall et al. |

FOREIGN PATENT DOCUMENTS

| | | |
|---|---|---|
| EP | 568925 | 4/1992 |
| EP | 0344024 B1 | 8/1996 |
| WO | WO 8810308 | 12/1988 |
| WO | WO 9112273 | 8/1991 |
| WO | WO 92/05244 | 4/1992 |
| WO | WO 92/08740 | 5/1992 |
| WO | WO 93/10230 | 5/1993 |
| WO | WO 94/23025 | 10/1994 |
| WO | WO 95/30012 | 11/1995 |
| WO | WO 97/11159 | 3/1997 |
| WO | WO 98/13513 | 4/1998 |

OTHER PUBLICATIONS

Watkson and Arkinstall . The G–Protein linked receptor facts book. Academic Press, London p. 5, 1994.*
Itoh et al, Molecular cloning of five GTP–binding protein cDNA species from rat olfactory bulb. J. of Biol. Chem. 262:14241–14249, 1987.*
Holmer et al. Tissue and species specific experssion of inhibitory guanine nucleoteid binding proteins. Circulation Research 65: 1136–1140, 1989.*
Quan et al. The Drosophila gene encoding the alpha subunit of stimulatory G protein is preferentially expressed in the nervous system. PNAS USA 83: 4621–4325, 1989.*
Quan et al. Two forms of Drosophila melanogaster Gs alpha are produced by alternate splicing involving unusual splicte sites. Mol. Cell Biol. 10:910–917, 1990.*
Dietzal et al. The yeast SCG1 gene: A G alpha like protein implicated in the a– and alpha–factor response pathway. Cell 50: 1001–1010, 1987.*
Sander, Peter, et al., "Expression of the Human $D_{2s}$ Dopamine Receptor in the Yeasts Saccharomyces Cerevisiae and Schizosaccharomyces Pombe: a Comparative Study", FEBS Letters, 344, pp. 41–46, (1994).
Talmont, Franck, et al., "Expression and Pharmacological Characterization of the Human $\mu$–opioid Receptor in the Methylotrophic Yeast Pichia Pastoris", FEBS Letters 394, pp. 268–272, (1996).
Tate, Christopher, et al., "Heterologous Expression of G–Protein–Coupled Receptors", TibTech, vol. 14, (1996).

(List continued on next page.)

Primary Examiner—Bennett Celsa
(74) Attorney, Agent, or Firm—Peter C. Lauro, Esq.; Edwards & Angell, LLP

(57) ABSTRACT

The present invention pertains to novel yeast cells which are useful for the expression of heterologous G protein coupled receptors. The yeast cells of the present invention can be used in screening assays which can be used to screen for modulators of G protein coupled receptors. Specifically, the invention provides novel yeast cells which express a heterologous G protein coupled receptor and mutant and/or chimeric G protein subunit molecules which serve to functionally integrate the heterologous into the pheromone signaling pathway of the yeast cell. The invention also provides for the expression of heterologous G protein coupled receptors which are functionally integrated into the yeast cell membrane using a yeast $\alpha$ factor leader sequence. Drug discovery assays using the subject yeast cells are also provided.

4 Claims, 2 Drawing Sheets

OTHER PUBLICATIONS

Weiss, H. Markus, et al., "Expression of Functional Mouse 5-HT$_{5A}$ Serotonin Receptor In The Methylotrophic Yeast Pichia Pastoris: Pharmacological Characterization and Localization", FEBS Letters 377, pp. 451–456, (1995).

Whiteway, Malcolm, et al., "Genetic Identification of Residues Involved in Association of α and β G–Protein Subunits", Molecular and Cellular Biology, vol. 14, No. 5, pp. 3223–3229, (1994); and.

Whiteway, Malcolm, et al., "Mutagenesis of Ste18, a Putative Gγ Subunit in the Saccharomyces Cerevisiae Pheromone Response Pathway", Biochem. Cell. Biol., vol. 70, pp. 1232–1237, (1992).

Arkinstall, Steve, et al., "Co–Expression of the Neurokinin NK2 Receptor and G–Protein Components in the Fission Yeast Schizosaccharomyces Pombe", FEBS Letters 375, pp. 183–187, (1995).

Coria, Roberto, et al., "Separate Roles for N– and C–Termini of the STE4 (β) Subunit of the Saccharomyces Cerevisiae G Protein in the Meditation of the Growth Arrest. Lack of Growth–Arresting Activity of Mammalian βγ Complexes", Yeast, vol. 12, pp. 41–51 (1996).

Coria, Roberto, et al., "STE2/SCG1–Dependent Inhibition of STE4–induced Growth Arrest By Mutant STE4$^{\Delta C6}$ In the Yeast Pheromone Response Pathway", FEBS Letters 367, pp. 122–126, (1995).

Dietzel, et al., "The Yeast SCG1 Gene: A Gα–like Protein Implicated in the a– and α–Factor Response Pathway", Cell, vol. 50, pp. 1001–1010, (1987).

Huang, Hao–jen, et al., "Functional Expression of RAT M5 Muscarinic Acetylcholine Receptor In Yeast", Biochemical and Biophysical Research Communications, vol. 182, No. 3, pp. 1180–1186, (1992).

Kajkowski, Eileen, et al., "Investigation of Growth Hormone Releasing Hormone Receptor Structure and Activity Using Yeast Expression Technologies", J. Of Receptor & Signal Transduction Research, 17(1–3), pp. 293–303, (1997).

Kang, Yoon–Se, et al., "Effects of Expression of Mammalian Gα and Hybrid Mammalian–Yeast Gα Proteins on the Yeast Pheromone Response Signal Tranduction Pathway", Molecular and Cellular Biology, pp. 2582–2590 (1990).

Payette, Paul, et al., "Expression and Pharmacological Characterization of Human M12 Muscarinic Receptor in Saccharomyces Cervisiae", FEBS, vol. 266, No. 1,2, pp. 21–25, (1990).

Murphy, Philip, et al., "Functional Expression of the Human Formyl Peptide Receptor in Xenopus Oocytes Requires a Complementary Human Factor", The Journal of Biological Chemistry, vol. 266, No. 19, pp. 12560–12567, (1991).

King, Klim, et al., "Control of Yeast Mating Signal Transduction by a Mammalian β$_2$– Adrenergic Receptor and G$_s$ α Subunit", Science, vol. 250, pp. 121–123, (1990).

Leberer, Ekkehard, et al., "Dominant–negative Mutants of a Yeast G–Protein β Subunit Identify Two Functional Regions Involved in Pheromone Signalling", The EMBO Journal, vol. 11, No. 13, pp. 4805–4813, (1992).

Price, Laura, et al., "Functional Coupling of a Mammalian Somatostatin Receptor to the Yeast Pheromone Response Pathway", Molecular and Cellular Biology, vol. 15, No. 11, pp. 6188–6195, (1995).

Russell, Marijane, et al., "G Protein Amino–Terminal α$_{i2}$/α$_s$ Chimeras Reveal Amino Acids Important in Regulating α$_s$ Activity", Molecular Pharmacology, vol. 44, pp. 255–263 (1993).

Kang, Y.-S. et al., "Effects of expression of mammalian galpha and hybrid mammalian yeast galpha proteins on the yeast pheromones response signal transduction pathway," J. Mol. Biol., 10(6):2582–2590 (1990).

King, K. et al., "Control of yeast mating signal transduction by a mammalian beta2–adrenergic receptor and Gs alpha subunit," Science, 250:121–123 (1990).

Manfredi, J. et al., "Autocrine stimulation of yeast through human G–coupled receptors," J. Cell. Biochem., 18B:224 (1994).

U.S. Appl. No. 09/258,600, filed Feb. 1999, Fowlkes et al.
U.S. Appl. No. 09/286,166, filed Apr. 1999, Fowlkes et al.
U.S. Appl. No. 09/581,861, filed Mar. 2001, Broach et al.
U.S. Appl. No. 09/747,774, filed Dec. 2000, Klein et al.
U.S. Appl. No. 10/263,341, filed Oct. 2002, Fowlkes et al.
U.S. Appl. No. 10/277,607, filed Oct. 2002, Klein et al.
U.S. Appl. No. 10/752,478, filed Jan. 2004, Klein et al.

Akada, R. et al. "Genetic Relationships Between the G Protein βγ Complex, Ste5p, Ste20p and Cdc42p: Investigation of Effector Roles in the Yeast Pheromone Response Pathway," Genetics 143: 103–117 (1996).

Alison, Malcolm R. et al. "Growth factors and growth factor receptors," Brit. J. of Hosp. Med. 49(11):774–88 (1993).

Altieri, Dario C. "Proteases and protease receptors in modulation of leukocyte effector functions," J. of Leukocyte Biol. 58: 120–27 (1995).

Artemyev, Nikolai O. et al. "Sites of Interaction between Rod G–Protein α–Subunit and cGMP–phosphodiesterase γ–Subunit," J. Biol. Chem. 267(35):25067–72 (1992).

Awramik, S. M. "New fossil finds in old rocks," Nature 319:446–47 (1986).

Belka, C. et al. "The role of tyrosine kinases and their substrates in signal transmission of hematopoietic growth factors: a short review," Leukemia 9:754–61 (1995).

Bender, Alan and Sprague, George F. Jr. "Pheromones and Pheromone Receptors Are the Primary Determinants of Mating Specificity in the Yeast Saccharomyces cerevisiae," Genetics 121:463–76 (1989).

Birnbaumer, Lutz "Transduction of receptor signal into modulation of effector activity by G proteins: the first 20 years or so. . . " FASEB Journal 4:3178–88 (1990).

Blinder, Dmitry et al. "Constitutive Mutants in the Yeast Pheromone Response: Ordered function of the Gene Products," Cell 56:479–486 (1989).

Brill, Julie A. et al. "A Role for Autophosphorylation Revealed by Activated Alleles of FUS3, the Yeast MAP Kinase Homolog," Molecular Biology of the Cell 5:297–312 (1994).

Brugarolas, James et al. "Radiation–induced cell cycle arrest compromised by p21 deficiency," Nature 377:522–57 (1995).

Burack, W. Richard et al. "The Activating Dual Phosphorylation of MAPK by MEK Is Nonprocessive," Biochemistry 36(20):5929–5933 (1997).

Cavallini, Bruno et al. "A yeast activity can substitute for the HeLa Cell TATA box factor," Nature 334:77–80 (1988).

Chambers, D. A. et al. "Neuroimmune Modulation: Signal Tranduction and Catecholamines," Neurochem. Int. 22(2):95–110 (1993).

Chan, Russell K. and Otte, Carol A. "Isolation and Genetic Analysis of *Saccharomyces cerevisiae* Mutants Supersensitive to G1 Arrest by a Factor and α Factor," *Molecular and Cellular Biol.* 2(1): 11–20 (1982).

Chang, Fred and Herskowitz, Ira "Identification of a Gene Necessary for Cell Cycle Arrest by a Negative Growth Factor of Yeast: FAR1 is an Inhibitor of a G1 Cyclin, CLN2," *Cell* 63:999–1011 (1990).

Chien, Cheng–Ting, et al. "The two–hybrid system: A method to identify and clone genes for proteins that interact with a protein of interest," *Proc. Natl. Acad. Sci. USA* 88:9578–82 (1991).

Clark, Karen L. et al. "Interactions among the Subunits of the G–protein Involved in *Saccharomyces cerevisiae* Mating, " *Molecular and Cellular Biol.* 13(1):1–8 (1993).

Cole, Gary M. et al. "Stoichiometry of G Protein Subunits Affects the *Saccharomyces cerevisiae* Mating Pheromone Signal Transduction Pathway," *Molecular and Cellular Biology* 10(2):510–517 (1990).

Coleman, David E. et al. "Structures of Active Conformation of $G_{i\alpha1}$ and the Mechanism of GTP Hydrolysis," *Science* 265:1405–12 (1994).

Conklin, Bruce R. et al. "Substitution of three amino acids switches receptor specificity of $G_{q\alpha}$ to that of $G_{i\alpha}$, " *Nature* 363:274–76 (1993).

Cwirla, Steven E. et al. "Peptides on phage: A vast library of peptides for identifying ligands," *Proc. Natl. Acad. Sci. USA* 87:6378–82 (1990).

Devlin, James J. et al. "Random Peptide Libraries: A Source of Specific Protein Binding Molecules," *Science* 249:404–6 (1990).

Dmochowska, Aleksandra et al. "Yeast KEX1 Gene Encodes a Putative Protease with a Carboxypeptidase B–like Function Involved in Killer Toxin and α–Factor Precursor Processing, " *Cell* 50:573–84 (1987).

Dolan, J. W. et al. "Overproduction of the yeast STE12 protein leads to constitutive transcriptional induction," *Genes & Development* 4(4):492–502 (1990).

Dubois, Patrice M. et al. "Role of the transmembrane and cytoplasmic domains of surface IgM in endocytosis and signal transduction, " *Eur. J. Immunol.* 22:851–57 (1992).

Erickson, Deborah "Intercepted Messages: New biotectnology drugs target intracellular communication," *Scientific American* 267(5):122–23 (1992).

Etienne, Gilles et al. "A Screening Method for Antifungal Substances Using *Saccharomyces cerevisiae* Strains Resistant to Polyene Macrolides," *J. of Antibiotics* 43(2):199–206 (1990).

Fasullo, Michael T. and Davis, Ronald W. "Direction of Chromosome Rearrangements in *Saccharomyces cerevisiae* by Use of his3 Recombination Substrates," *Molecular and Cellular Biol.* 8(10):4370–80 (1988).

Ferrell, James E. Jr. et al. "The Biochemical Basis of an All–or–None Cell Fate Switch in Xenopus Oocytes," *Science* 280:895–898 (1998).

Ferrell, James E. Jr. "Tripping the switch fantastic: how a protein kinase cascade can convert graded inputs into switch–like outputs," *Trends In Biochem. Sci.* 21(12):460–6(1996).

Fields, Stanley and Song Ok–kyu "A novel genetic system to detect protein–protein interactions," *Nature* 340:245–46 (1989).

Franke, Arthur E. et al. "Human C5a Anaphylatoxin: Gene Synthesis, Expression, and Recovery of Biologically Active Material from *Escherichia coli*, " *Methods in Enzymology* 162:653–68 (1988).

Funaro, Ana et al. "Human CD38 is associated to distinct molecules which mediate transmembrane signaling in different lineages," *Eur. J. Immunol.* 23:2407–11 (1993).

Gallego, Carme et al. "Myristoylation of the $G_{\alpha i2}$ polypeptide, a G protein a subunit, is required for its signaling and transformation functions," *Proc. Natl. Acad. Sci. USA* 89:9695–99 (1992).

Garritsen, Anja et al. "The N–Terminal coiled–coil domain of β is essential for γ association: A Model for G–Protein βγ subunit interaction," *Proc. Natl. Acad. Sci. USA* 90:7706–10 (1993).

Gerard, Norma P. and Gerard, Craig "Construction and Expression of a Novel Recombinant Anaphylatoxin, C5a–N19, a Probe for the Human C5a Receptor," *Biochemistry* 29(39):9274–81 (1990).

Gordon, J. "B–cell signaling via the C–type lectins CD23 and CD72," *Immunology Today* 15(9):411–17 (1994).

Graf, Rolf et al. "A Truncated Recombinant α Subunit of $G_{i3}$ with a Reduced Affinity for βγ Dimers and Altered Guanosine 5'–3–O–(Thio)triphosphate Binding," *J. of Biol. Chem.* 267(34):24307–14 (1992).

Gros, Philippe et al. "Mammalian Multidrug Resistence Gene: Complete cDNA Sequence Indicates Strong Homology to Bacterial Transport Proteins," *Cell* 47:371–80 (1986).

Gyuris, Jenö et al. "Cdi1, A Human G1 and S Phase Protein Phosphatase That Associates with Cdk2,"*Cell* 75:791–803 (1993).

Hagen, David C. et al. "Evidence the yeast *STE3* gene encodes a receptor for the peptide pheromone a factor: Gene sequence and implications for the structure of the presumed receptor," *Proc. Natl. Acad. Sci. USA.* 83: 1418–22 (1986).

Hall, Marcia et al. "Evidence for different modes of action of cyclin–dependent kinase inhibitors: p15 and p16 bind to kinases, p21 and p27 bind to cyclins," *Oncogene* 11:1581–88 (1995).

Harbury, Pehr B. et al. "A Switch Between Two–, Three–and Four–Stranded Coiled Coils in GCN4 Leucine Zipper Mutants," *Science* 262:1401–07 (1993).

Hartwell, Leland H. "Mutants of *Saccharomyces cerevisiae* Unresponsive to Cell Division Control by Polypeptide Mating Hormone," *J. Cell Biol.* 85:811–22 (1980).

Hasson, M.S. et al. "Mutational Activation of the *STE5* Gene Product Bypasses the Requirement for G Protein β and γ Subunits in the Yeast Pheromone Response Pathway," *Molecular and Cellular Biology* 14(2):1054–1065 (1994).

He, Bin et al. "*RAM2*, an essential gene of yeast, and *RAM1* encode the two polyeptide components of the farnesyltransferase that prenylates a–actor and Ras proteins," *Proc. Natl. Acad. Sci. USA* 88:11373–77 (1991).

Hiltunen, J. Kalervo et al. "Peroxisomal Multifunctional β–Oxidation Protein of *Saccharomyces cerevisiae*, " *J. of Biol. Chem.* 267(10):6646–6653 (1992).

Hrycyna, Christine A. et al. "The *Saccharomyces cerevisiae STE*14 gene encodes a methyltransferase that mediates C–terminal methylation of a–factor and RAS Proteins," *The EMBO J.* 10(1):1699–1709 (1991).

Huang, Chi–Ying F. et al. "Ultrasensitivity in the mitogen–activated protein kinase cascade, " *Proc. Natl. Acad. Sci. USA* 93:10078–10083 (1996).

Medici, R. et al. "Efficient signal transduction by a chimeric yeast–mammalian G protein α subunit Gpa 1–Gsα covalently fused to the yeast receptor Ste2," *EMBO* 16:7241–7249 (1997).

Hughes, David A. et al. "Complementation of *byr1* in fission yeast by mammalian MAP kinase kinase requires coexpression of Raf kinase," *Nature* 364:349–52 (1993).

Imamoto, Akira et al. "Genetics of signal transduction: tales from the mouse," *Curr. Opin. Gen. & Dev.* 4:40–46 (1994).

Inouye, Carla et al. "Ste5 RING–H2 Domain: Role in Ste4–Promoted Oligomerization for Yeast Pheromone Signaling," *Science* 278:103–106 (1997).

Jabbar, M. Abdul et al. "Influenza Viral (A/WSN/33) hemagglutinin is expressed and glycosylated in the yeast *Saccharomyces cerevisiae*," *Proc. Natl. Acad. Sci. USA* 82:2019–23 (1985).

Jakobs, K. H. et al. "Dual regulation of adenylate cyclase. A signal transduction mechanism of membrane receptors," *Basic Res. Cardiol.* 81:1–9 (1986).

Journot, Laurent et al. "Amino Acids 367–376 of the $G_s$ α subunit induce membrane association when fused to soluble amino–terminal deleted $G_{i1}$ a subunit," *Proc. Natl. Acad. Sci. USA* 88:10054–58 (1991).

Julius, David et al. "Glycosylation and Processing of Prepro–α–Factor through the Yeast Secretory Pathway," *Cell* 36:309–18 (1984).

Julius, David et al. "Isolation of the Putative Structural Gene for the Lysine–Arginine–Cleaving Endopeptidase Required for Processing of Yeast Prepro–α–factor," *Cell* 37:1075–89 (1984).

Julius, David et al. "Yeast α Factor is Processed from a Larger Precursor Polypeptide: The Essential Role of a Membrane–Bound Dipeptidyl Aminopeptidase," *Cell* 32:839–52 (1983).

Kaiser, Chris A. et al. "Many Random Sequences Functionally Replace the Secretion Signal Sequence of Yeast Invertase," *Science* 235:312–17 (1987).

Kingsman, S.M. et al. "*The production of mammalian protein in Saccharomyces cerevisiae*," *Tibtech* 5:53–57 (1987).

Koff, Andrew et al. "Human Cyclin E, a New Cyclin That Interacts with Two Members of the *CDC2* Gene Family," *Cell* 66:1217–28 (1991).

Kosugi, Shinji et al. "Characterization of heterogeneous mutations causing constitutive activation of the luteinizing hormone receptor in familial male precocious puberty," *Human Molecular Genetics* 4(2):183–88 (1995).

Kramer, R. A. et al. "HTLV–III *gag* Protein Is Processed in Yeast Cells by the Virus *pol*–Protease," *Science* 231:1580–85 (1986).

Kuchler, Karl and Thorner, Jeremy "Functional expression of human *mdr1* in the yeast *Saccharomyces cerevisiae*, " *Proc. Natl. Acad. Sci. USA* 89:2302–06 (1992).

Kuchler, Karl et al. "*Saccharomyces cerevisiae* STE6 gene product: a novel pathway for protein export in eukaryotic cells," *The EMBO J.* 8(13):3973–84 (1989).

Kurjan, Janet "α–Factor Structural Gene Mutations in *Saccharomyces cerevisiae*: Effects on α–Factor Production and Mating," *Molecular and Cellular Biol.* 5(4):787–96 (1985).

Kurjan, Janet and Herskowitz "Structure of a Yeast Pheromone Gene (*MFα*): A Putative α–Factor Precursor Contains Four Random Copies of Mature α–Factor," *Cell* 30:933–43 (1982).

Lambright, David G. et al. "Structural determinants for activation of the α–subunit of a heterotrimeric G protein," *Nature* 369:621–28 (1994).

Lolait, S. et al., "Extrapituitary expression of the rat V1b vasopressin receptor gene," *PNAS USA* 92:6783–6787 (1995).

Lee, Ethan et al. The G22A Mutant of $G_{Sa}$ Highlights the Requirement for Dissociation of G Protein Subunits, *J. Biol. Chem.* 267(2):1212–18 (1992).

Lemire, Bernard D. et al. "The Mitochondrial Targeting Function of Randomly Generated Peptide Sequences Correlates with Predicted Helical Amphiphilicity," *J. Biol. Chem.* 264(34):20206–12 (1989).

Lew, Daniel J. et al. "Isolation of Three Novel Human Cyclins by Rescue of G1 Cyclin (Cln) Function in Yeast," *Cell* 66:1197–1206 (1991).

Linder, Maurine E. and Gilman, Alfred G. "G Proteins," *Scientific American* 267(1):56–65 (1992).

Linder, Maurine E. et al. "Lipid Modifications of G Protein Subunits: Myristoylation of $G_{O_g}$ Increases its Affinity for βγ," *J. Biol. Chem.* 266(7):4654–59 (1991).

Lupas, Andrei N. et al. "Do G protein subunits associate via a three–stranded coiled coil?" *FEBS* 314(2):105–08 (1992).

Mackay, Vivian and Manney, Thomas R. "Mutations Affecting Sexual Conjugation and Related Processes in *Saccharomyces cerevisiae*. II Genectic Analysis of Nonmating Mutants," *Genectics* 76:273–88 (1974).

Marengere, Luc E.M. and Pawson, Tony "Structure and function of SH2 domains," *J. Cell Science* Suppl. 18:97–104 (1994).

Markby, David W. et al. "Separate GTP Binding and GTPase Activating Domains of a Gα Subunits," *Science* 262:1895–1901 (1993).

Michaelis, Susan and Herskowitz, Ira "The a–Factor Pheromone of *Saccharomyces cerevisiae* is Essential for Mating," *Molecular and Cellular Biol.* 8(3):1309–18 (1988).

Milano, C.A. et al. "Enhanced Myocardial Function in Transgenic Mice Overexpressing the $β_2$–Adrenergic Receptor," *Science* 264:582–86 (1994).

Milburn, Michael V. et al. "Molecular Switch for Signal Transduction: Structural Differences Between Active and Inactive Forms of Protooncogenic *ras* Proteins," *Science* 247:939–45 (1990).

Mumby, Susanne M. et al. "G–Protein α–subunit expression, myristoylation, and membrane association in COS cells," *Proc. Natl. Acad. Sci. USA* 87:728–32 (1990).

Murphy, A.J.M. et al. "Autocrine Stimulation of Yeast through Human G–Coupled Receptors," *J. Cell Biochem.* 18B:224 (1994).

Nakafuku, Masato et al. "Occurence in *Saccharomyces cerevisiae* of a gene homologous to the cDNA coding for the α–subunit of mammalian G proteins," *Proc. Natl. Acad. Sci. USA* 84:2140–44 (1987).

Nakayama, N. et al. "Common signal transduction system shared by *STE2* and *STE3* in haploid cells of *Saccharomyces cerevisiae*: autocrine cell–cycle arrest results from forced expression of *STE2*, " *The EMBO J.* 6(1):249–54 (1987).

Neer, Eva J. et al. "The Amino Terminus of a G Protein α Subunits Is Required for Interaction with βγ, " *J. Biol. Chem.* 263(18):8996–9000 (1988).

Noel, Joseph P. et al. "The 2.2 Å crystal structure of transducin–α complexed with GTP–γ–S," *Nature* 366:654–63 (1993).

Noelle, Randolph J. et al. "CD40 and its ligand, an essential ligand–receptor pair for thymus–dependent B–cell activation," *Immunol. Today* 13(11):431–33 (1992).

Nomoto, Satoshi et al. "Regulation of the yeast pheromone response pathway by G protein subunits," *The EMBO J.* 9(3):691–696 (1990).

Nye, Jeffrey S. and Kopan, Raphael "Vertebrate ligands for Notch ," *Current Biology* 5(9):966–69 (1995).

Oeda, Kenji et al. "Expression of Rat Liver Cytochrome P–450MC cDNA in *Saccharomyces cerevisiae*, " *DNA* 4(3):203–10 (1985).

Ogden, Jill E. et al. "Efficient Expression of the *Saccharomyces cerevisiae* PGK Gene Depends on an Upstream Activation Sequence but Does Not Require TATA Sequences," *Molecular and Cellular Biol* . 6(12):4335–43 (1986).

Pronin, Alexey N. and Gautam, Narasimhan "Interaction between G–Protein β and γ subunit types is selective." *Proc. Natl. Acad. Sci. USA* 89:6220–24 (1992).

Ramer, Sandra W. and Davis, Ronald W. "A dominant truncation allele identifies a gene, STE20, that encodes a putative protein kinase necessary for mating in *Saccharomyces cerevisiae*," *Proc. Natl. Acad. Sci USA* 90:452–456 (1993).

Ranade, Koustubh et al. "Mutations associated with familial melanoma impair $p16^{INK4}$ function," *Nature Genetics* 10:114–16 (1995).

Rarick, Helen M. et al. "A Site on Rod G Protein α Subunit That Mediates Effector Activation," *Science* 256:1031–33 (1992).

Raymond, Martine et al. "Functional Complemetation of Yeast ste6 by a Mammalian Multidrug Resistence *mdr* Gene," *Science* 256:232–34 (1992).

Reed, Randall R. "G Protein Diversity and the Regulation of Signaling Pathways," *The New Biologist* 2(11):957–60 (1990).

Schafer, William R. et al. "Enzymatic Coupling of Cholesterol Intermediates to a Mating Pheromone Precursor and to the Ras Protein," *Science* 249:1133–39 (1990).

Schafer, William R. et al. "Genetic and Pharmacological Suppression of Oncogenic Mutations in *RAS* Genes of Yeast and Humans," *Science* 245:379–85 (1989).

Schärer, E. and Iggo, R. "Mammalian p53 can function as a transcription factor in yeast," *Nucleic Acids Research* 20(7):1539–45 (1992).

Scott, Jamie K. and Smith, George P. "Searching for Peptide Ligands with an Epitope Library," *Science* 249:386–90 (1990).

Sikorski, Robert S. and Hieter, Philip "A System of Shutte Vectors and Yeast Host Strains Designed for Efficient Manipulation of DNA in *Saccharomyces cerevisiae*, " *Genetics* 122:19–27 (1989).

Singh, Arjun et al. "*Saccharomyces cerevisiae* contains two discrete genes coding for the α–factor pheromone," *Nucleic Acids Research* 11(12):4049–63 (1983).

Slepak, Vladlen Z. et al. "Mutational Analysis of G Protein α Subunit $G_{o\alpha}$ Expressed in *Escherichia coli*, " *J. Biol. Chem.* 268(2):1414–23 (1993).

Spiegel, Allen M. et al. "The G Protein connection: molecular basis of membrane association," *TIBS* 16:338–41 (1991).

Steube, Klaus et al. "α–Factor–leader–directed secretion of recombinant human–insulin like growth factor I from *Saccharomyces cerevisiae*," *Eur. J. Biochem.* 198:651–57 (1991).

Stevenson, Brian J. et al. "Constitutive mutants of the Protein Kinase STE11 Activate the Yeast Pheromone Response Pathway in the Absence of the G Protein," *Genes & Development* 6:1293–1304 (1992).

Strubin, Michel and Struhl, Kevin "Yeast and Human TFIID with Altered DNA–Binding Specificity of TATA Elements," *Cell* 68:721–30 (1992).

Struhl, Kevin "Constitutive and Inducible *Saccharomyces cerevisiae* Promoters: Evidence for Two Distinct Molecular Mechanisms," *Molecular and Cellular Biol.* 6(11):3847–53 (1986).

Struhl, Kevin et al. "High–frequency transformation of yeast: Autonomous replication of hybrid DNA molecules," *Proc. Natl. Acad. Sci. USA* 76(3):1035–39 (1979).

Struhl, Kevin and Hill, David E. "Two Related Regulatory Sequences are Required for Maximal Induction of *Saccharomyces cerevisiae* his3 Transcription," *Molecular and Cellular Biol.* 7(1):104–10 (1987).

Sullivan, Kathleen A. et al., "Identification of receptor contact site involved in receptor–G protein coupling," *Nature* 330:758–60 (1987).

Suzuki, Takeshi et al. "HTLV–1 Tax protein interacts with cyclin–dependent kinase inhibitor p $16^{INK4A}$ and counteracts its inhibitory activity towards CDK4," *The EMBO J.* 15(7):1607–14 (1996).

Teem, John L. et al. "Identification of Revertants for the Cystic Fibrosis ΔF508 Mutation Using STE6–CFTR Chimeras in Yeast," *Cell* 73:335–346 (1993).

Thomas, Thomas C. et al. "G–protein $\alpha_o$ subunit: Mutation of conserved cysteines identifies a subunit contact surface and alters GDP affinity, " *Proc. Natl. Acad. Sci. USA* 90:10295–99 (1993).

Tyson, John J. et al. "Chemical kinetic theory: understanding cell–cycle regulation," *Trends In Biochem. Sci.* 21:89–96 (1996).

Walker, John E. et al. "Distantly related sequences in the α–and β–subunits of ATP synthase, myosin, kinases and other ATP–requiring enzymes and a common nucleotide binding fold," *The EMBO J.* 1(8):945–51 (1982).

Waters, M. Gerard et al. "Prepro–α–factor Has a Cleavable Signal Sequence," *J. Biol. Chem.* 263(13):6209–14 (1988).

Whiteway, Malcolm S. et al. "Association of the Yeast Pheromone Response G Protein βγ Subunits with the MAP Kinase Scaffold Ste5p," *Science* 269:1572–1575 (1995).

Whiteway, Malcolm et al. "Dominant negative selection of heterologous genes: Isolation of *Candida albicans* genes that interfere with *Saccharomyces cerevicisiae* mating factor–induced cell cycle arrest," *Proc. Natl. Acad. Sci. USA* 89:9410–14 (1992).

Whiteway, Malcolm et al. "The STE4 and STE18 Genes of Yeast Encode Potential β and γ Subunits of the Mating Factor Receptor–Coupled G Protein," *Cell* 56:467–477 (1989).

Wolowiec, D. et al. "Expression of cell cycle regulatory proteins in chronic lymphocytic leukemias, Comparison with non–Hodgkin's lymphomas and non–neoplastic lymphoid tissue," *Leukemia* 9:1382–88 (1995).

Xiong, Y. et al. "Alteration of Cell Cycle Kinase Complexes in Human Papillomavirus E6–and E7–Expressing Fibroblasts Precedes Neoplastic Transformation," *J. Virology* 70(2):999–1008 (1996).

Xiong, Yue et al. "Human D–Type Cyclin," *Cell* 65:691–99 (1991).

Zervos, Antonis S. et al. "Mxi1, a Protein that Specifically Interacts with Max to Bind Myc–Max Recognition Sites," *Cell* 72:223–32 (1993).

Zhan, Xiao–Li et al. "Differential regulation of *FUS*3 MAP kinase by tyrosine–specific phosphatases *PTP2/PTP*3 and dual–specificity phosphatase *MSG*5 in *Saccharomyces cerevisiae*," *Genes & Development* 11:1690–1702 (1997).

Vu et al. "Molecular cloning of a funcional thrombin receptor reveals a novel proteolytic mechanism of receptor actvation" *Cell* 64:1057–1068 (1991).

Bray, P. et al., "Human cDNA clones for four species of G alpha s signal transduction protein," *PNAS USA*, 1986 Dec;83(23):8893–7.

Bray, P. et al., "Human cDNA clones for an alpha subunit of Gi signal–transduction protein," *PNAS USA* 1987 Aug;84(15):5115–9.

Mattera, R. et al., "Identification by molecular cloning of two forms of the alpha–subunit of the human liver stimulatory ($G_s$) regulatory component of adenylyl cylcase," *FEBS Lett.*, 1986 Sep. 29;206(1):35–42.

Dietzel, Christine et al. "Pheromonal regulation and sequence of the *Saccharomyces cerevisiae* SST2 gene: a model for desensitization to pheromone." *Mol. Cell. Biol.* 7(12):4169–4177, Dec. 1987.

Thien–Khai, H.V. et al. "Molecular Cloning of a Funcional Thrombin Receptor Reveals a Novel Proteolytic Mechanism of Receptor Activation" *Cell* 64:1057–1068.

Mattera, R. et al. "Identification by molecular cloning of two forms of the α–subunit of the human liver stimulatory ($G_s$) regulatory component of adenyl cyclase," *FEBS* 206(1):36–41 (1986).

Ngo, J.T. et al. "Computational Complexity, Protein Structure Prediction, and the Levinthal Paradox" in *The Protein Folding Problem and Tertiary Structure Prediction* Merz K.M. et al., eds. Birkhauser, Boston, pp. 433–506 (1994).

Pi, H. et al. (1997) "Transcriptional activation upon pheromone stimulation mediated by a small domain of *Saccharomyces cerevisiae* Ste12p." *Mol. Cell. Biol.* 17(11):6410–6418 (1987).

Reneke, Johanna E. et al. "The carboxy–terminal segment of the yeast alpha–factor receptor is a regulatory domain" *Cell* 55:221–34 (1988).

Boulay, F. et al. "Synthesis and Use of a Novel N–Formyl Peptide Derivative to Isolate a Human N–Formyl Peptide Receptor cDNA" *Biochem. Biophys. Res. Commun.* 168(3):1103–1109 (1990).

Boulay, F. et al. "Expression Cloning of a Receptor for C5a Anaphylatoxin on Differentiated HL–60 Cells" *Biochemistry* 30:2993–2999 (1991).

Murphy, P.M. et al. "Functional Expression of the Human Formyl Peptide Receptor in Xenopus Oocytes Requires a Complementary Human Factor" *J. Biol. Chem.* 266(19):12560–12567 (1991).

Kang, et al. "Molecular & Cellular Biology" 10 (6) 2582–2590, (1990).

* cited by examiner

FIGURE 1

Sequence alignments of N-terminal regions of Gα subunits and N-terminal sequences of GPA₁₁-Gα hybrid proteins.

A. Alignment of GPA1 with Gα Subunits

GPA1
MGC..TVSTQTIGDESDPFLQNKRANDVIEQSLQLEKQRDKNEIKLLLLGAGESGKSTVLKQLKLLHQ......

GαS
MGCLGTS..KTEDQRNEEKAQREANKKIEKQLQKDKQVYRATHRLLLLGAGESGKSTIVKQMRILHV......

Gαi2
MGC.TVS........AEDKAAAERSKMIDKNLREDGEKAAREVKLLLLGAGESGKSTIVKQMKIIHE......

Gαi3
MGC.TVS........AEDKAAVERSKMIDRNLREDGEKAAKEVKLLLLGAGESGKSTIVKQMKIIHE......

Gα16
MARSLTWRCCPWCLTEDEKAAARVDQEINRILLEQKQDRGELKLLLLGPGESGKSTFIKQMRIIHG......

B. GPA₁₁-Gα Hybrids

GPA₁₁- GαS
MGC..TVSTQTIGDESDPFLQNKRANDVIEQSLQL..KQRDKNERKLLLLGAGESGKSTIVKQMRILHV......

GPA₁₁- Gαi2
MGC..TVSTQTIGDESDPFLQNKRANDVIEQSLQLEKQRDKNEVKLLLLGAGESGKSTIVKQMKIIHE......

GPA₁₁- Gαi3
MGC..TVSTQTIGDESDPFLQNKRANDVIEQSLQLEKQRDKNEVKLLLLGAGESGKSTIVKQMKIIHE......

GPA₁₁- Gα16
MGC..TVSTQTIGDESDPFLQNKRANDVIEQSLQLEKQRDKNELKLLLLGPGESGKSTFIKQMRIIHG......

SEQUENCE LISTING

<160> NUMBER OF SEQ ID NOS: 86

<210> SEQ ID NO 1
<211> LENGTH: 10
<212> TYPE: PRT
<213> ORGANISM: Saccharomyces cerevisiae

<400> SEQUENCE: 1

Leu Leu Leu Leu Gly Ala Gly Glu Ser Gly
 1               5                   10

<210> SEQ ID NO 2
<211> LENGTH: 9

```
<212> TYPE: PRT
<213> ORGANISM: Saccharomyces cerevisiae

<400> SEQUENCE: 2

Gly Ser Gly Glu Ser Gly Asp Ser Thr
 1               5

<210> SEQ ID NO 3
<211> LENGTH: 8
<212> TYPE: PRT
<213> ORGANISM: Saccharomyces cerevisiae

<400> SEQUENCE: 3

Gln Ala Arg Lys Leu Gly Ile Gln
 1               5

<210> SEQ ID NO 4
<211> LENGTH: 9
<212> TYPE: PRT
<213> ORGANISM: Saccharomyces cerevisiae

<400> SEQUENCE: 4

Leu Ile His Glu Asp Ile Ala Lys Ala
 1               5

<210> SEQ ID NO 5
<211> LENGTH: 5
<212> TYPE: PRT
<213> ORGANISM: Saccharomyces cerevisiae

<400> SEQUENCE: 5

Asp Val Gly Gly Gln
 1               5

<210> SEQ ID NO 6
<211> LENGTH: 28
<212> TYPE: DNA
<213> ORGANISM: Saccharomyces cerevisiae

<400> SEQUENCE: 6
ggatctagag gatcctggta cgttcctc                                      28

<210> SEQ ID NO 7
<211> LENGTH: 28
<212> TYPE: DNA
<213> ORGANISM: Saccharomyces cerevisiae

<400> SEQUENCE: 7
gtcgctagcc aagcttgcat gcctgcag                                      28

<210> SEQ ID NO 8
<211> LENGTH: 32
<212> TYPE: DNA
<213> ORGANISM: Saccharomyces cerevisiae

<400> SEQUENCE: 8
gcagtcatga gatttccttc aatttttact gc                                 32

<210> SEQ ID NO 9
<211> LENGTH: 30
<212> TYPE: DNA
<213> ORGANISM: Saccharomyces cerevisiae

<400> SEQUENCE: 9
```
cagcccatgg cttcagcctc tcttttatcc                        30

<210> SEQ ID NO 10
<211> LENGTH: 41
<212> TYPE: DNA
<213> ORGANISM: Saccharomyces cerevisiae

<400> SEQUENCE: 10
gatccgctta cccatacgat gttccagatt acgctgcttg a           41

<210> SEQ ID NO 11
<211> LENGTH: 31
<212> TYPE: DNA
<213> ORGANISM: Saccharomyces cerevisiae

<400> SEQUENCE: 11
gatctcaagc agcgtaatct ggaacatcgt a                      31

<210> SEQ ID NO 12
<211> LENGTH: 12
<212> TYPE: PRT
<213> ORGANISM: Saccharomyces cerevisiae

<400> SEQUENCE: 12

Ser Ala Tyr Pro Tyr Asp Val Pro Asp Tyr Ala Ala
 1               5                  10

<210> SEQ ID NO 13
<211> LENGTH: 38
<212> TYPE: DNA
<213> ORGANISM: Saccharomyces cerevisiae

<400> SEQUENCE: 13
gatatattaa ggtaggaaac catggggtgt acagtgag               38

<210> SEQ ID NO 14
<211> LENGTH: 33
<212> TYPE: DNA
<213> ORGANISM: Saccharomyces cerevisiae

<400> SEQUENCE: 14
cgaggctcga gggaacgtat aattaaagta gtg                    33

<210> SEQ ID NO 15
<211> LENGTH: 34
<212> TYPE: DNA
<213> ORGANISM: Saccharomyces cerevisiae

<400> SEQUENCE: 15
gcgcggtacc aagcttcaat tcgagataat accc                   34

<210> SEQ ID NO 16
<211> LENGTH: 24
<212> TYPE: DNA
<213> ORGANISM: Saccharomyces cerevisiae

<400> SEQUENCE: 16
cccgaatcca ccaatttctt tacg                              24

<210> SEQ ID NO 17
<211> LENGTH: 27
<212> TYPE: DNA
<213> ORGANISM: Saccharomyces cerevisiae

```
<400> SEQUENCE: 17
gcggcgtcga cgcggccgcg taacagt                                    27

<210> SEQ ID NO 18
<211> LENGTH: 37
<212> TYPE: DNA
<213> ORGANISM: Saccharomyces cerevisiae

<400> SEQUENCE: 18
ctgctggagc tccgcctgct gctgctgggt gctggag                         37

<210> SEQ ID NO 19
<211> LENGTH: 43
<212> TYPE: DNA
<213> ORGANISM: Saccharomyces cerevisiae

<400> SEQUENCE: 19
ctgctggtcg acgcggccgc gggggttcct tcttagaagc agc                  43

<210> SEQ ID NO 20
<211> LENGTH: 30
<212> TYPE: DNA
<213> ORGANISM: synthetic construct

<400> SEQUENCE: 20
gggctcgagc cttcttagag cagctcgtac                                 30

<210> SEQ ID NO 21
<211> LENGTH: 37
<212> TYPE: DNA
<213> ORGANISM: synthetic construct

<400> SEQUENCE: 21
ctgctggagc tcaagttgct gctgttgggt gctgggg                         37

<210> SEQ ID NO 22
<211> LENGTH: 44
<212> TYPE: DNA
<213> ORGANISM: Saccharomyces cerevisiae

<400> SEQUENCE: 22
ctgctggtcg acgcggccgc gcccctcaga agaggccgcg gtcc                 44

<210> SEQ ID NO 23
<211> LENGTH: 29
<212> TYPE: DNA
<213> ORGANISM: Saccharomyces cerevisiae

<400> SEQUENCE: 23
gggctcgagc ctcagaagag gccgcagtc                                  29

<210> SEQ ID NO 24
<211> LENGTH: 37
<212> TYPE: DNA
<213> ORGANISM: Saccharomyces cerevisiae

<400> SEQUENCE: 24
ctgctggagc tcaagctgct gctactcggt gctggag                         37

<210> SEQ ID NO 25
<211> LENGTH: 49
<212> TYPE: DNA
<213> ORGANISM: Saccharomyces cerevisiae
```

-continued

<400> SEQUENCE: 25
ctgctggtcg acgcggccgc cactaacatc catgcttctc aataaagtc                49

<210> SEQ ID NO 26
<211> LENGTH: 31
<212> TYPE: DNA
<213> ORGANISM: Saccharomyces cerevisiae

<400> SEQUENCE: 26
gggctcgagc atgcttctca ataaagtcca c                                   31

<210> SEQ ID NO 27
<211> LENGTH: 19
<212> TYPE: DNA
<213> ORGANISM: Saccharomyces cerevisiae

<400> SEQUENCE: 27
gcatccatca ataatccag                                                 19

<210> SEQ ID NO 28
<211> LENGTH: 23
<212> TYPE: DNA
<213> ORGANISM: Saccharomyces cerevisiae

<400> SEQUENCE: 28
gaaacaatgg atccacttct tac                                            23

<210> SEQ ID NO 29
<211> LENGTH: 34
<212> TYPE: PRT
<213> ORGANISM: Saccharomyces cerevisiae

<400> SEQUENCE: 29

Gly Tyr Pro Val Ala Gly Ser Asn His Phe Ile Glu Gly Leu Lys Asn
 1               5                  10                  15

Ala Gln Lys Asn Ser Gln Met Ser Asn Ser Asn Ser Val Cys Cys Thr
            20                  25                  30

Leu Met

<210> SEQ ID NO 30
<211> LENGTH: 24
<212> TYPE: PRT
<213> ORGANISM: Homo sapiens

<400> SEQUENCE: 30

Asp Pro Leu Leu Thr Pro Val Pro Ala Ser Glu Asn Pro Phe Arg Glu
 1               5                  10                  15

Lys Lys Phe Phe Cys Ala Ile Leu
            20

<210> SEQ ID NO 31
<211> LENGTH: 33
<212> TYPE: PRT
<213> ORGANISM: Chimaera sp.

<400> SEQUENCE: 31

Gly Tyr Pro Val Ala Gly Ser Asn His Phe Ile Glu Gly Leu Lys Asn
 1               5                  10                  15

Ala Gln Lys Asn Ser Gln Met Ser Asn Ser Asn Ser Val Cys Ala Ile
            20                  25                  30

Leu

<210> SEQ ID NO 32
<211> LENGTH: 22
<212> TYPE: PRT
<213> ORGANISM: Chimaera sp.

<400> SEQUENCE: 32

Gly Tyr Pro Val Ala Gly Ser Asn His Phe Ile Glu Gly Leu Lys Phe
1               5                   10                  15

Phe Cys Cys Thr Leu Met
            20

<210> SEQ ID NO 33
<211> LENGTH: 29
<212> TYPE: PRT
<213> ORGANISM: Chimaera sp.

<400> SEQUENCE: 33

Gly Tyr Pro Val Ala Gly Ser Asn His Phe Ile Glu Gly Leu Lys Asn
1               5                   10                  15

Pro Phe Arg Glu Lys Lys Phe Phe Cys Cys Thr Leu Met
            20                  25

<210> SEQ ID NO 34
<211> LENGTH: 22
<212> TYPE: PRT
<213> ORGANISM: Chimaera sp.

<400> SEQUENCE: 34

Gly Tyr Pro Val Pro Ala Ser Glu Asn Pro Phe Arg Glu Lys Lys Phe
1               5                   10                  15

Phe Cys Cys Thr Leu Met
            20

<210> SEQ ID NO 35
<211> LENGTH: 21
<212> TYPE: PRT
<213> ORGANISM: Chimaera sp.

<400> SEQUENCE: 35

Gly Tyr Pro Val Ala Gly Ser Asn Pro Phe Arg Glu Lys Lys Phe Phe
1               5                   10                  15

Cys Cys Thr Leu Met
            20

<210> SEQ ID NO 36
<211> LENGTH: 21
<212> TYPE: PRT
<213> ORGANISM: Chimaera sp.

<400> SEQUENCE: 36

Gly Tyr Pro Val Ala Gly Ser Asn His Phe Arg Glu Lys Lys Phe Phe
1               5                   10                  15

Cys Cys Thr Leu Met
            20

<210> SEQ ID NO 37
<211> LENGTH: 21
<212> TYPE: PRT
<213> ORGANISM: Chimaera sp.

<400> SEQUENCE: 37

-continued

```
Gly Tyr Pro Val Ala Gly Ser Asn His Phe Ile Glu Lys Lys Phe Phe
 1               5                  10                  15

Cys Cys Thr Leu Met
            20

<210> SEQ ID NO 38
<211> LENGTH: 29
<212> TYPE: PRT
<213> ORGANISM: Chimaera sp.

<400> SEQUENCE: 38

Gly Tyr Pro Val Ala Gly Ser Asn His Phe Ile Glu Gly Leu Lys Asn
 1               5                  10                  15

Pro Phe Lys Glu Leu Lys Gly Gly Cys Cys Thr Leu Met
            20                  25

<210> SEQ ID NO 39
<211> LENGTH: 28
<212> TYPE: PRT
<213> ORGANISM: Chimaera sp.

<400> SEQUENCE: 39

Gly Tyr Pro Val Ala Gly Ser Asn His Phe Ile Glu Gly Leu Lys Asn
 1               5                  10                  15

Pro Phe Arg Pro Gln Lys Val Cys Cys Thr Leu Met
            20                  25

<210> SEQ ID NO 40
<211> LENGTH: 28
<212> TYPE: PRT
<213> ORGANISM: Chimaera sp.

<400> SEQUENCE: 40

Gly Tyr Pro Val Ala Gly Ser Asn His Phe Ile Glu Gly Leu Lys Asn
 1               5                  10                  15

Pro Phe Lys Asp Lys Lys Pro Cys Cys Thr Leu Met
            20                  25

<210> SEQ ID NO 41
<211> LENGTH: 28
<212> TYPE: PRT
<213> ORGANISM: Chimaera sp.

<400> SEQUENCE: 41

Gly Tyr Pro Val Ala Gly Ser Asn His Phe Ile Glu Gly Leu Lys Asn
 1               5                  10                  15

Pro Phe Arg Glu Pro Arg Ser Cys Cys Thr Leu Met
            20                  25

<210> SEQ ID NO 42
<211> LENGTH: 28
<212> TYPE: PRT
<213> ORGANISM: Chimaera sp.

<400> SEQUENCE: 42

Gly Tyr Pro Val Ala Gly Ser Asn His Phe Ile Glu Gly Leu Lys Asn
 1               5                  10                  15

Pro Phe Lys Glu Lys Gly Ser Cys Cys Thr Leu Met
            20                  25

<210> SEQ ID NO 43
```

```
<211> LENGTH: 33
<212> TYPE: PRT
<213> ORGANISM: Chimaera sp.

<400> SEQUENCE: 43

Gly Tyr Pro Val Ala Gly Ser Asn His Phe Ile Glu Gly Leu Lys Asn
  1               5                  10                  15

Ala Gln Lys Asn Pro Phe Arg Glu Lys Lys Phe Phe Cys Cys Thr Leu
             20                  25                  30

Met

<210> SEQ ID NO 44
<211> LENGTH: 28
<212> TYPE: PRT
<213> ORGANISM: Chimaera sp.

<400> SEQUENCE: 44

Gly Tyr Pro Val Ala Gly Ser Asn His Phe Ile Glu Gly Leu Lys Asn
  1               5                  10                  15

Pro Phe Arg Glu Lys Lys Phe Phe Cys Thr Ile Leu
             20                  25

<210> SEQ ID NO 45
<211> LENGTH: 28
<212> TYPE: DNA
<213> ORGANISM: Saccharomyces cerevisiae

<400> SEQUENCE: 45
cccctcgagt tcccttctta gagcagct                                       28

<210> SEQ ID NO 46
<211> LENGTH: 33
<212> TYPE: DNA
<213> ORGANISM: Saccharomyces cerevisiae

<400> SEQUENCE: 46
cccgaagacc aagcttttga ccaggttatt ata                                 33

<210> SEQ ID NO 47
<211> LENGTH: 35
<212> TYPE: DNA
<213> ORGANISM: Saccharomyces cerevisiae

<400> SEQUENCE: 47
aaggaagact tagctttata atttgggctt tagtt                               35

<210> SEQ ID NO 48
<211> LENGTH: 23
<212> TYPE: DNA
<213> ORGANISM: Rattus sp.

<400> SEQUENCE: 48
tttcttgtca ctccgtttct aac                                            23

<210> SEQ ID NO 49
<211> LENGTH: 31
<212> TYPE: DNA
<213> ORGANISM: Rattus sp.

<400> SEQUENCE: 49
ccccgtctca agagcgctgg ccgcccacat c                                   31
```

<210> SEQ ID NO 50
<211> LENGTH: 33
<212> TYPE: DNA
<213> ORGANISM: Rattus sp.

<400> SEQUENCE: 50
ccccgtctca ctctgaacgc cgcaagtgga tcc    33

<210> SEQ ID NO 51
<211> LENGTH: 22
<212> TYPE: DNA
<213> ORGANISM: Rattus sp.

<400> SEQUENCE: 51
agcaagcaga tcttgcttgt tg    22

<210> SEQ ID NO 52
<211> LENGTH: 39
<212> TYPE: DNA
<213> ORGANISM: Rattus sp.

<400> SEQUENCE: 52
gatgtgggcg gccagcgctc tgaacgccgc aagtggatc    39

<210> SEQ ID NO 53
<211> LENGTH: 13
<212> TYPE: PRT
<213> ORGANISM: Rattus sp.

<400> SEQUENCE: 53

Asp Val Gly Gly Gln Arg Ser Glu Arg Arg Lys Trp Ile
 1               5                  10

<210> SEQ ID NO 54
<211> LENGTH: 52
<212> TYPE: DNA
<213> ORGANISM: Homo sapiens

<400> SEQUENCE: 54
tcgtctggag ctcaagctgc tgcttttggg cccaggcgag agcgggaaga gc    52

<210> SEQ ID NO 55
<211> LENGTH: 47
<212> TYPE: DNA
<213> ORGANISM: Homo sapiens

<400> SEQUENCE: 55
ctgctggtcg acgcggccgc gggtcacagc aggttgatct cgtccag    47

<210> SEQ ID NO 56
<211> LENGTH: 39
<212> TYPE: DNA
<213> ORGANISM: Homo sapiens

<400> SEQUENCE: 56
gctaggtctc aaccagtcat cctctttctc aacaaaacc    39

<210> SEQ ID NO 57
<211> LENGTH: 36
<212> TYPE: DNA
<213> ORGANISM: Homo sapiens

<400> SEQUENCE: 57
acgtggtctc atggtgtgct tttgaaccag ggtagt    36

<210> SEQ ID NO 58
<211> LENGTH: 20
<212> TYPE: DNA
<213> ORGANISM: Homo sapiens

<400> SEQUENCE: 58
agcggctgca gattccattc                                         20

<210> SEQ ID NO 59
<211> LENGTH: 45
<212> TYPE: DNA
<213> ORGANISM: Homo sapiens

<400> SEQUENCE: 59
ctaccctggt tcaaaagcac accagtcatc ctctttctca acaaa             45

<210> SEQ ID NO 60
<211> LENGTH: 15
<212> TYPE: PRT
<213> ORGANISM: Homo sapiens

<400> SEQUENCE: 60

Leu Pro Trp Phe Lys Ser Thr Pro Val Ile Leu Phe Leu Asn Lys
 1               5                  10                  15

<210> SEQ ID NO 61
<211> LENGTH: 30
<212> TYPE: DNA
<213> ORGANISM: Homo sapiens

<400> SEQUENCE: 61
gggcgtctca catgggatgt acgctgagcg                              30

<210> SEQ ID NO 62
<211> LENGTH: 28
<212> TYPE: DNA
<213> ORGANISM: Homo sapiens

<400> SEQUENCE: 62
ggggtcgact cagtagagtc aacagccc                                28

<210> SEQ ID NO 63
<211> LENGTH: 40
<212> TYPE: DNA
<213> ORGANISM: Homo sapiens

<400> SEQUENCE: 63
cccccgtctc atagggtat caatgaaaaa cttgttgtta                    40

<210> SEQ ID NO 64
<211> LENGTH: 35
<212> TYPE: DNA
<213> ORGANISM: Homo sapiens

<400> SEQUENCE: 64
cccccgtctc acctatcatc ctcttcctca acaag                        35

<210> SEQ ID NO 65
<211> LENGTH: 48
<212> TYPE: DNA
<213> ORGANISM: Homo sapiens

<400> SEQUENCE: 65

```
aacaacaagt ttttcattga taccoctatc atcctcttcc tcaacaag        48

<210> SEQ ID NO 66
<211> LENGTH: 15
<212> TYPE: PRT
<213> ORGANISM: Homo sapiens

<400> SEQUENCE: 66

Asn Asn Lys Phe Ile Asp Thr Pro Ile Ile Leu Phe Leu Asn Lys
 1               5                  10                  15

<210> SEQ ID NO 67
<211> LENGTH: 65
<212> TYPE: DNA
<213> ORGANISM: Chimaera sp.

<400> SEQUENCE: 67
aaaagagcca atgatgtcat cgagcaatcg ttgcagctgg agaaacaacg tgacaagaat    60
gagct                                                                65

<210> SEQ ID NO 68
<211> LENGTH: 65
<212> TYPE: DNA
<213> ORGANISM: Chimaera sp.

<400> SEQUENCE: 68
cattcttgtc acgttgtttc tccagctgca acgattgctc gatgacatca ttggctcttt    60
tgttc                                                                65

<210> SEQ ID NO 69
<211> LENGTH: 61
<212> TYPE: DNA
<213> ORGANISM: Chimaera sp.

<400> SEQUENCE: 69 catgggtgt acagtgagta cgcaaacaat aggagatgaa agtgatcctt ttctgcagaa     60
c                                                                    61

<210> SEQ ID NO 70
<211> LENGTH: 53
<212> TYPE: DNA
<213> ORGANISM: Chimaera sp.

<400> SEQUENCE: 70
ygcagaaaag gatcactttc atctcctatt gtttgcgtac tcactgtaca ccc           53

<210> SEQ ID NO 71
<211> LENGTH: 25
<212> TYPE: DNA
<213> ORGANISM: Chimaera sp.

<400> SEQUENCE: 71
cttcttcaac gtccccatca tcctc                                          25

<210> SEQ ID NO 72
<211> LENGTH: 25
<212> TYPE: DNA
<213> ORGANISM: Chimaera sp.

<400> SEQUENCE: 72
gaggatgatg gggacgttga agaag                                          25
```

<210> SEQ ID NO 73
<211> LENGTH: 25
<212> TYPE: DNA
<213> ORGANISM: Chimaera sp.

<400> SEQUENCE: 73
ggatgtgggc gcccagaggt cacag                                       25

<210> SEQ ID NO 74
<211> LENGTH: 25
<212> TYPE: DNA
<213> ORGANISM: Chimaera sp.

<400> SEQUENCE: 74
ctgtgacctc tgggcgccca catcc                                       25

<210> SEQ ID NO 75
<211> LENGTH: 80
<212> TYPE: DNA
<213> ORGANISM: Chimaera sp.

<400> SEQUENCE: 75
gcggagctcm nnmnnmnnmn nmnncttttc taattgcaag gattgttcga taacgtcatt  60
agctctctta ttctgcaggg                                             80

<210> SEQ ID NO 76
<211> LENGTH: 50
<212> TYPE: DNA
<213> ORGANISM: Chimaera sp.

<400> SEQUENCE: 76
ccctgcagaa taagagagct aatgacgtta tcgaacaatc cttgcaatta            50

<210> SEQ ID NO 77
<211> LENGTH: 20
<212> TYPE: DNA
<213> ORGANISM: Rattus sp.

<400> SEQUENCE: 77
gcatcacatc aataatccag                                             20

<210> SEQ ID NO 78
<211> LENGTH: 30
<212> TYPE: DNA
<213> ORGANISM: Rattus sp.

<400> SEQUENCE: 78
aacccggaac gatttaacga gatcaagaac                                  30

<210> SEQ ID NO 79
<211> LENGTH: 9
<212> TYPE: PRT
<213> ORGANISM: Rattus sp.

<400> SEQUENCE: 79

Leu Glu Lys Gln Arg Asp Lys Asn Glu
 1               5

<210> SEQ ID NO 80
<211> LENGTH: 6
<212> TYPE: PRT
<213> ORGANISM: Rattus sp.

```
<400> SEQUENCE: 80

Gly Xaa Gly Xaa Xaa Gly
 1               5

<210> SEQ ID NO 81
<211> LENGTH: 10
<212> TYPE: PRT
<213> ORGANISM: Rattus sp.

<400> SEQUENCE: 81

Leu Leu Leu Leu Gly Ala Gly Glu Ser Glu
 1               5                  10

<210> SEQ ID NO 82
<211> LENGTH: 6
<212> TYPE: PRT
<213> ORGANISM: Rattus sp.

<400> SEQUENCE: 82

Met Gly Xaa Ala Ala Ser
 1               5

<210> SEQ ID NO 83
<211> LENGTH: 4
<212> TYPE: PRT
<213> ORGANISM: Rattus sp.

<400> SEQUENCE: 83

Cys Ala Ala Xaa
 1

<210> SEQ ID NO 84
<211> LENGTH: 20
<212> TYPE: DNA
<213> ORGANISM: Rattus sp.

<400> SEQUENCE: 84
acccggaacg atttaacgag                                          20

<210> SEQ ID NO 85
<211> LENGTH: 20
<212> TYPE: DNA
<213> ORGANISM: Rattus sp.

<400> SEQUENCE: 85
gattggagcc ggtgactacc                                          20

<210> SEQ ID NO 86
<211> LENGTH: 6
<212> TYPE: PRT
<213> ORGANISM: Saccharomyces cerevisiae

<400> SEQUENCE: 86

Lys Arg Glu Ala Glu Ala
 1               5
```

YEAST CELLS EXPRESSING MODIFIED G PROTEINS AND METHODS OF USE THEREFOR

CROSS REFERENCE TO RELATED APPLICATIONS

This application is a continuation-in-part of U.S. Ser. No. 08/689,172, filed on Aug. 6, 1996 now abandoned, which is a continuation-in-part of U.S. Ser. No. 08/582,333, filed Jan. 17, 1996, now U.S. Pat. No. 6,255,059, which is a continuation-in-part of U.S. Ser. No. 08/463,181, filed Jun. 5, 1995, now abandoned, which is a continuation-in-part of U.S. Ser. No. 08/322,137, filed Oct. 13, 1994, now U.S. Pat. No. 6,100,042, which is a continuation-in-part of U.S. Ser. No. 08/309,313, filed Sep. 20, 1994, now abandoned, which is a continuation-in-part of U.S. Ser. No. 08/190,328, filed Jan. 31, 1994, now abandoned, which is a continuation-in-part of U.S. Ser. No. 08/041,431, filed Mar. 31, 1993, now abandoned, the specifications of which are hereby incorporated by reference.

BACKGROUND OF THE INVENTION

Cell surface receptors are an important class of proteins involved in cellular functioning because they are the primary mediators of cell to cell communication. G protein coupled receptors (GPCRs) are an important category of cell surface receptors. The medical importance of these receptors is evidenced by the fact that more than 60% of all commercially available prescription drugs work by interacting with known GPCRs.

In their resting state, the G proteins, which consist of alpha ($\alpha$), beta ($\beta$) and gamma ($\gamma$) subunits, are complexed with the nucleotide guanosine diphosphate (GDP) and are in contact with the receptors to which they are coupled. When a hormone or other first messenger binds to receptor, the receptor changes conformation and this alters its interaction with the G protein. This spurs the $\alpha$ subunit to release GDP, and the more abundant nucleotide guanosine triphosphate (GTP) replaces it, activating the G protein. The G protein then dissociates to separate the $\alpha$ subunit from the still complexed beta and gamma subunits. Either the G$\alpha$ subunit, or the G$\beta\gamma$ complex, depending on the pathway, interacts with an effector. The effector (which is often an enzyme) in turn converts an inactive precursor molecule into an active "second messenger," which may diffuse through the cytoplasm, triggering a metabolic cascade. After a few seconds, the G$\alpha$ converts the GTP to GDP, thereby inactivating itself. The inactivated G$\alpha$ may then reassociate with the G$\beta\gamma$ complex.

Hundreds, if not thousands, of receptors convey messages through heterotrimeric G proteins, of which at least 17 distinct forms have been isolated. Most G protein-coupled receptors are comprised of a single protein chain that is threaded through the plasma membrane seven times. Such receptors are often referred to as seven-transmembrane receptors (STRs). More than a hundred different GPCRs have been found, including many distinct receptors that bind the same ligand, and there are likely many more GPCRs awaiting discovery. The development of new drug discovery assays to identify novel modulators of GPCRs would be of tremendous benefit.

In recent years drug discovery has been advanced by expression of heterologous receptors in living cells. However, due to the complexity of GPCRs the search for modulators of these receptors have presented particular challenges. For example, there is variability in the sequences of G protein subunits and this variability can influence the efficiency of receptor coupling to subunits. The highest variability has been seen in the $\alpha$ subunit, but several different $\beta$ and $\gamma$ structures have also been reported. There are, additionally, several different G protein-dependent effectors.

The mating factor receptors of yeast cells (STE2 and STE3) span the membrane of the yeast cell seven times and are coupled to yeast G proteins. The GPA1, STE4, and STE18 products are the yeast homologues of the $\alpha$, $\beta$ and $\gamma$ subunits of mammalian G proteins, respectively. (Nakafuku et al. 1987. *Proc. Natl. Acad. Sci USA* 84:2140; Whiteway et al. 1989. *Cell.* 56:467). Since yeast cells have GPCRs analogous to those found in mammalian cells, experiments have also been undertaken to express functional GPCRs in yeast cells. The use of yeast cells for such expression provides advantages in terms of the ease of manipulating the cells, but also presents particular challenges in achieving efficient coupling and functional integration.

Methods for improving the functional integration of heterologous GPCRs in yeast cells are still needed. The prior art teaches numerous examples of the expression of heterologous receptors in yeast cells which fail to couple to yeast G proteins and thus are not functionally integrated into a yeast signaling pathway. For example Huang et al. teach that the rat M5 receptor, when expressed in yeast cells did not couple to the pheromone response pathway (Huang et al. *Biochem. and Biophys. Res. Comm.* 1992. 182:1180).

Previous work has demonstrated coupling of heterologous receptors in yeast by the expression of entire foreign G protein subunits in yeast cells (U.S. Pat. No. 5,482,835 to King et al.). Another approach was taken by Kang (1990 *Mol. Cell. Biol.* 10:2582–2590) who made GPA1-G$\alpha$ chimeric subunits which comprised large portions, e.g., over 300 amino acids of GPA1. However, the chimeras made by Kang et al. were assayed for their ability to complement a gpa1 null phenotype (i.e., constitutive activation of the pheromone response pathway) in *S. cerevisiae*, a situation in which it was desirable to retain a substantial portion of the GPA sequence. Clearly, a method for optimizing the functional integration of a heterologous GPCR into a signaling pathway in a yeast cell expressing such a receptor would be of great value in developing assays to identify receptor agonists and antagonists.

SUMMARY OF THE INVENTION

The present invention provides an important advance in drug screening methodologies previously known in the art by providing, inter alia, a means by which expression of heterologously expressed receptors is enhanced and a means by which coupling of heterologously expressed GPCRs to G protein subunits is enhanced.

The present invention pertains to novel yeast cells which are useful for the expression of functional heterologous GPCRs. In certain embodiments, the subject yeast cells comprise modified and/or heterologous G protein subunits which enhance the functional integration of heterologous GPCRs into a yeast signaling pathway. The modified G protein subunits can be altered by mutation and/or can be chimeric, i.e., can comprise a polypeptide derived from a yeast G protein subunit and a second polypeptide derived from a heterologous G protein subunit. The yeast cells of the present invention can be used in novel screening assays which can be used to screen for modulators of GPCRs.

In one aspect, the invention provides a yeast cell comprising a heterologous G protein coupled receptor; and a non-naturally occurring G protein subunit which has a sequence from a heterologous G protein subunit, but in which at least one amino acid substitution has been introduced compared to the wild type sequence. The expression of the non-naturally occurring G protein subunit functionally integrates the heterologous G protein coupled receptor into the yeast cell pheromone signaling pathway.

In one embodiment, the yeast cell of of the present invention has a non-naturally occurring G protein subunit which is a mutant mammalian Gα subunit. In preferred embodiments, the mutatnt mammalian Gα subunit comprises a sequence from a heterologous G protein subunit having a mutation selected from the group consisting of: Gα16(S270P); Gαs(D229S); Gαs(D229V); Gαs(N254D); Gαs(S286P); Gαs(E10K); Gαi2-GαoB(S280P); Gα12 (Q229L); Gα12(G228A); and Gαi2(S288P).

In another embodiment, the yeast cell of the present invention comprises a non-naturally occurring G protein subunit which is a yeast-mammalian G protein subunit chimera comprising a first polypeptide from a yeast G protein subunit and a second polypeptide from a mutant mammalian G protein subunit. In preferred embodiments the second polypeptide of the chimera comprises a mutant mammalian Gα subunit selected from the group consisting of: Gα16(S270P); Gαs(D229S); Gαs(D229V); Gαs (N254D); Gαs(S286P); Gαs(E10K); Gαi2-GαoB(S280P); Gα12(Q229L); Gα12(G228A); and Gαi2(S288P).

In another preferred embodiment, a yeast cell of the present invention has a chimeric G protein subunit, which comprises a first polypeptide from a yeast G protein subunit and a second polypeptide from a heterologous G protein subunit, where the first polypeptide is selected from the group consisting of: a polypeptide comprising about 40 amino acids from the amino terminus of yeast GPA1; and a polypeptide from yeast STE 18.

In yet another preferred embodiment, a yeast cell of the present invention has a chimeric G protein subunit where the first polypeptide of the chimera comprises about 40 amino acids from the amino terminus of yeast GPA1 and said second polypeptide of the chimera is from a heterologous G protein α subunit.

In yet another embodiment a yeast cell of the present invention has a chimeric G protein subunit in which the first polypeptide is from yeast STE 18 and the second polypeptide is from a heterologous G protein γ subunit.

In preferred embodiments, a heterologous G protein subunit of the present invention is mammalian. In particularly preferred embodiments, a heterologous G protein subunit of the present invention is human.

In one embodiment, a yeast cell of the present invention comprises a chimeric G protein subunit in which at least one of the first and second polypeptides comprises a naturally occurring amino acid sequence. In still another embodiment, at least one of the first and second polypeptides of the chimeric G protein subunit comprises a non-naturally occurring amino acid sequence.

In preferred embodiments, a yeast cell of the present invention comprises a heterologous G protein coupled receptor which is functionally integrated into the yeast cell. In particularly preferred embodiments, a modified or chimeric G protein subunit of the present invention demonstrates enhanced coupling to a heterologous G protein coupled receptor expressed by a yeast cell when compared to that demonstrated by an endogenous yeast G protein subunit.

In one embodiment a yeast cell of the present invention comprises a chimeric G protein subunit in which the second polypeptide is from the human Gγ2 subunit. In a preferred embodiment, the second polypeptide comprises the amino acid sequence Arg Glu Lys Lys Phe Phe (amino acids 19–24 of SEQ ID NO: 33). In a particularly preferred embodiment, the chimeric G protein subunit comprises the sequence shown in SEQ ID NO: 33.

In a preferred embodiment, a yeast cell of the present invention comprises a chimeric G protein subunit selected from the group consisting of: gpa1 (41)-Gαi2; gpa1 (41)-Gα16; and gpa1 (41)-Gαs. In a more preferred embodiment, a yeast cell of the present invention comprises a chimeric G protein subunit in which the Gαi2, Gα16, or Gαs portion of the chimeric G protein subunit comprises an amino acid substitution compared to wild type Gαi2, Gα16, or Gαs.

In yet another embodiment, a yeast cell of the present invention comprises a second chimeric G protein subunit, in which the second chimeric G protein subunit has a first polypeptide from a yeast G protein subunit and a second polypeptide from a mammalian G protein subunit, and wherein the second chimeric G protein subunit is different from a first chimeric G protein subunit expressed by the yeast cell. In a preferred embodiment, the second polypeptide of the second chimeric G protein subunit is from a protein selected from the group consisting of: a mammalian Gα subunit, a mammalian Gβ subunit, and a mammalian Gγ subunit.

In preferred embodiments, a yeast cell of the present invention does not produce an endogenous yeast pheromone system receptor protein in functional form.

In certain embodiments, a yeast cell of the present invention comprises a indicator gene that produces a detectable signal upon functional coupling of the heterologous G protein coupled receptor to the G protein.

In preferred embodiments, a yeast cell of the present invention comprises a heterologous G protein coupled receptor which is an orphan receptor.

In another embodiment the invention provides an assay to identify compounds capable of modulating the dissociation of Gα and Gβγ, comprising the steps of: providing a yeast cell which comprises a heterologous G protein coupled receptor, a modified G protein subunit, and an indicator gene, contacting the yeast with a test compound; and identifying compounds which induce a change in a detectable signal in the yeast cell, wherein said detectable signal indicates dissociation of Gα and Gβγ.

In certain embodiments, an assay of the present invention is used to test compounds from a library of non-peptidic organic molecules.

In another aspect, the invention provides a method for identifying a compound which modulates a heterologous G protein coupled receptor, comprising: providing a first, second, third, and fourth yeast cell, each cell comprising a G protein, wherein:

1) the first yeast cell comprises a first chimeric G protein subunit comprising a first polypeptide from a yeast G protein subunit and a second polypeptide from a mammalian G protein subunit; 2) the second yeast cell comprises a second chimeric G protein subunit comprising a first polypeptide derived from a yeast G protein subunit and a second polypeptide from a mammalian G protein subunit, the second chimeric G protein subunit being different from said first chimeric G protein subunit; 3) the third yeast cell comprises a third chimeric G protein subunit comprising a first polypeptide from a yeast G protein subunit and a second polypeptide from a mammalian G protein subunit, the third chimeric G protein subunit being different from said first and second chimeric G protein subunits; 4) the fourth yeast cell comprises an endogenous yeast gpa1 G protein subunit; and an expressible gene construct encoding a heterologous G protein coupled receptor (GPCR) which couples to the yeast pheromone system pathway; and an indicator gene that produces a detectable signal upon functional coupling of the heterologous G protein coupled receptor to the G protein. The assay comprises contacting the first, second, third, and fourth yeast cells with a test compound; and determining whether the test compound induces a change in a detectable signal in at least one of the first, second, third, or fourth yeast cells to thereby identify a compound which modulates a heterologous GPCR.

In preferred embodiments, the assay is performed using a yeast cell which comprises a chimeric G protein subunit in which the second polypeptide is from a mammalian Gαi subunit. In another preferred embodiment, the second polypeptide of the chimeric G protein subunit is from a mammalian Gα16 subunit. In yet another preferred embodiment, the second polypeptide of the chimeric G protein subunit is from a mammalian Gαs subunit.

In yet another embodiment of the assay, the first chimeric G protein subunit comprises a polypeptide from mammalian Gα12, the second chimeric G protein subunit comprises a polypeptide from mammalian Gα16, and the third chimeric G protein subunit comprises a polypeptide from mammalian Gαs. In a preferred embodiment, the second chimeric G protein subunit comprises Gα16(S270P) and the third chimeric G protein subunit comprises Gαs(D229S).

In another preferred embodiment, each of the first, second, and third yeast cells further comprises a fourth chimeric G protein subunit, said fourth chimeric G protein subunit comprising a first polypeptide from yeast STE18 and a second polypeptide from a mammalian G protein γ subunit.

In certain embodiments of the subject assays, the first, second, third, and fourth yeast cells are contacted with each member of a library of test compounds. In a preferred embodiment, each member of said library is a non-peptidic organic molecule.

In a preferred embodiment, the first, second, third, and fourth yeast cells are *Saccharomyces cerevisiae* cells.

In one embodiment of the invention, the indicator gene that gives rise to a detectable signal is selected from the group consisting of: β galactosidase, alkaline phosphatase, horseradish peroxidase, exoglucanase, luciferase, BAR1, PHO5, green fluorescent protein and chloramphenicol acetyl transferase.

In yet another embodiment, the indicator gene that gives rise to a detectable signal is a HIS3 gene.

In one embodiment of the invention, the heterologous G protein coupled receptor which is expressed by a yeast cell is an orphan receptor.

BRIEF DESCRIPTION OF THE INVENTION

FIG. 1 is a sequence alignment of N-terminal regions of Gα subunits and N-terminal sequences of GPA41-Gα hybrid proteins.

DETAILED DESCRIPTION OF THE INVENTION

Figure 2:
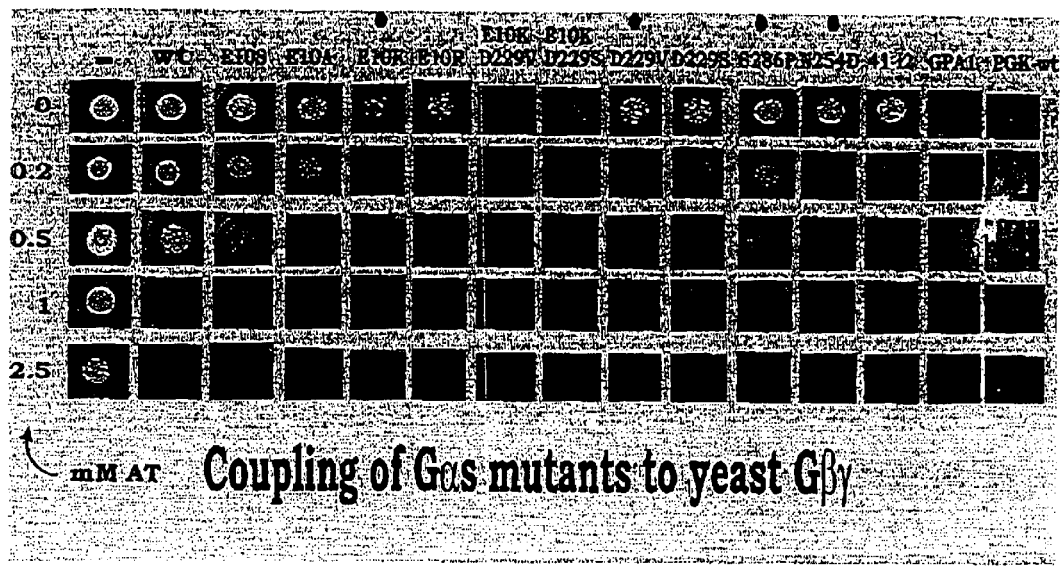
FIG. 2 is an illustration of the effect of mutations to a mammalian G protein subunit, Gαs, on the coupling of the mammalian Gαs subunit to yeast Gβγ.

The present invention provides, inter alia, rapid, effective assays for screening and identifying pharmaceutically effective compounds that specifically modulate the activity of a heterologous G protein coupled receptor (GPCR) expressed in a yeast cell. The subject assays enable rapid screening of large numbers of compounds (e.g., compounds in a library) to identify those which are receptor agonists or antagonists. Compositions of matter, such as novel recombinant yeast cells and novel gene constructs are also embraced by the present invention. The instant assays provide a convenient format for discovering compounds which can be useful to modulate cellular function, as well as to understand the pharmacology of compounds that specifically interact with cellular receptors.

In the practice of the instant invention, standard techniques known in the art can be used. See for example, Sherman. 1991. Methods Enzymol. 194:3; Sherman and Hicks. 1991. Methods Enzymol. 194:21; Sambrook et al. *Molecular Cloning A Laboratory Manual*, 2nd Ed., ed. by Sambrook, Fritsch and Maniatis (Cold Spring Harbor Laboratory Press: 1989 or 1991 edition.

Before further description of the invention, certain terms employed in the specification, examples and appended claims are, for convenience, collected here.

I. Definitions

The term "compound" as used herein (e.g., as in "test compound") is meant to include both exogenously added test compounds and peptides endogenously expressed from a peptide library. For example, in certain embodiments, the reagent cell also produces the test compound which is being screened. For instance, the reagent cell can produce. e.g., a test polypeptide, a test nucleic acid and/or a test carbohydrate which is screened for its ability to modulate the heterologous receptor activity. In such embodiments, a culture of such reagent cells will collectively provide a library of potential effector molecules and those members of the library which either agonize or antagonize the receptor function can be selected and identified. Moreover, it will be apparent that the reagent cell can be used to detect agents which transduce a signal via the receptor of interest.

In other embodiments, the test compound is exogenously added. In such embodiments the test compound is contacted with the reagent cell. Exemplary compounds which can be screened for activity include, but are not limited to, peptides, nucleic acids, carbohydrates, small organic molecules, and natural product extract libraries. In such embodiments, both compounds which agonize or antagonize the receptor mediated signaling function can be selected and identified.

The term "non-peptidic compound" is intended to encompass compounds that are comprised, at least in part, of molecular structures different from naturally-occurring L-amino acid residues linked by natural peptide bonds. However, "non-peptidic compounds" are intended to include compounds composed, in whole or in part, of peptidomimetic structures, such as D-amino acids, non-naturally-occurring L-amino acids, modified peptide backbones and the like, as well as compounds that are composed, in whole or in part, of molecular structures unrelated to naturally-occurring L-amino acid residues linked by natural peptide bonds. "Non-peptidic compounds" also are intended to include natural products.

As used herein, "recombinant cells" include any cells that have been modified by the introduction of heterologous DNA. Control cells include cells that are substantially identical to the recombinant cells, but do not express one or more of the proteins encoded by the heterologous DNA, e.g., do not include or express a reporter gene construct, receptor or test polypeptide.

As used herein, "heterologous DNA" or "heterologous nucleic acid" includes DNA that does not occur naturally as part of the genome in which it is present or which is found in a location or locations in the genome that differs from that in which it occurs in nature. Heterologous DNA is not naturally occurring in that position or is not endogenous to the cell into which it is introduced, but has been obtained from another cell. Generally, although not necessarily, such DNA encodes proteins that are not normally produced by the cell in which it is expressed. Heterologous DNA can be from the same species, although in preferred embodiments, it is from a different species. In particularly preferred embodiments, it is mammalian, e.g., human. Heterologous DNA may also be referred to as foreign DNA. Any DNA that one of skill in the art would recognize or consider as heterologous or foreign to the cell in which is expressed is herein encompassed by the term heterologous DNA. Examples of heterologous DNA include, but are not limited to, DNA that encodes test polypeptides, receptors, reporter genes, transcriptional and translational regulatory sequences, or selectable or traceable marker proteins, such as a protein that confers drug resistance.

The terms "heterologous protein", "recombinant protein", and "exogenous protein" are used interchangeably throughout the specification and refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid. "Orphan receptors" is a designation given to a receptors for which no specific natural ligand yet been described.

As used herein, the term "extracellular signal" is intended to encompass molecules and changes in the environment that are transduced intracellularly via cell surface proteins that interact, directly or indirectly, with the extracellular signal. An extracellular signal or effector molecule includes any compound or substance that in some manner alters the activity of a cell surface protein. Examples of such signals include, but are not limited to, molecules such as acetylcholine, growth factors and hormones, lipids, sugars and nucleotides that bind to cell surface receptors and modulate the activity of such receptors. The term, "extracellular signal" also includes as yet unidentified substances that modulate the activity of a cellular receptor, and thereby influence intracellular functions. Such extracellular signals are potential pharmacological agents that may be used to treat specific diseases by modulating the activity of specific cell surface receptors.

As used herein, "cell surface receptor" refers to molecules that occur on the surface of cells, interact with the extracellular environment, and transmit or transduce the information regarding the environment intracellularly in a manner that may modulate intracellular second messenger activities or transcription of specific promoters, resulting in transcription of specific genes. A "heterologous receptor" is a specific embodiment of a "heterologous protein", wherein the heterologous receptor is encoded by heterologous DNA and, upon expression of this heterologous DNA in a recombinant cell, the heterologous receptor is expressed in the recombinant cell. Preferred receptors are G protein coupled receptors and exemplary GPCRs are described in detail herein.

The term "signal transduction" is intended to encompass the processing of physical or chemical signals from the extracellular environment through the cell membrane and into the cell, and may occur through one or more of several mechanisms, such as activation/inactivation of enzymes (such as proteases, or other enzymes which may alter phosphorylation patterns or other post-translational modifications), activation of ion channels or intracellular ion stores, effector enzyme activation via guanine nucleotide binding protein intermediates, formation of inositol phosphate, activation or inactivation of adenylyl cyclase, direct activation (or inhibition) of a transcriptional factor and/or activation. A "signaling pathway" refers to the components involved in "signal transduction" of a particular signal into a cell. The term "endogenous signaling pathway" indicates that some or all of the components of the signaling pathway are naturally-occurring components of the cell. An example of such a pathway is the endogenous pheromone system pathway of yeast.

The term "functionally integrated" (as in a receptor that is "functionally integrated into a signaling pathway in a cell" or "functionally integrated into an endogenous yeast signaling pathway") is intended to refer to the ability of the receptor to be expressed at the surface of the cell and the ability of the expressed receptor to bind to modulators(e.g., a ligand of the receptor) and transduce signals into the cell via components of a signaling pathway of the cell. For example, a G protein coupled receptor (GPCR) which is functionally integrated into an endogenous pheromone response pathway of a yeast cell is expressed on the surface of the yeast cell, couples to a G protein of the pheromone response pathway within the yeast cell and transduces a signal in that yeast cell upon binding of a modulator to the receptor. For a G protein subunit to be functionally integrated into a yeast cell such a subunit, e.g., a chimeric, mutant or heterologous subunit, must be capable of coupling both to the GPCR and to the other G protein subunits, which can also be endogenous to the yeast cell, can be chimeric, or can be heterologous. A transduced signal may be detected by measuring any one of a number of responses to mating factors which occur in a yeast cell, e.g., growth arrest or transcription of an indicator gene responsive to signals produced by modulation of a pheromone system pathway.

The term "indicator gene" generically refers to an expressible (e.g., able to transcribed and (optionally) translated) DNA sequence which is expressed in response to a signal transduction pathway modulated by a target receptor or ion channel. Exemplary indicator genes include unmodified endogenous genes of the host cell, modified endogenous genes, or a reporter gene of a heterologous construct, e.g., as part of a reporter gene construct.

The term "endogenous gene" is intended to refer to a gene in a cell that is naturally part of the genome of the cell and which, most preferably, is present in its natural location in the genome (as opposed to "heterologous" DNA which has been introduced into the cell). Likewise, the term "endogenous protein" is intended to include proteins of a cell that are encoded by endogenous genes of the cell.

An endogenous gene that is to be used as an indicator gene may comprise the natural regulatory elements of the gene (e.g., the native promoter/enhancer elements that naturally regulate expression of the gene) or the endogenous gene can be "operatively linked to" (i.e., functionally coupled to) a "heterologous promoter" (or other heterologous regulatory elements). A "heterologous promoter" refers to a promoter that does not naturally regulate the gene to which the heterologous promoter is operatively linked. For example, an endogenous yeast gene that is not normally pheromone-responsive can be operatively linked to a heterologous promoter that is responsive to signals produced by the yeast pheromone system to thereby confer pheromone responsiveness on the endogenous yeast gene. Methods of using endogenous yeast genes as indicator genes are described further in U.S. Ser. No. 08/936,632 entitled, "Methods and Compositions for Identifying Receptor Effectors", filed on Sep. 24, 1997 the contents of which are hereby expressly incorporated herein by this reference.

The term "detecting an alteration in a signal produced by an endogenous signaling pathway" (e.g., an endogenous yeast signaling pathway) is intended to encompass the detection of alterations in endogenous second messengers produced upon activation of components of the endogenous signaling pathway, alterations in endogenous gene transcription induced upon activation of components of the endogenous signaling pathway, and/or alterations in the activity of an endogenous protein(s) upon activation of components of the endogenous signaling pathway. In certain embodiments, the term "detecting an alteration in a signal produced by an endogenous signaling pathway" can also encompass assaying general, global changes to the cell such as changes in cell growth or cell morphology.

As used herein, a "reporter gene construct" refers to a nucleic acid that includes a "reporter gene" operatively linked to a transcriptional regulatory sequences. Transcription of the reporter gene is controlled by these sequences. The activity of at least one or more of these control sequences is directly or indirectly regulated by the target receptor protein. The transcriptional regulatory sequences include the promoter and other regulatory regions, such as enhancer sequences, that modulate the activity of the promoter, or regulatory sequences that modulate the activity or efficiency of the RNA polymerase that recognizes the promoter, or regulatory sequences which are recognized by effector molecules, including those that are specifically induced by interaction of an extracellular signal with the target receptor. For example, modulation of the activity of the promoter may be effected by altering the RNA polymerase binding to the promoter region, or, alternatively, by interfering with initiation of transcription or elongation of the mRNA. Such sequences are herein collectively referred to as transcriptional regulatory elements or sequences. In addition, the construct may include sequences of nucleotides that alter translation of the resulting mRNA, thereby altering the amount of reporter gene product. The reporter gene constructs of the present invention provide a detectable readout in response to signals transduced in response to modulation of a heterologously expressed receptor.

The term "modulation", as in "modulation of a (heterologous) receptor" and "modulation of a signal transduction activity of a receptor protein" is intended to encompass, in its various grammatical forms, induction and/or potentiation, as well as inhibition and/or downregulation of receptor activity and/or one or more signal transduction pathways downstream of a receptor.

Agonists and antagonists are "receptor effector" molecules that modulate signal transduction via a receptor. Receptor effector molecules are capable of binding to the receptor, though not necessarily at the binding site of the natural ligand or otherwise modulating the activity of the receptor, for example, by influencing the activity of components which regulate the receptor, or which function in the signal transduction pathway initiated by the receptor. Receptor effectors can modulate signal transduction when used alone, i.e. can be surrogate ligands, or can alter signal transduction in the presence of the natural ligand or other known activators, either to enhance or inhibit signaling by the natural ligand. For example, "antagonists" are molecules that block or decrease the signal transduction activity of receptor, e.g., they can competitively, noncompetitively, and/or allosterically inhibit signal transduction from the receptor, whereas "agonists" potentiate, induce or otherwise enhance the signal transduction activity of a receptor. The term "surrogate ligand" refers to an agonist which induces signal transduction from a receptor.

The term "autocrine cell", as used herein, refers to a cell which produces a substance which can stimulate a receptor located on or within the same cell as that which produces the substance. For example, wild-type yeast MATα and MATa cells are not autocrine. However, a yeast cell which produces both α-factor and α-factor receptor, or both a-factor and a-factor receptor, in functional form, is autocrine. By extension, cells which produce a peptide which is being screened for the ability to activate a receptor (e.g., by activating a G protein-coupled receptor) and also express the receptor are called "autocrine cells". In some instances, such cells can also be referred to as "putative autocrine cells" since some of the cells will express peptides from the library which will not activate the receptor which is expressed. In a library of such cells, in which a multitude of different peptides are produced, it is likely that one or more of the cells will be "autocrine" in the stricter sense of the term.

As used herein the term "chimeric" G protein subunit refers to a G protein subunit composed of at least two discrete polypeptides, a first polypeptide from a yeast G protein subunit and a second polypeptide from a heterologous G protein subunit. Each of the first and second polypeptides are encoded by a nucleic acid construct and are operatively linked such that upon expression of the construct, a functional chimeric G protein subunit is produced, i.e., a fusion protein comprising the first polypeptide linked to the second polypeptide. In preferred embodiment, the heterologous G protein subunit is mammalian. In particularly preferred embodiments, the heterologous G protein subunit is human. For example, chimeric G protein subunits of the present invention can comprise a polypeptide from GPA1 linked to Gα, STE18, linked to Gγ, or STE4, linked to Gβ. In preferred embodiments, in particular for chimeric Gα subunits, the portion of the chimeric subunit from yeast GPA1 comprises a portion of the amino terminus of GPA1 and is less than 330 amino acids in length. In particularly preferred embodiments, the portion of the chimeric subunit derived from GPA1 is about 40 amino acids. In another embodiment, the portion of the chimeric subunit derived from GPA1 is about 20 amino acids.

As used herein, the term "not produced in functional form" with regard to endogenous yeast proteins is intended to encompass proteins which are not produced in functional form for any number of reasons, for example, because of a mutation to the gene which encodes the protein or a deletion, e.g., a disruption, of the gene which encodes the protein. The term "not produced in functional form" is also intended to include conditional mutations(e.g. temperature sensitive mutation, wherein the protein is not produced in functional form under certain conditions.

As used herein, the terms used to indicate amino acid mutations, such as "S270P" and the like, represent the wild type amino acid residue (in standard one letter code), followed the amino acid position, followed by the substituted amino acid (in standard one letter code). Thus, S270P indicates substitution of the wild type serine at position 270 with proline. The terms such as "Gαs(S270P)" and the like represent the G protein having the indicated substitution. Thus, the term Gαs(S270P) represents a Gαs subunit having a proline substituted for the wild type serine at position 270.

II. General Overview of Assay

As set out above, the present invention relates to methods for identifying effectors of a receptor protein or receptor protein complex. The instant assays are characterized by the use of a mixture of recombinant yeast cells to sample test compounds for receptor agonists or antagonists. As described in greater detail below, the reagent cells express a heterologous GPCR protein functionally integrated into the cell and capable of transducing a detectable signal in the yeast cell. Exemplary GPCRs are discussed below. Compound which either agonize or antagonize the receptor function can be selected and then identified based on biochemical signals produced by the receptor, or any more distal result of receptor-mediated stimulation, for example increases in endogenous mRNA expression, etc., or, in some embodiments, by the use of reporter genes responsive to such signals. In certain embodiments, the library of compounds to be tested is a library of peptides which is expressed by the yeast cells and causes stimulation in an autocrine fashion.

The ability of compounds to modulate the signal transduction activity of the target receptor can be scored for by detecting up or down-regulation of the detection signal. For example, GTPase activity, phospholipid hydrolysis, or protein phosphorylation stimulated by the receptor can be measured directly. Alternatively, the use of a reporter gene can provide a readout. In any event, a statistically significant change in the detection signal can be used to facilitate isolation of compounds of interest of those cells from the mixture which contain a nucleic acid encoding a test polypeptide which is an effector of the target receptor.

In certain embodiments, the yeast cells for use in the instant assays express heterologous GPCR and an endogenous G protein subunit which couples to that receptor. Preferably, the yeast cells of the present invention have been modified such that coupling of the GPCR to the yeast pheromone signaling pathway is enhanced. For example, in preferred embodiments, the yeast cells express a heterologous GPCR and mutated endogenous G protein subunit which facilitates functional integration of that receptor into the yeast cell. In another preferred embodiment, the yeast cells express a heterologous GPCR and a heterologous G protein subunit. In particularly preferred embodiments, the heterologous GPCR and the heterologous G protein subunit are of the same origin, e.g., mammalian. In yet another preferred embodiment, the yeast cells express a mutated heterologous G protein subunit.

In still another preferred embodiment, the yeast cells express a chimeric G protein subunit. In particularly preferred embodiments the heterologous GPCR and the heterologous segment of the chimeric G protein subunit are derived from the same source. In more preferred embodiments, the second amino acid sequence in the G protein subunit chimera is derived from a mammalian G protein subunit. In particularly preferred embodiments, the second amino acid sequence is derived from a human G protein subunit sequence.

It will further be understood that the above embodiments are not mutually exclusive. For example, in certain preferred embodiments, a yeast cell may express a first mutated or chimeric G protein subunit and a second, different mutated or chimeric G protein subunit to enhance coupling to the heterologous receptor.

In certain embodiments the yeast cells also express an indicator gene that produces a detectable signal upon functional coupling of the heterologous G protein coupled receptor to the G protein. In certain embodiments the indicator gene is a reporter gene construct which including a reporter gene in operative linkage with one or more transcriptional regulatory elements responsive to the signal transduction activity of the target receptor, with the level of expression of the reporter gene providing the receptor-dependent detection signal. The amount of transcription from the reporter gene may be measured using any method known to those of skill in the art. For example, specific mRNA expression may be detected using Northern blots or specific protein product may be identified by a characteristic stain or an intrinsic activity. In preferred embodiments, the gene product of the reporter is detected by an intrinsic activity associated with that product. For instance, the reporter gene may encode a gene product that, by enzymatic activity, gives rise to a detection signal based on color, fluorescence, or luminescence.

The amount of activation of the indicator gene, e.g., expression of reporter gene, is then compared to the amount of expression in either the same cell in the absence of the test compound or it may be compared with the amount of transcription in a substantially identical cell that lacks the specific receptors. A control cell may be derived from the same cells from which the recombinant cell was prepared but which had not been modified by introduction of heterologous DNA, e.g., the encoding a test polypeptide. Alternatively, it may be a cell in which the specific receptors are removed. Any difference, e.g., a statistically significant difference, in the amount of transcription indicates that the test compound has in some manner altered the activity of the specific receptor.

In other preferred embodiments, the reporter gene provides a selection method such that cells in which the compound is an effector for the receptor have a growth advantage. For example the reporter could enhance cell viability, relieve a cell nutritional requirement, and/or provide resistance to a drug.

By using any one of these readouts, compounds which modulate signaling via the heterologous receptor can be selected. If the compound does not appear to modulate signaling via the receptor protein, the assay may be repeated and modified by the introduction of a step in which the recombinant cell is first contacted with a known activator of the target receptor to induce signal transduction from the receptor, and the compound is assayed for its ability to inhibit the activity of the receptor, e.g., to identify receptor antagonists. In yet other embodiments, compounds can be screened for members which potentiate the response to a known activator of the receptor.

III. Host Cells

The host cells of the present invention may be of any species of yeast which are cultivable and in which an exogenous receptor can be made to engage the appropriate signal transduction machinery of the host cell. Exemplary species include *Kluyverei lactis*, *Schizosaccharomyces pombe*, and *Ustilaqo maydis*, with *Saccharomyces cerevisiae* being preferred. Other yeast which can be used in practicing the present invention are *Neurospora crassa, Aspergillus niger, Aspergillus nidulans, Pichia pastoris, Candida tropicalis*, and *Hansenula polymorpha*. The term "yeast", as used herein, includes not only yeast in a strictly taxonomic sense, i.e., unicellular organisms, but also yeast-like multicellular fungi or filamentous fungi.

The choice of appropriate host cell will also be influenced by the choice of detection signal. For instance, reporter constructs, as described below, can provide a selectable or screenable trait upon transcriptional activation (or inactivation) in response to a signal transduction pathway coupled to the target receptor. The indicator gene may be an unmodified gene already in the host cell pathway, such as the genes responsible for growth arrest in yeast. In certain embodiments a host cell gene may be operably linked to a "receptor-responsive" promoter. Alternatively, it may be a heterologous gene that has been so linked. Suitable genes and promoters are discussed below.

To achieve optimal selection or screening, the host cell phenotype will be considered. For example, introducing a pheromone-responsive chimeric HIS3 gene into a yeast that has a wild-type HIS3 gene would frustrate genetic selection. Thus, to achieve nutritional selection, an auxotrophic strain is preferred. Yeast strains that are auxotrophic for histidine (HIS3) are known, see Struhl and Hill, (1987) *Mol. Cell. Biol.*, 7:104; Fasullo and Davis, *Mol. Cell. Biol.*, (1988) 8:4370. The HIS3 (imidazoleglycerol phosphate dehydratase) gene has been used as a selective marker in yeast. See Sikorski and Heiter, (1989) Genetics, 122:19; Struhl, et al., P.N.A.S. (1979) 76:1035; and, for FUS1-HIS3 fusions, see Stevenson, et al., (1992) *Genes Dev.*, 6:1293.

In certain embodiments, the host yeast cell can be modified in other ways. For example, it may be desirable to inactivate, such as by mutation or deletion, a homologous receptor, e.g., a pheromone receptor, present in the cell in order to minimize interference with signaling via the heterologous receptor. "Inactivation", with respect to genes of the host cell, means that production of a functional gene product is prevented or inhibited. Inactivation may be achieved by deletion of the gene, mutation of the promoter so that expression does not occur, or mutation of the coding sequence so that the gene product is inactive. Inactivation may be partial or total.

In a preferred embodiment of the subject assay, the yeast cells possess one or more of the following characteristics: (a) the endogenous FUS1 gene has been inactivated; (b) the endogenous SST2 gene, and/or other genes involved in desensitization, have been inactivated; (c) if there is a homologous, endogenous receptor gene it has been inactivated; and (d) if the yeast produces an endogenous ligand to the exogenous receptor, the genes encoding for the ligand been inactivated.

It is desirable that the exogenous receptor be exposed on a continuing basis to the peptides. In some instances, this may result in desensitization of the pheromone pathway to the stimulus. For example, the mating signal transduction pathway is known to become desensitized by several mechanisms including pheromone degradation and modification of the function of the receptor, G proteins and/or downstream elements of the pheromone signal transduction by the products of the SST2, STE50, AFR1 (Konopka, J. B. (1993) *Mol. Cell. Biol.* 13:6876–6888) and SGV1, MSG5, and SIG1 genes. Selected mutations in these genes can lead to hypersensitivity to pheromone and an inability to adapt to the presence of pheromone. For example, introduction of mutations that interfere with function into strains expressing heterologous G protein-coupled receptors constitutes a significant improvement on wild type strains and enables the development of extremely sensitive bioassays for compounds that interact with the receptors. Other mutations e.g. STE50, sgv1, bar1, ste2, ste3, pik1, msg5, sig1, and aft1, have the similar effect of increasing the sensitivity of the bioassay. Thus desensitization may be avoided by mutating (which may include deleting) the SST2 gene so that it no longer produces a functional protein, or by mutating one of the other genes listed above.

In certain embodiments, it will be desirable to complement the host yeast cells, e.g., least partial function of an inactivated gene of the host cell can be supplied by an exogenous nucleic acid. For instance, yeast cells can be "mammalianized", and even "humanized", by complementation of receptor and signal transduction proteins with mammalian homologues. To illustrate, inactivation of a yeast Byr2/Ste11 gene can be complemented by expression of a human MEKK gene.

Complementations for use in the subject assay can be constructed without any undue experimentation. Indeed, many yeast genetic complementations with mammalian signal transduction proteins have been described in the art. For example, Mosteller et al. (1994) Mol Cell Biol 14:1104–12 demonstrates that human Ras proteins can complement loss of ras mutations in *S. cerevisiae*. Moreover, Toda et al. (1986) Princess Takamatsu Symp 17: 253–60 have shown that human ras proteins can complement the loss of RAS1 and RAS2 proteins in yeast, and hence are functionally homologous. Both human and yeast RAS proteins can stimulate the magnesium and guanine nucleotide-dependent adenylate cyclase activity present in yeast membranes. Ballester et al. (1989) Cell 59: 681–6 describe a vector to express the mammalian GAP protein in the yeast *S. cerevisiae*. When expressed in yeast, GAP inhibits the function of the human ras protein, and complements the loss of IRA1. IRA1 is a yeast gene that encodes a protein with homology to GAP and acts upstream of RAS. Mammalian GAP can therefore function in yeast and interact with yeast RAS. Wei et al. (1994) Gene 151: 279–84 describes that a human Ras-specific guanine nucleotide-exchange factor, Cdc25GEF, can complement the loss of CDC25 function in *S. cerevisiae*. Martegani et al. (1992) EMBO J 11: 2151–7 describe the cloning by functional complementation of a mouse cDNA encoding a homolog of CDC25, a *Saccharomyces cerevisiae* RAS activator. Vojtek et al. (1993) J Cell Sci 105: 777–85 and Matviw et al. (1992) Mol Cell Biol 12: 5033–40 describe how a mouse CAP protein, e.g., an adenylyl cyclase associated protein associated with ras-mediated signal transduction, can complements defects in *S. cerevisiae*. Papasavvas et al. (1992) Biochem Biophys Res Commun 184:1378–85 also suggest that inactivated yeast adenyl cyclase can be complemented by a mammalian adenyl cyclase gene. Hughes et al. (1993) Nature 364: 349–52 describe the complementation of byr1 in fission yeast by mammalian MAP kinase kinase (MEK). Parissenti et al. (1993) Mol Cell Endocrinol 98: 9–16 describes the reconstitution of bovine protein kinase C (PKC) in yeast. The Ca(2+) and phospholipid-dependent Ser/Thr kinase PKC plays important roles in the transduction of cellular signals in mammalian cells. Marcus et al. (1995) PNAS 92: 6180–4 suggests the complementation of shk1 null mutations in *S. pombe* by the either the structurally related *S. cerevisiae* Ste20 or mammalian p65PAK protein kinases.

IV Expression Systems

In general, it will be desirable that an expression vector be capable of replication in the host cell. Heterologous DNA may be integrated into the host genome, and thereafter is replicated as a part of the chromosomal DNA, or it may be DNA which replicates autonomously, as in the case of a plasmid. In the latter case, the vector will include an origin of replication which is functional in the host. In the case of an integrating vector, the vector may include sequences which facilitate integration, e.g., sequences homologous to host sequences, or encoding integrases.

Appropriate cloning and expression vectors for use with bacterial, fungal, yeast, and mammalian cellular hosts are known in the art, and are described in, for example, Powels et al. (*Cloning Vectors: A Laboratory Manual*, Elsevier, New York, 1985). Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. Suitable promoters for function in yeast include the promoters for metallothionein, 3-phosphoglycerate kinase (Hitzeman et al., *J. Biol. Chem.* 255, 2073 (1980) or other glycolytic enzymes(Hess et al., *J. Adv. Enzyme Req.* 7, 149 (1968); and Holland et al. *Biochemistry* 17, 4900 (1978)), such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phospho-glucose isomerase, and glucokinase. Suitable vectors and promoters for use in yeast expression are further described in R. Hitzeman et al., EPO Publn. No. 73,657. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. Finally, promoters that are active in only one of the two haploid mating types may be appropriate in certain circumstances. Among these haploid-specific promoters, the pheromone promoters MFa1 and MFα1 are of particular interest.

V. Receptors

Numerous different receptor types can be expressed in yeast cells for use in the instant invention.

The "heterologous receptors" of the present invention may be any G protein-coupled receptor which is exogenous to the cell which is to be genetically engineered for the purpose of the present invention. This receptor may be, for example, a plant or animal cell receptor. Screening for binding to plant cell receptors may be useful in the development of, e.g., herbicides. In the case of an animal receptor, it may be of invertebrate or vertebrate origin. An invertebrate receptor would, for example, facilitate development of insecticides. The expression of a receptor from a different species of yeast is also included within the term "heterologous" and could be used in the development of fungicides. The receptor may also be a vertebrate, more preferably a mammalian, still more preferably a human, receptor. The exogenous receptor is also preferably a seven transmembrane segment receptor.

Known ligands for GPCRs include: purines and nucleotides, such as adenosine, cAMP, ATP, UTP, ADP, melatonin and the like; biogenic amines(and related natural ligands), such as 5-hydroxytryptamine, acetylcholine, dopamine, adrenaline, adrenaline, adrenaline, histamine, noradrenaline, noradrenaline, noradrenaline, tyramine/octopamine and other related compounds; peptides such as adrenocorticotrophic hormone (acth), melanocyte stimulating hormone (msh), melanocortins, neurotensin (nt), bombesin and related peptides, endothelins, cholecystokinin, gastrin, neurokinin b (nk3), invertebrate tachykinin-like peptides, substance k (nk2), substance p (nk1), neuropeptide y (npy), thyrotropin releasing-factor (trf), bradykinin, angiotensin ii, beta-endorphin, c5a anaphalatoxin, calcitonin, chemokines (also called intercrines), corticotrophic releasing factor (crf), dynorphin, endorphin, fmlp and other formylated peptides, follitropin (fsh), fungal mating pheromones, galanin, gastric inhibitory polypeptide receptor (gip), glucagon-like peptides(glps), glucagon, gonadotropin releasing hormone (gnrh), growth hormone releasing hormone(ghrh), insect diuretic hormone, interleukin-8, leutropin (lh/hcg), met-enkephalin, opioid peptides, oxytocin, parathyroid hormone (pth) and pthrp, pituitary adenylyl cyclase activating peptide (pacap), secretin, somatostatin, thrombin, thyrotropin (tsh), vasoactive intestinal peptide (vip), vasopressin, vasotocin; eicosanoids such as ip-prostacyclin, pg-prostaglandins, tx-thromboxanes; retinal based compounds such as vertebrate 11-cis retinal, invertebrate 11-cis retinal and other related compounds; lipids and lipid-based compounds such as cannabinoids, anandamide, lysophosphatidic acid, platelet activating factor, leukotrienes and the like; excitatory amino acids and ions such as calcium ions and glutamate.

Preferred G protein coupled receptors include: α1A-adrenergic receptor, α1B-adrenergic receptor, α2-adrenergic receptor, α2B-adrenergic receptor, β1-adrenergic receptor, β2-adrenergic receptor, β3-adrenergic receptor, m1 acetylcholine receptor (AChR), m2 AChR, m3 AChR, m4 AChR, m5 AChR, D1 dopamine receptor, D2 dopamine receptor, D3 dopamine receptor, D4 dopamine receptor, D5 dopamine receptor, A1 adenosine receptor, A2b adenosine receptor, 5-HT1a receptor, 5-HT1b receptor, 5HT1-like receptor, 5-HT1d receptor, 5HT1d-like receptor, 5HT1d beta receptor, substance K (neurokinin A) receptor, fMLP receptor, fMLP-like receptor, angiotensin II type 1 receptor, endothelin ETA receptor, endothelin ETB receptor, thrombin receptor, growth hormone-releasing hormone (GHRH) receptor, vasoactive intestinal peptide receptor, oxytocin receptor, somatostatin SSTR1 and SSTR2, SSTR3, cannabinoid receptor, follicle stimulating hormone (FSH) receptor, leutropin (LH/HCG) receptor, thyroid stimulating hormone (TSH) receptor, thromboxane A2 receptor, platelet-activating factor (PAF) receptor, C5a anaphylatoxin receptor, Interleukin 8 (IL-8) IL-8RA, IL-8RB, Delta Opioid receptor, Kappa Opioid receptor, mip-1/RANTES receptor, Rhodopsin, Red opsin, Green opsin, Blue opsin, metabotropic glutamate mGluR1–6, histamine H2 receptor, ATP receptor, neuropeptide Y receptor, amyloid protein precursor receptor, insulin-like growth factor II receptor, bradykinin receptor, gonadotropin-releasing hormone receptor, cholecystokinin receptor, melanocyte stimulating hormone receptor, antidiuretic hormone receptor, glucagon receptor, and adrenocorticotropic hormone II receptor.

Other suitable receptors are known in the art. The term "receptor," as used herein, encompasses both naturally occurring and mutant receptors.

Many of these G protein-coupled receptors, like the yeast a- and α-factor receptors, contain seven hydrophobic amino acid-rich regions which are assumed to lie within the plasma membrane. Thus, for expression in yeast, the gene could be operably linked to a promoter functional in the cell to be engineered and to a signal sequence that also functions in the cell. For example, suitable promoters include Ste2, Ste3 and gal10. Optionally, the codons of the gene would be optimized for expression in yeast. See Hoekema et al., (1987) *Mol. Cell. Biol.*, 7:2914–24; Sharp, et al., (1986) 14:512–543.

In some instances a foreign receptor which is expressed in yeast will functionally integrate into the yeast membrane, and there interact with the endogenous yeast G protein. In other instances, either the receptor may be modified or a compatible G protein or a chimeric (i.e., part yeast/part mammalian) G protein subunit which can properly interact with the exogenous receptor G protein may be provided. The homology of STRs is discussed in Dohlman et al., *Ann. Rev. Biochem.*, (1991)60:653–88. When STRs are compared, a distinct spatial pattern of homology is discernible. The transmembrane domains are often the most similar, whereas the N- and C-terminal regions, and the cytoplasmic loop connecting transmembrane segments V and VI are more divergent. The functional significance of different STR regions has been studied by introducing point mutations (both substitutions and deletions) and by constructing chimeras of different but related STRs. Synthetic peptides corresponding to individual segments have also been tested for activity. Affinity labeling has been used to identify ligand binding sites. Such information can be useful in creating mutations in GPCRs to enhance functionality.

If a naturally occurring exogenous GPCR cannot be made functional in yeast, it may be mutated for this purpose. A comparison would be made of the amino acid sequences of the exogenous receptor and of the yeast receptors, and regions of high and low homology identified. Trial mutations would then be made to distinguish regions involved in ligand or G protein binding, from those necessary for functional integration in the membrane. The exogenous receptor would then be mutated in the latter region to more closely resemble the yeast receptor, until functional integration was achieved. If this were insufficient to achieve functionality, mutations would next be made in the regions involved in G protein binding.

Preferably, the yeast genome is modified so that it is unable to produce the yeast receptors which are homologous to the exogenous receptors in functional form in order to facilitate assay interpretation. For example, the endogenous G protein or G protein subunit is mutated generating, for example, a temperature sensitive mutant.

A common technique which has been used for cloning receptors is by nucleic acid hybridization technology to identify receptors which are homologous to other, known receptors. For instance, the cloning of a receptor can be accomplished by the isolation and sequencing of the corresponding protein or the use of expression cloning techniques based on sequence homologies between these receptors. This technology, since it does not require previous knowledge of the ligand for the receptor, has resulted in the cloning of a large number of "orphan receptors", which have no known ligand and often whose biological function is obscure.

Many orphan receptors are GPCRs, but receptors of all types comprise this large family. Known orphan receptors include the nuclear receptors COUP-TF1/EAR3, COUP-TF2/ARP1, EAR-1, EAR-2, TR-2, PPAR1, HNF-4, ERR-1, ERR-2, NGFIB/Nur77, ELP/SF-1 and MPL (Parker et al, supra, and Power et al. (1992) TIBS 13:318–323). A large number of orphan receptors have been identified in the EPH family (Hirai et al (1987) *Science* 238:1717–1720). HER3 and HER4 are orphan receptors in the epidermal growth factor receptor family (Plowman et al. (1993) *Proc. Natl. Acad. Sci. USA* 90:1746–1750). ILA is a newly identified member of the human nerve growth factor/tumor necrosis factor receptor family (Schwarz et al. (1993) *Gene* 134:295–298). IRRR is an orphan insulin receptor-related receptor which is a transmembrane tyrosine kinase (Shier et al. (1989) *J. Biol Chem* 264:14606–14608). Several orphan tyrosine kinase receptors have been found in Drosophila (Perrimon (1994) *Curr. Opin. Cell Biol.* 6:260–266).

In one aspect, the present invention provides for novel assays which have been optimized for testing for agonists and antagonists of GPCRs, in particular orphan GPCRs. These assays involve the use of four different strains of yeast, each of which has been engineered to contain a different complement of G protein subunits. This expression of various combinations of G protein subunits increases the likelihood of obtaining functional coupling even absent knowing which G protein subunit chimera (or combination of subunits) will best function in the screening assay. The importance of identifying ligands for orphan receptors is clear; it opens up a wide area for research in the area of drug discovery.

VI. G protein Subunits and Complexes

In certain instances it will be desirable to modify naturally occurring forms of yeast or mammalian G-protein subunits. For instance, where a heterologous GPCR does not adequately couple to the endogenous yeast G protein subunit, such a subunit, e.g., GPA1 may be modified to improve coupling. Such modifications can be made by mutation, e.g., directed mutation or random mutation, using methods known in the art and described in more detail below.

Alternatively, a heterologous subunit can be expressed. The specificity of coupling of a receptor to a heterotrimeric G-protein is largely determined by the at subunit of the G-protein. Thus, in preferred embodiments, a heterologous Gα subunit is expressed in the yeast cell. The predominant role of the yeast Gα, GPA1, is to bind to and sequester the effector-signaling βγ component of the heterotrimer. Thus, in order to achieve functional integration into a yeast pheromone signaling pathway, a heterologous Gα subunit must bind to yeast βγ in the quiescent state, and release it upon receptor activation.

If functional integration is not achieved, or is not optimal, the heterologous subunit can be mutated. For example, in general, mammalian Gα subunits couple poorly to the βγ subunits of yeast cells. In yeast which lack their own endogenous Gα subunit, this failure to couple results in the constitutive activation of the pheromone pathway due to the effector activity of the unbound yeast βγ. Accordingly, if a naturally occurring heterologous G protein subunit does not enhance coupling, modifications can be made. Such modifications may take the form of mutations which are designed to increase the resemblance of the G protein subunit to the yeast G protein subunit while decreasing its resemblance to the heterologous receptor-associated G protein subunit.

For example, a residue may be changed so as to become identical to the corresponding yeast G protein residue, or to belong to the same exchange group of that residue. After modification, the modified G protein subunit might or might not be "substantially homologous" to the heterologous and/or the yeast G protein subunit.

In the case of Gα, modifications are preferably concentrated in regions of the Gα which are likely to be involved in Gβγ binding.

In other embodiments, modifications will take the form of replacing one or more amino acids of the receptor-associated G protein subunit with the corresponding yeast G protein subunit amino acids, thereby forming a chimeric G protein subunit. In preferred embodiments, three or more consecutive amino acids are replaced. In other embodiments, point mutations may be sufficient.

Chimeric G protein subunits of the invention enhance coupling of the heterologous receptor to the endogenous yeast signaling pathway. For example, a chimeric Gα subunit will interact with the heterologous receptor and the yeast Gβγ complex, thereby permitting signal transduction.

A yeast cell of the present invention can express one or more of the indicated G protein structures, For example, a yeast cell can express a chimeric Gα subunit, and an endogenous yeast Gβγ, a mammalian Gβγ, a mutated mammalian Gβγ, or a chimeric Gαγ.

In preferred embodiments, both the receptor and the heterologous subunit are derived from the same source, e.g., are mammalian. In particularly preferred embodiment, both are human in origin.

In another preferred embodiment, a yeast cell that expresses a heterologous or chimeric G protein subunit has been modified such that the endogenous, homologous G protein subunit gene is disrupted.

In certain embodiments, yeast strains lacking pheromone receptors and having no heterologous receptor capable of coupling to the pheromone response pathway may be used to assess the affinity of an endogenous yeast G protein subunit, a mutated G protein subunit, or chimeric G protein subunit for other yeast subunits. For example, the affinity of gpa1 p, chimeric gpa-Gα s, or other Gα subunit for yeast βγ or other chimeric βγ subunit can be assessed. Such strains depend on free βγ for signaling through the pheromone response pathway leading to growth arrest. Mutant Gα subunits may be tested in such a system, those which bind Bγ more effectively will sequester βγ and reduce or block signaling. Preferably, such chimeras and gpa1 subunits can be assessed in a gpa1⁻ background to avoid competition with gpa1 for βγ. For example, Gα s chimeric mutants(see below) carrying D229S, E10K, N254D, or S286P were found to sequester bg more effectively than the chimerae with wild type sequences. Also, double mutants were even more effective than either single mutant. Similarly, overexpression of Gαs by driving transcription from the highly efficient PGK promoter resulted in dampening of the receptor coupling which may be offset by introduction of the double mutant Gαs (D229S,E10K).

Guidance for making mutations in G protein subunits and in the construction of chimeric G protein subunits is provided below.

Site-Directed Mutagenesis Versus Random Mutagenesis

There are numerous art recognized ways to solve the structure-function problems of the sort presented by attempts to define the determinants involved in mediating the association of the subunits that comprise the G protein heterotrimer. For example, in one approach, discussed above with respect to hybrid constructs, specific mutations or alterations are introduced into a molecule based upon the available experimental evidence. In a second approach, random mutagenesis techniques, coupled with selection or screening systems, are used to introduce large numbers of mutations into a molecule, and that collection of randomly mutated molecules is then subjected to a selection for the desired phenotype or a screen in which the desired phenotype can be observed against a background of undesirable phenotypes.

With random mutagenesis one can mutagenize an entire molecule or one can proceed by cassette mutagenesis. In the former instance, the entire coding region of a molecule is mutagenized by one of several methods(chemical, PCR, doped oligonucleotide synthesis) and that collection of randomly mutated molecules is subjected to selection or screening procedures. Random mutagenesis can be applied in this way in cases where the molecule being studied is relatively small and there are powerful and stringent selections or screens available to discriminate between the different classes of mutant phenotypes that will inevitably arise. In the second approach, discrete regions of a protein, corresponding either to defined structural (i.e. α-helices, β-sheets, turns, surface loops) or functional determinants (e.g., catalytic clefts, binding determinants, transmembrane segments) are subjected to saturating or semi-random mutagenesis and these mutagenized cassettes are re-introduced into the context of the otherwise wild type allele.

Cassette mutagenesis is most useful when there is experimental evidence available to suggest a particular function for a region of a molecule and there is a powerful selection and/or screening approach available to discriminate between interesting and uninteresting mutants. Cassette mutagenesis is also useful when the parent molecule is comparatively large and the desire is to map the functional domains of a molecule by mutagenizing the molecule in a step-wise fashion, i.e. mutating one linear cassette of residues at a time and then assaying for function.

The present invention provides for applying random mutagenesis in order to further delineate the determinants involved in Gα-Gβγ or subunit-receptor association. Random mutagenesis may be accomplished by many means, including:

1. PCR mutagenesis, in which the error prone Taq polymerase is exploited to generate mutant alleles of G protein subunits, which are assayed directly in yeast for an ability to couple.
2. Chemical mutagenesis, in which expression cassettes encoding G protein subunits are exposed to mutagens and the protein products of the mutant sequences are assayed directly in yeast for an ability to couple.
3. Doped synthesis of oligonucleotides encoding portions of the G protein subunit gene.
4. In vivo mutagenesis, in which random mutations are introduced into the coding region of G protein subunits by passage through a mutator strain of *E. coli*, XL1-Red (mutD5 mutS mutT) (Stratagene, Menasa, Wis).

In certain embodiments, for example, the random mutagenesis may be focused on regions suspected to be involved in Gα-Gβγ association. Random mutagenesis approaches are feasible for two reasons. First, in yeast one has the ability to construct stringent screens and facile selections (growth vs. death, transcription vs. lack of transcription) that are not readily available in mammalian systems. Second, when using yeast it is possible to screen efficiently through thousands of transformants rapidly. For example, this relatively small region of Gα subunits represents a reasonable target for cassette mutagenesis. Another region that may be amenable to cassette mutagenesis is that defining the surface of the switch region of Gα subunits that is solvent-exposed in the crystal structures of Gαi and transducin. From the data described below, this surface may contain residues that are in direct contact with yeast Gβγ subunits, and may therefore be a reasonable target for mutagenesis.

A. Modification of Gα

Some aspects of Gα structure are relevant to the design of modified Gα subunits. Alignments of Gα and GPA1 can be made to determine sequence similarity. For alignments of the entire coding regions of GPA1 with Gαs, Gαi, and GαO, Gαq and Gαz, see Dietzel and Kurjan (1987, *Cell* 50:573) and Lambright, et al. (1994, *Nature* 369:621–628). Additional sequence information is provided by Mattera, et al. (1986, *FEBS Lett* 206:36–41), Bray, et al. (1986, *Proc. Natl. Acad. Sci USA* 83:8893–8897) and Bray, et al. (1987, *Proc Natl. Acad Sci USA* 84:5115–5119). An alignment of GPA1 and four other Gα proteins is provided by Stone and Reed (1990. *Mol. Cell Biol.* 10:4439). See also the alignment presented in FIG 1.

The gene encoding a G protein homolog of *S. cerevisiae* was cloned independently by Dietzel and Kudjan (supra) (who referred to the gene as SCG1) and by Nakafuku, et al. (1987 *Proc Natl Acad Sci* 84:2140–2144) (who called the gene GPA1). Sequence analysis revealed a high degree of homology between the protein encoded by this gene and mammalian Gα. GPA1 encodes a protein of 472 amino acids, as compared with approximately 340–350 amino acids for most mammalian Gα subunits in four described families, Gαs, Gαi, Gαq and Gα12/13. Nevertheless, GPA1 shares overall sequence and structural homology with all Gα proteins identified to date. The highest overall homology in GPA1 is to the Gαi family (48% identity, or 65% with conservative substitutions) and the lowest is to Gαs (33% identity, or 51% with conservative substitutions) (Nakafuku, et al., supra).

The regions of high sequence homology among Gα subunits are dispersed throughout their primary sequences, with the regions sharing the highest degree of homology mapping to sequence that comprises the guanine nucleotide binding/GTPase domain. This domain is structurally similar to the αβ fold of ras proteins and the protein synthesis elongation factor EF-Tu. This highly conserved guanine nucleotide-binding domain consists of a six-stranded β sheet surrounded by a set of five α-helices. It is within these β sheets and α helices that the highest degree of conservation is observed among all Gα proteins, including GPA1. The least sequence and structural homology is found in the intervening loops between the β sheets and α helices that define the core GTPase domain. There are a total of four "intervening loops" or "inserts" present in all Gα subunits. In the crystal structures reported to date for the GDP-and GTPγS-liganded forms of bovine rod transducin (Noel, et al. (1993) *Nature* 366:654–663); (Lambright, et al. (1994) *Nature* 369:621–628), the loop residues are found to be outside the core GTPase structure. Functional roles for these loop structures have been established in only a few instances. A direct role in coupling to phosphodiesterase-γ has been demonstrated for residues within inserts 3 and 4 of Gαt (Rarick, et al. (1992) *Science* 10 256:1031–1033); (Artemyev, et al. (1992)*J. Biol. Chem.* 267:25067–25072), while a "GAP-like" activity has been ascribed to the largely α-helical insert 1 domain of GαS (Markby, et al. (1993) *Science* 262:1805–1901).

While the amino- and carboxy-termini of Gα subunits do not share striking homology either at the primary, secondary, or tertiary levels, there are several generalizations that can be made about them. First, the amino termini of Gα subunits have been implicated in the association of Gα with Gβγ complexes and in membrane association via N-terminal myristoylation. In addition, the carboxy-termini have been implicated in the association of Gαβγ heterotrimeric complexes with G protein-coupled receptors (Sullivan, et al. (1987) *Nature* 330:758–760); West, et al. (1985) *J. Biol. Chem.* 260:14428–14430); (Conklin, et al. (1993) *Nature* 363:274–276); (Kallal and Kurjan. 1997. *Mol. Cell. Biol.* 17:2897). Data in support of these generalizations about the function of the N-terminus derive from several sources, including both biochemical and genetic studies.

FIG. 1 shows the amino terminal 66 residues of GPA1 aligned with the cognate domains of human Gαs, Gαi2, Gαi3, Gα16 and transducin. In the GPA41Gα hybrids, the amino terminal 41 residues (derived from GPA1) are identical and end with the sequence-LEKQRDKNE-(SEQ ID NO:79). All residues following the glutamate (E) residue at position 41 are contributed by the human Gα subunits, including the consensus nucleotide binding motif shown in the amino acid sequence -GxGxxG-(SEQ ID NO:80). Periods in the sequences indicate gaps that have been introduced to maximize alignments in this region. Codon bias is mammalian. For alignments of the entire coding regions of GPA1 with Gαs , Gαi, and GαO, Gαq and Gαz, see Dietzel and Kudjan (1987, *Cell* 50:573) and Lambright, et al. (1994, *Nature* 369:621–628). Additional sequence information is provided by Mattera, et al. (1986, *FEBS Lett* 206:36–41), Bray, et al. (1986, *Proc. Natl. Acad. Sci USA* 83:8893–8897) and Bray, et al. (1987, *Proc Natl. Acad Sci USA* 84:5115–5119).

As indicated above, there is little if any sequence homology shared among the amino termini of Gα subunits. The amino terminal domains of Gα subunits that precede the first β-sheet (containing the sequence motif-LLLLGAGESG-(SEQ ID NO:81); see Noel, et al. (supra) for the numbering of the structural elements of Gα subunits) vary in length from 41 amino acids(GPA1) to 31 amino acids (Gαt). Most Gα subunits share the consensus sequence for the addition of myristic acid at their amino termini (MGXaaS-) (SEQ ID NO:82), although not all Gα subunits that contain this motif have myristic acid covalently associated with the glycine at position 2 (Speigel, et al. (1991) *TIBS* 16:338–3441). The role of this post-translational modification has been inferred from studies in which the activity of mutant Gα subunits from which the consensus sequence for myristoylation has been added or deleted has been assayed (Mumby et al. (1990) *Proc. Natl. Acad. Sci. USA* 87: 728–732; (Linder, et al. (1991) *J. Biol Chem.* 266:4654–4659); Gallego, et al. (1992) *Proc. Natl. Acad. Sci. USA* 89:9695–9699). These studies suggest two roles for N-terminal myristoylation. First, the presence of amino-terminal myristic acid has in some cases been shown to be required for association of Gα subunits with the membrane, and second, this modification has been demonstrated to play a role in modulating the association of Gα subunits with Gβγ complexes. The role of myristoylation of the GPA1 gene products, at present is unknown.

In other biochemical studies aimed at examining the role of the amino-terminus of Gα in driving the association between Gα and Gβγ subunits, proteolytically or genetically truncated versions of Gα subunits were assayed for their ability to associate with Gβγ complexes, bind guanine nucleotides and/or to activate effector molecules. In all cases, Gα subunits with truncated amino termini were deficient in all three functions (Graf, et al. (1992) *J. Biol. Chem.* 267:24307–24314); (Journot, et al. (1990) *J. Biol. Chem.* 265:9009–9015); and (Neer, et al. (1988) *J. Biol. Chem* 263:8996–9000). Slepak, et al. (1993, *J. Biol. Chem.* 268:1414–1423) reported a mutational analysis of the N-terminal 56 a.a. of mammalian Gαo expressed in *Escherichia coli*. Molecules with an apparent reduced ability to interact with exogenously added mammalian Gβγ were identified in the mutant library. As the authors pointed out, however, the assay used to screen the mutants the extent of ADP-ribosylation of the mutant Gα by pertussis toxin was not a completely satisfactory probe of interactions between Gα and Gβγ. Mutations identified as inhibiting the interaction of the subunits, using this assay, may still permit the complexing of Gα and Gβγ while sterically hindering the ribosylation of Gα by toxin. Other work has revealed specific amino acid residues of GPA1 that are important in GPA1 function. For example, a E307K mutation appears to create an a subunit with a broadened specificity for Gβ subunits (Whiteway et al. 1994. Mol. Cell. Biol. 14:3223). Interestingly, the residue in the mammalian G α subunit which is equivalent to the E307 position is diagnostic for a particular class of mammalian a subunits. For example, the $G_s\alpha$ subunits contain a lysine at this position, the $G_o$ and $G_i$ α subunits contain a histidine, the transducin α subunits have a glutimine, the Gqα subunits have a proline, and the $G_{13}$ a subunits have an aspartic acid at this site (Whiteway et al. supra).

Genetic studies examined the role of amino-terminal determinants of Gα in heterotrimer subunit association have been carried out in both yeast systems using GPA1-mammalian Gα hybrids(Kang, et al. (1990) *Mol. Cell. Biol.* 10:2582–2590) and in mammalian systems using Gαi/Gαs hybrids(Russell and Johnson (1993) *Mol. Pharmacol.* 44:255–263). In the former studies, gene fusions, composed of yeast GPA1 and mammalian Gα sequences were constructed by Kang, et al. (supra) and assayed for their ability to complement a gpa1 null phenotype (i.e., constitutive activation of the pheromone response pathway) in *S. cerevisiae*. Kang, et al. demonstrated that wild type mammalian Gαs, Gαi but not Gαo proteins are competent to associate with yeast Gα and suppress the gpa1 null phenotype, but only when overexpressed. Fusion proteins containing the amino-terminal 330 residues of GPA1 sequence linked to 160, 143, or 142 residues of the mammalian Gαs, Gαi and Gαo carboxyl-terminal regions, respectively, also coupled to the yeast mating response pathway when overexpressed on high copy plasmids with strong inducible (CUP) or constitutive (PGK) promoters. All three of these hybrid molecules were able to complement the gpa1 null mutation in a growth arrest assay, and were additionally able to inhibit α-factor responsiveness and mating in tester strains. These last two observations argue that hybrid yeast-mammalian Gα subunits are capable of interacting directly with yeast Gβγ, thereby disrupting the normal function of the yeast heterotrimer. Fusions containing the amino terminal domain of Gαs, Gαi or Gαo, however, did not complement the gpa1 null phenotype, indicating a requirement for determinants in the amino terminal 330 amino acid residues of GPA1 for association and sequestration of yeast Gβγ complexes. Taken together, these data suggest that determinants in the amino terminal region of Gα subunits determine not only the ability to associate with Gβγ subunits in general, but also with specific Gβγ subunits in a species-restricted manner.

Hybrid Gαi/Gαs subunits have been assayed in mammalian expression systems (Russell and Johnson (supra). In these studies, a large number of chimeric Gα subunits were assayed for an ability to activate adenylyl cyclase, and therefore, indirectly, for an ability to interact with Gβγ (i.e., coupling of Gα to Gβγ=inactive cyclase; uncoupling of Gα from Gβγ=active cyclase). From these studies a complex picture emerged in which determinants in the region between residues 25 and 96 of the hybrids were found to determine the state of activation of these alleles as reflected in their rates of guanine nucleotide exchange and GTP hydrolysis and the extent to which they activated adenylyl cyclase in vivo. These data could be interpreted to support the hypothesis that structural elements in the region between the amino terminal methionine and the β sheet identified in the crystal structure of Gαt (see Noel, et al. supra and Lambright, et al. supra) are involved in determining the state of activity of the heterotrimer by (1) driving association/dissociation between Gαand Gβγ subunits; (2) driving GDP/GTP exchange. While there is no direct evidence provided by these studies to support the idea that residues in this region of Gα and residues in Gβγ subunits contact one another, the data nonetheless provide a positive indication for the construction of hybrid Gα subunits that retain function. There is, however, a negative indicator that derives from this work in that some hybrid constructs resulted in constitutive activation of the chimeric proteins (i.e., a loss of receptor-dependent stimulation of Gβγ dissociation and effector activation).

B. Construction of Chimeric Gα Subunits.

In preferred embodiments chimeric Gα subunits retain as much of the sequence of the native mammalian proteins as possible and, in particularly preferred embodiments, the level of expression for the heterologous components should approach, as closely as possible, the level of their endogenous counterparts. The results described by King, et al. (1990, Science 250:121–123) for expression of the human β2-adrenergic receptor and Gαs in yeast, taken together with negative results obtained by Kang, et al. (supra) with full-length mammalian Gα subunits other than Gαs, led to the following preferred embodiments for the development of yeast strains in which mammalian G protein-coupled receptors could be linked to the pheromone response pathway.

In one embodiment, mammalian Gα subunits are expressed using the native sequence of each subunit or, alternatively, as minimal gene fusions with sequences from the amino-terminus of GPA1 replacing the homologous residues from the mammalian Gα subunits. In another embodiment, mammalian Gα subunits are expressed from the GPA1 promoter either on low copy plasmids or after integration into the yeast genome as a single copy gene. In certain embodiments, endogenous Gβγ subunits are provided by the yeast STE4 and STE18 loci, while in other embodiments chimeric or heterologous Gβ and/or Gγ subunits are also provided.

C. Rational Design of Chimeric Gα Subunits

Several classes of rationally designed GPA1-mammalian Gα hybrid subunits have been tested for the ability to couple to yeast βγ. The first, and largest, class of hybrids are those that encode different lengths of the GPA1 amino terminal domain in place of the homologous regions of the mammalian Gα subunits. This class of hybrid molecules includes $GPA_{BAMH1}$, $GPA_{41}$, $GPA_{ID}$, and $GPA_{LW}$ hybrids, described below. The rationale for constructing these hybrid Gα proteins is based on results, described above, that bear on the importance of the amino terminal residues of Gα in mediating interaction with Gβγ.

Preferably, the yeast Gα subunit is replaced by a chimeric Gα subunit in which a portion, e.g., at least about 20, more preferably at least about 40, amino acids, from the amino terminus of the yeast Gα, is fused to a sequence from a mammalian (or other exogenous) Gα. While about 40 amino acids is the suggested starting point, shorter or longer portions may be tested to determine the minimum length required for coupling to yeast Gβγ and the maximum length compatible with retention of coupling to the exogenous receptor. It is presently believed that only the final 10 or 20 amino acids at the carboxy terminus of the Gα subunit are required for interaction with the receptor.

i. GPA$_{BAMH1}$ Hybrids.

Kang et al. supra. described hybrid G α subunits encoding the amino terminal 310 residues of GPA1 fused to the carboxyl terminal 160, 143 and 142 residues, respectively, of GαS, Gαi2, and Gαo . In all cases examined by Kang et al., the hybrid proteins were able to complement the growth arrest phenotype of gpa1 strains. Hybrids between GPA1 and Gαi3, Gαq and Gα16 have been constructed and functionally complement the growth arrest phenotype of gpa1 strains.

GPA41 hybrids. The rationale for constructing a minimal hybrid encoding only 41 amino acids of GPA1 relies upon the biochemical evidence for the role of the amino-terminus of Gα subunits discussed above, together with the following observation. G β and Gγ subunits are known to interact via α-helical domains at their respective amino-termini (Pronin, et al. (1992) *Proc. Natl. Acad. Sci. USA* 89:6220–6224); Garritsen, et al.1993). The suggestion that the amino termini of Gα subunits may form an helical coil and that this helical coil may be involved in association of Gα with Gαγ (Masters et al (1986) *Protein Engineering* 1:47–54); Lupas et al.(1992) *FEBS Lett.* 314:105–108) leads to the hypothesis that the three subunits of the G-protein heterotrimer interact with one another reversibly through the winding and unwinding of their amino-terminal helical regions. A mechanism of this type has been suggested, as well, from an analysis of leucine zipper mutants of the GCN4 transcription factor (Harbury, et al. (1993) *Science* 262:1401–1407). The rationale for constructing hybrids like those described by Kang, et al. supra., that contain a majority of yeast sequence and only minimal mammalian sequence, derives from their ability to function in assays of coupling between Gα and Gβγ subunits. However, these chimeras had never been assayed for an ability to couple to both mammalian G protein-coupled receptors and yeast Gβγ subunits, and hence to reconstitute a hybrid signaling pathway in yeast.

GPA$_{41}$ hybrids that have been constructed and tested include Gαs, Gαi2, Gαi3, Gαq, Gαo$_a$, Gαo$_b$ and Gα16. Hybrids of Gαs, Gαi2, Gαi3, and Gα16 functionally complement the growth arrest phenotype of gpa1 strains, while GPA$_{41}$ hybrids of Gαo$_a$ and Gαo$_b$ do not. In addition to being tested in a growth arrest assay, these constructs have been assayed in the more sensitive transcriptional assay for activation of a fus1p-HIS3 gene. In both of these assays, the GPA$_{41}$-Gαs hybrid couples less well than the GPA$_{41}$-i2, -i3, and -16 hybrids, while the GPA$_{41}$-o$_a$, and -o$_b$ hyrids do not function in either assay.

Several predictive algorithms indicate that the amino terminal domain up to the highly conserved sequence motif- LLLLGAGESG-(SEQ ID NO: 1) (the first L in this motif is residue 43 in GPA1) forms a helical structure with amphipathic character. Assuming that a heptahelical repeat unit, the following hybrids between yeast GPA1 and mammalian GαS can be used to define the number of helical repeats in this motif necessary for hybrid function:

GPA1–7/Gαs8–394
GPA1–14/Gαs15–394
GPA1–21/Gαs22–394
GPA1–28/Gαs29–394
GPA1–35/Gαs36–394
GPA1–42/Gαs43–394

In these hybrids, the prediction is that the structural repeat unit in the amino terminal domain up to the tetra-leucine motif is 7, and that swapping sequences in units of 7 will in effect amount to a swap of unit turns of turns of the helical structure that comprises this domain.

A second group of "double crossover" hybrids of this class are those that are aligned on the first putative heptad repeat beginning with residue G11 in GPA1. In these hybrids, helical repeats are swapped from GPA1 into a GαS backbone one heptad repeat unit at a time.

GαS1–10/GPA11–17/Gαs18–394
GαS1–17/GPA18–24/GαS25–394
GαS1–17/GPA25–31/GαS32–394
GαS1–17/GPA32–38/GαS39–394

The gap that is introduced between residues 9 and 10 in the GαS sequence is to preserve the alignment of the - LLLLGAGE-(positions 1–8 of SEQ ID NO: 1)sequence motif. This class of hybrids can be complemented by cassette mutagenesis of each heptad repeat followed by screening of these collections of "heptad" libraries in standard coupling assays.

A third class of hybrids based on the prediction that the amino terminus forms a helical domain with a heptahelical repeat unit are those that effect the overall hydrophobic or hydrophilic character of the opposing sides of the predicted helical structure (See Lupas et al. supra). In this model, the a and d positions of the heptad repeat abcdefg are found to be conserved hydrophobic residues that define one face of the helix, while the e and g positions define the charged face of the helix. In this class of hybrids, the sequence of the GαS parent is maintained except for specific substitutions at one or more of the following critical residues to render the different helical faces of Gαs more "GPA1-like"

K8Q
+I-10
E10G
Q12E
R13S
N14D
E15F
E15P
K17L
E21R
K28Q
K32L
V36R

This collection of single mutations could be screened for coupling efficiency to yeast Gβγ and then constructed in combinations (double and greater if necessary).

A fourth class of hybrid molecules that span this region of GPA1-Gα hybrids are those that have junctions between GPA1 and Gα subunits introduced by three primer PCR. In this approach, the two outside primers are encoded by sequences at the initiator methionine of GPA1 on the 5' side and at the tetraleucine motif of GαS (for example) on the 3' side. A series of junctional primers spanning different junctional points can be mixed with the outside primers to make a series of molecules each with different amounts of GPA1 and GαS sequences, respectively.

ii. GPA$_{ID}$ and GPA$_{LW}$ Hybrids.

The regions of high homology among Gβγ subunits that have been identified by sequence alignment are interspersed throughout the molecule. The G1 region containing the highly conserved -GSGESGDST-(SEQ ID NO: 2) motif is followed immediately by a region of very low sequence conservation, the "i1" or insert 1 region. Both sequence and length vary considerably among the il regions of the Gα subunits. By aligning the sequences of Gα subunits, the conserved regions bounding the il region were identified and two additional classes of GPA1-Gα hybrids were constructed. The GPA$_{ID}$ hybrids encode the amino terminal 102 residues of GPA1 (up to the sequence -QARKLGIQ-) (SEQ ID NO: 3) fused in frame to mammalian Gα subunits, while the GPA$_{LW}$ hybrids encode the amino terminal 244 residues of GPA1 (up to the sequence LIHEDIAKA-(SEQ ID NO: 4) in GPA1). The reason for constructing the GPA$_{ID}$ and GPA$_{LW}$ hybrids was to test the hypothesis that the il region of GPA1 is required for mediating the interaction of GPA1 with yeast Gβγ subunits, for the stable expression of the hybrid molecules, or for function of the hybrid molecules. The GPA$_{ID}$ hybrids contain the amino terminal domain of GPA1 fused to the il domain of mammalian subunits, and therefore do not contain the GPA1 il region, while the GPA$_{LW}$ hybrids contain the amino terminal 244 residues of GPA1 including the entire il region (as defined by sequence alignments). Hybrids of both GPA$_{ID}$ and GPA$_{LW}$ classes were constructed for GαS, C-αi2, Gαi3, Gαo$_a$, and Gα16; none of these hybrids complemented the gpa1 growth arrest phenotype.

Subsequent to the construction and testing of the GPA$_{ID}$ and GPA$_{LW}$ classes of hybrids, the crystal structures of G$_{transducin}$ in both the GDP and GTPγS-liganded form, and the crystal structure of several Gαil variants in the GTPγS-liganded and GDP-AIF$_4$ forms were reported (Noel et al. supra; Lambright et al. supra; and Coleman et al.(1994) Science 265:1405–1412). The crystal structures reveal that the il region defined by sequence alignment has a conserved structure that is comprised of six alpha helices in a rigid array, and that the junctions chosen for the construction of the GPA$_{ID}$ and GPA$_{LW}$ hybrids were not compatible with conservation of the structural features of the il region observed in the crystals. The junction chosen for the GPA$_{ID}$ hybrids falls in the center of the long αA helix; chimerization of this helix in all likelihood destabilizes it and the protein structure in general. The same is true of the junction chosen for the GPA$_{LW}$ hybrids in which the crossover point between GPA1 and the mammalian Gα subunit falls at the end of the short αC helix and therefore may distort it and destabilize the protein.

The failure of the GPA$_{ID}$ and GPA$_{LW}$ hybrids is predicted to be due to disruption of critical structural elements in the il region as discussed above. Based upon new alignments and the data presented in Noel et al (supra), Lambright et al (supra), and Coleman et al (supra), this problem can be averted with the ras-like core domain and the il helical domain are introduced <u>outside</u> of known structural elements like alpha-helices.

Hybrid A GαS1–67/GPA66–299/GαS203–394

This hybrid contains the entire il insert of GPA1 interposed into the GαS sequence.

Hybrid B GPA1–41/GαS4443–67/GPA66–299/GαS203–394

This hybrid contains the amino terminal 41 residues of GPA1 in place of the 42 amino terminal residues of GαS found in Hybrid A.

iii. Gαs Hybrids.

There is evidence that the "switch region" encoded by residues 171–237 of Gα transducin (using the numbering of (Noel et al (supra) also plays a role in Gβγ coupling. First, the G226A mutation in GαS prevents the GTP-induced conformational change that occurs with exchange of GDP for GTP upon receptor activation by ligand. This residue maps to the highly conserved sequence -DVGGQ-(SEQ ID NO: 5), present in all Gα subunits and is involved in GTP hydrolysis. In both the Gαt and Gα il crystal structures, this sequence motif resides in the loop that connects the β3 sheet and the α2 helix in the guanine nucleotide binding core. In addition to blocking the conformational change that occurs upon GTP binding, this mutation also prevents dissociation of GTP-liganded Gαs from Gβγ. Second, crosslinking data reveals that a highly conserved cysteine residue in the α2 helix (C215 in Gαo, C210 in Gαt) can be crosslinked to the carboxy terminal region of Gβ subunits. Finally, genetic evidence (Whiteway et al. (1993) Mol. Cell Biol. 14:3233–3239) identifies an important single residue in GPA1 (E307) in the β2 sheet of the core structure that may be in direct contact with βγ. A mutation in the GPA1 protein at this position suppresses the constitutive signaling phenotype of a variety of STE4 (Gβ) dominant negative mutations that are also known to be defective in Gα-Gβγ association (as assessed in two-hybrid assay in yeast as well as by more conventional genetic tests).

The GPA1 switch region suppresses coupling to yeast Gβγ (SGS), while in the context of the GPA1 amino terminus the GPA1 switch region stabilizes coupling with Gβγ (GPβγ-SGS). This suggests that these two regions of GPA1 collaborate to allow interactions between Gα subunits and Gβγ subunits. This conclusion is somewhat mitigated by the observation that the GPA$_{41}$-Gαs hybrid that does not contain the GPA1 switch region is able to complement the growth arrest phenotype of gpa1 strains.

The role of the surface-exposed residues of this region may be crucial for effective coupling to yeast Gαγ, and can be incorporated into hybrid molecules as follows below.

GαS-GPA-Switch GαS 1–202/GPA298–350/GαS 253–394

This hybrid encodes the entire switch region of GPA 1 in the context of GαS.

GαS-GPA-α2 GQS 1–226/GPA322–332/GQS 238–394

This hybrid encodes the a$_2$ helix of GPA1 in the context of GαS.

GPA41-GαS-GPA-α2GPA1-41/GQS43-226/GPA322-332/GQS238-394

This hybrid encodes the 41 residue amino terminal domain of GPA1 and the α2 helix of GPA1 in the context of GαS.

In addition, hybrids that alter the surface exposed residues of the β2 and β3 sheets of αS so that they resemble those of the GPA1 QS helix can be made. These altered α2 helical domains have the following structure. (The positions of the altered residues correspond to GαS.)

L203K
D215G
K216S
D229S

These single mutations can be engineered into a GαS backbone singly and in pairwise combinations. In addition, they can be introduced in the context of both the full length GαS and the GPA$_{41}$-GαS hybrid described previously. All are predicted to improve the coupling of Gα subunits to yeast Gβγ subunits by virtue of improved electrostatic and hydrophobic contacts between this region and the regions of Gβ defined by Whiteway and coworkers (Whiteway et al (supra) that define site(s) that interact with GPA1).

In summary, the identification of hybrid Gα subunits that couple to the yeast pheromone pathway has led to the following general observations. First, GPA$_{BAMH1}$ hybrids associate with yeast Gβγ, therefore at a minimum these hybrids contain the determinants in GPA1 necessary for coupling to the pheromone response pathway. Second, the amino terminal 41 residues of GPA1 contain sufficient determinants to facilitate coupling of Gα hybrids to yeast Gβγ in some, but not all, instances, and that some Gα subunits contain regions outside of the first 41 residues that are sufficiently similar to those in GPA1 to facilitate interaction with GPA1 even in the absence of the amino terminal 41 residues of GPA1. Third, there are other determinants in the first 310 residues of GPA1 that are involved in coupling Gα subunits to yeast Gβγ subunits.

The various classes of hybrids noted above are not mutually exclusive. For example, a GPA1 containing GPA1-$_{41}$ could also feature the L203K mutation.

While, for the sake of simplicity, hybrids of yeast GPA1 and a mammalian Gαs have been described here, it will be appreciated that hybrids may be made of other yeast Gα subunits and/or other mammalian Gα subunits, notably mammalian Gαi subunits. Moreover, while the described hybrids are constructed from two parental proteins, hybrids of three or more parental proteins are also possible.

As shown in the Examples, chimeric Gα subunits have been especially useful in coupling receptors to Gαi species.

iv. Expression of Gα

Kang et al. supra reported that several classes of native mammalian Gα subunits were able to interact functionally with yeast a subunits when expression of Gα was driven from a constitutively active, strong promoter (PGK) or from a strong inducible promoter (CUP). These authors reported that rat GαS, Gαi2 or Gαo expressed at high level coupled to yeast βγ. High level expression of mammalian Gα (i.e. non-stoichiometric with respect to yeast βγ) is not preferred for uses like those described in this application. Reconstruction of G protein-coupled receptor signal transduction in yeast requires the signaling component of the heterotrimeric complex (Gβγ) to be present stoichiometrically with Gα subunits. An excess of Gα subunits(as was required for coupling of mammalian Gαi2 and Gαo to yeast Gβγ in Kang et al.) would dampen the signal in systems where Gβγ subunits transduce the signal. An excess of Gα subunits raises the background level of signaling in the system . Preferably, levels of Gα and Gβγ subunits are balanced. For example, heterologous Gα subunits may be expressed from a low copy (CEN ARS) vector containing the endogenous yeast GPA1 promoter and the GPA1 3' untranslated region. The minimum criterion, applied to a heterologous Gα subunit with respect to its ability to couple functionally to the yeast pheromone pathway, is that it complement a gpa1 genotype when expressed from the GPA1 promoter on low copy plasmids or from an integrated, single copy gene. In the work described in this application, all heterologous Gα subunits have been assayed in two biological systems. In the first assay heterologous Gα subunits are tested for an ability to functionally complement the growth arrest phenotype of gpa1 strains. In the second assay the transcription of a fus1-HIS3 reporter gene is used to measure the extent to which the pheromone response pathway is activated, and hence the extent to which the heterologous Gα subunit sequesters the endogenous yeast Gβγ complex. Mammalian Gαs, Gαi2, Gαi3, Gαq, Gα11, Gα16, Gαo$_a$, Gαo$_b$, and Gαz from rat, murine or human origins were expressed from a low copy, CEN ARS vector containing the GPA1 promoter. Functional complementation of gpa1 strains was not observed in either assay system with any of these full-length Gα constructs with the exception of rat and human GαS.

D. Chimeric Yeast βγ Subunits

In addition to or in place of modifying G protein Gα subunits, yeast or heterologous Gβ or Gγ subunits can be modified. The methods described above with regard to Gα modification can be used to alter either or both of these subunits as well. For example, alignments of the yeast sequence and heterologous sequences can be made and combined with information regarding important functional domains. Such information can then be used to provide guidance in making mutations in yeast or heterologous sequences. Likewise, chimeric Gβ or Gγ molecules can be constructed to enhance the coupling of heterologous GPCRs to a yeast pheromone signaling pathway.

The yeast STE4 and STE18 are related to the metazoan G protein β and γ subunits, respectively (Whiteway et al. 1989. Cell. 56:467). The β and γ subunits must be capable of interaction with one another as well as with the a subunit and with the effector. Previous work has suggested that mammalian β or γ subunits are divergent enough from their yeast homologues that they cannot functionally replace STE4 or STE 18. (Coria et al. 1996. Yeast. 12:41). Thus, in preferred embodiments, modifications are made to heterologous Gβ or Gγ subunits expressed in yeast and/or chimeric subunits are made to enhance heterologous receptor coupling.

The primary structure of G-protein β subunits is highly conserved from yeast to humans; Ste4 shares approximately 40% identity with human Gβ isoforms (Leberer et al. 1992 EMBO Journal 11:4085). STE 4 and the Gβs are 420, and 340 or 341 amino acids long, respectively, and belong to the family of proteins with WD-40 motifs (van der Voom and Ploegh. 1992. FEBs Lett. 307:131). These motifs can be used to divide Gβ and STE4 into eight blocks (Coria et al. Yeast 1996. 12:41). Among the mammalian Gβs, some have been found to exhibit Gγ subunit selectivity (Pronin and Gautham. 1992. Proc. Natl. Acad. Sci. USA 89:6220; Schmidt et al. 1992. J. Biol. Chem. 267:13807; Kleuss et al. 1992. Nature. 358:424). An alignment of the metazoan and yeast G protein β subunits is provided by Corai et al. (1996. Yeast. 12:41). Such an alignment can be used to provide guidance for making mutations to G protein β subunits as described for Gα above. In addition, certain regions of STE4 have been found to be important and thus, may be less amenable to manipulation than other portions of the polypeptide. For example, the c-terminus of the STE4 product is essential for downstream signaling (Coria et al. 1995. FEBS Letters 367:122). Mutations to two small regions in the amino terminal half of Ste4 have also been shown to inhibit signaling (Leberer et al. supra). Mutations which influence the interaction of STE4 and GPA1 have also been identified; mutations to the second copy of the WD40 repeat can be modified to reduce the interaction between STE4 and GPA1, without influencing other aspects of STE4 function (Whiteway et al. 1994. Mol. Cell. Biol. 14:3223)

The Gγs, including STE18, diverge more strongly from each other than do the Gβs. Even among the mammalian G protein γ subunits, there is a fair amount of divergence. The γ subunit may determine the functional specificity of the βγ subunit complex. Complete cDNAs for the γ1 subunit from bovine retina (Hurley et al. Proc. Nat'l Acad. Sci USA. 1984. 81:6948) the γ1, γ3, and γ7 subunits from bovine brain (Robishaw et al. J. Biol. Chem. 1989. 264:15758; Gautam et al. Science. 1989. 244:971; Gautam et al. Proc. Nat'l Acad. Sci. USA. 1990 87:7973; Cali et al. J. Biol. Chem. 1992. 267:24023), and the γ5 subunit from bovine and rat liver (Gisher et al. 1992. 12:1585) have been reported.

The STE18 gene of yeast terminates with a CAAX (SEQ ID NO:83) box (where A is an aliphatic amino acid, and X is any uncharged amino acid). This sequence is involved in prenylation of Gγ and is likely important in the localization of Gγ to the membrane and may, thus, be less amenable to manipulation than other portions of the sequence. (Kurjan. 1992. Ann. Rev. Biochem. 61:1097). Saturation mutagenesis has also provided insight into regions of STE18 that are important in STE18 function. Mutations in STE18 which compensate for mutations in STE4 were identified at serine 65, threonine 71, and valine 80. Dominant negative alleles of the STE18 gene were also identified (Whiteway et al. 1992. Biochem. Cell. Biol. 70:1230). These truncated proteins were found to lack the carboxyl terminus of STE 18, including the CAAX box (Whiteway et al. supra).

An alignment of yeast Gγ, STE18, and mammalian Gγs can be made as indicated for the other G protein subunits. Such an alignment can be used in constructing mutant Gγ subunits or chimeric Gγ subunits. Specific examples of chimeric Gγ subunits are provided in the appended examples, for instance in Example 3. In preferred embodiments, mammalian Gγ2 is used in making G protein γ subunit chimeras.

E. Identification of Mutants which Show Enhanced Coupling to Heterologous GPCRS

Any of a number of methods can be used to screen for mutated or chimeric G protein subunits which show enhanced coupling to the heterologously expressed GPCRs.

For example, in order to show that the mutant Gαs subunits can not only associate tightly with yeast βγ, but also dissociate from βγ upon receptor stimulation, an episomal fus1-lacZ reporter plasmid can be introduced along with the heterologous receptor. The addition of an agonist should result in an increase in β-galactosidase units, demonstrating the ability of the mutant Gαs to interact productively with receptor, and to dissociate from βγ upon ligand addition. In addition, the generation of second messengers or mating factor responses (e.g., growth arrest or shmoo formation could be measured).

In another example, such a screen can take advantage of the fact that a gpal fus1-HIS3 colony expressing wild type Gαs can grow upon replica plating to media lacking histidine and containing 1 mM 3-aminotriazole (AT). The growth of this strain occurs due to the partially constitutive state of the pheromone pathway, which leads to partial derepression of the fus1-HIS3 reporter gene. AT inhibits the activity of IGP dehydratase. Cells with low, fixed level of expression of HIS3 are sensitive to the drug, while cells with higher levels are resistant. The amount of AT can be selected to inhibit cells with a basal level of HIS3 expression (whatever that level is) but allow growth of cells with an induced level of expression. A colony containing the desired βγ-coupling Gαs mutant will presumably fail to grow on this media due to the inactivation of the pheromone pathway mediated by tight αβγ association. However, if the selection for the Gαs-bearing plasmid is relaxed, in this case by the addition of limiting amounts of adenine, then the desired mutant colony will only produce growth from that fraction of cells in the colony (usually 5–10%) that have lost the Gαs plasmid. Such a colony will appear red due to the buildup of an intermediate of the adenine pathway. The nonmutated Gα s-containing colonies will appear white on an adenine-limiting plate, since the presence of the Gαs-ADE2 plasmid has no appreciable negative effect on the ability of the cells to grow in 1 mM 3-AT, but confers a selective advantage under adenine-limiting conditions. The visual aspect of the screen allows the facile identification of potential mutants, and eliminates potential unwanted mutations, such as Ste-, because the screen demands a plasmid-dependent phenotype.

Plasmid DNA can then be recovered from putative mutant-bearing cells, amplified and retested on SCAH1 to confirm the plasmid linkage of the mutation. Sequencing of the mutants can then be performed. In addition, the mutations can be subcloned into yeast to rule out the possibility that mutations in noncoding sequences confer the His$^+$ phenotype.

VII. Leader Sequences

It has been demonstrated that most of the mammalian extracellular, secreted proteins are poorly secreted when expressed in yeast. However, in many cases their secretion levels are markedly increased when their native signal sequences are replaced by the signal sequences of yeast proteins that interact more efficiently with the ER translocation complex. Specifically, the signal sequences of yeast invertase and acid phosphatase have been widely used in biotechnology to direct the secretory expression of the heterologous proteins. However, it is well established that even though many foreign proteins are targeted to the ER by the yeast signal sequences, not all of them advance further in the secretory pathway. The major problem consists in the malfolding and/or improper glycosylation of the heterologous proteins that results in their retention in the ER by the quality control apparatus of the yeast cell.

In many cases, a leader sequence of a precursor of yeast mating pheromone, α-factor, have been used successfully to overcome this problem [1. Brake, A. J. (1989) in *Yeast Genetic Engineering* (Barr, P. J., Brake, A. J., and Valenzuela, P., eds) pp. 269–280, Butterworths, London; Brake, A. J. (1990) *Meth. Enzymol.* 185, 408–441, and references cited therein]. This sequence, in addition to the N-terminal signal peptide of 17 residues, includes a hydrophilic pro-region which contains 72 residues and bears three sites of N-linked glycosylation. The pro-region is extensively glycosylated in the ER and Golgi and is cleaved by Kex2 endopeptidase in the late Golgi compartment. The presence of the pro-region at the N-terminus is believed to allow some heterologous proteins to pass the quality control in the ER and to reach the periplasm. It is likely that the pro-region can somehow facilitate correct protein folding. Alternatively, it may be recognized by the quality control apparatus as a properly folded structural unit thus allowing an entire fusion protein to leave the ER.

The invertase leader can also be used. This leader sequence has been demonstrated to be cleaved from nascent invertase peptide, or nascent heterologous peptide, upon entrance into the endoplasmic reticulum, the apparent molecular weight of the receptor is consistent with this interpretation. The enzyme responsible for cleavage of the pre sequence, Kex2, resides in the trans Golgi.

A. Peptide Expression

In certain embodiments, such a leader sequence can be used to express a peptide library of the present invention. Yeast cells are bounded by a lipid bilayer called the plasma membrane. Between this plasma membrane and the cell wall is the periplasmic space. Peptides secreted by yeast cells cross the plasma membrane through a variety of mechanisms and thereby enter the periplasmic space. The secreted peptides are then free to interact with other molecules that are present in the periplasm or displayed on the outer surface of the plasma membrane. The peptides then either undergo re-uptake into the cell, diffuse through the cell wall into the medium, or become degraded within the periplasmic space.

The test polypeptide library may be secreted into the periplasm by any of a number of exemplary mechanisms, depending on the nature of the expression system to which they are linked. In one embodiment, the peptide may be structurally linked to a yeast signal sequence, such as that present in the α-factor precursor, which directs secretion through the endoplasmic reticulum and Golgi apparatus. Since this is the same route that the receptor protein follows in its journey to the plasma membrane, opportunity exists in cells expressing both the receptor and the peptide library for a specific peptide to interact with the receptor during transit through the secretory pathway. This has been postulated to occur in mammalian cells exhibiting autocrine activation. Such interaction could yield activation of the response pathway during transit, which would still allow identification of those cells expressing a peptide agonist. For situations in which peptide antagonists to externally applied receptor agonist are sought, this system would still be effective, since both the peptide antagonist and receptor would be delivered to the outside of the cell in concert. Thus, those cells producing an antagonist would be selectable, since the peptide antagonist would be properly and timely situated to prevent the receptor from being stimulated by the externally applied agonist.

An alternative mechanism for delivering peptides to the periplasmic space is to use the ATP-dependent transporters of the STE6/MDR1 class. This transport pathway and the signals that direct a protein or peptide to this pathway are not as well characterized as is the endoplasmic reticulum-based secretory pathway. Nonetheless, these transporters apparently can efficiently export certain peptides directly across the plasma membrane, without the peptides having to transit the ER/Golgi pathway. It is anticipated that at least a subset of peptides can be secreted through this pathway by expressing the library in context of the α-factor prosequence and terminal tetrapeptide. The possible advantage of this system is that the receptor and peptide do not come into contact until both are delivered to the external surface of the cell. Thus, this system strictly mimics the situation of an agonist or antagonist that is normally delivered from outside the cell. Use of either of the described pathways is within the scope of the invention.

The present invention does not require periplasmic secretion of peptides, or, if such secretion is provided, any particular secretion signal or transport pathway. In certain embodiments, peptides expressed with a signal sequence may bind to and activate receptors prior to their transport to the cell surface.

B. GPCR Expression

In other embodiments, a leader sequence of a yeast secreted protein can be used to direct transport of receptors, for example, G-protein coupled receptors to the plasma membrane as described in detail in the appended examples. Previous work has demonstrated the expression of foreign, secreted proteins in yeast cells using the α-factor leader. However, when a heterologous membrand bound receptor, the rat M5 receptor, was expressed using such a system, it was found that the heterologous GPCR did not functionally integrate into the yeast cell signaling pathway (Huang et al. *Biochem. and Biophys. Res. Comm.* 1992. 182:1180). The transport of both secreted and transmembrane proteins into the endoplasmic reticulum in yeast is promoted by the same protein translocation complex, including the Sec61, Sec62 and Sec63 proteins. All the secreted proteins possess a signal sequence at their N-termini which is recognized by the translocation complex and serves as an ER targeting signal. A typical signal sequence is comprised of several positively charged residues at the N-terminus followed by a hydrophobic core and a C-terminal site of processing by signal peptidase. Some transmembrane proteins, for example, metabotropic glutamate receptors and vasoactive intestinal polypeptide receptors, also possess the N-terminal signal sequences, whereas some do not. In the latter case, a first transmembrane domain is believed to interact with the ER translocation machinery. The use of the α-factor leader sequence may, therefore, be particularly desirable for functional expression of certain receptors.

In certain embodiments, it will be desirable to further modify the yeast cells of the present invention. For example, in one embodiment it will be desirable to disrupt the yeast calnexin-like gene, CNE1, to improve receptor transport from the endoplasmic reticulum to the Golgi. In other embodiments it will be desirable to disrupt of the STP22 to improve transport form the Golgi to the plasma membrane. In yet other embodiments, it will be desirable to overexpress the gene encoding Ast1, to increase transport form the Golgi to the plasma membrane. I yet other embodiments, it will be desirable to disrupt END3 and/or END4, to prevent receptor internalization.

VIII. Test Compounds

A. Exogenously Added Compounds

A recent trend in medicinal chemistry includes the production of mixtures of compounds, referred to as libraries. While the use of libraries of peptides is well established in the art, new techniques have been developed which have allowed the production of mixtures of other compounds, such as benzodiazepines (Bunin et al. 1992. J. Am. Chem. Soc. 114:10987; DeWitt et al. 1993. Proc. Natl. Acad. Sci. USA 90:6909) peptoids (Zuckermann. 1994. J. Med. Chem. 37:2678) oligocarbamates (Cho et al. 1993. Science. 261:1303), and hydantoins (DeWitt et al. supra). Rebek et al. have described an approach for the synthesis of molecular libraries of small organic molecules with a diversity of 104–105 (Carell et al. 1994. Angew. Chem. Int. Ed. Engl. 33:2059; Carell et al. Angew. Chem. Int. Ed. Engl. 1994. 33:2061).

The compounds of the present invention can be obtained using any of the numerous approaches in combinatorial library methods known in the art, including: biological libraries; spatially addressable parallel solid phase or solution phase libraries, synthetic library methods requiring deconvolution, the one-bead one-compound library method, and synthetic library methods using affinity chromatography selection. The biological library approach is limited to peptide libraries, while the other four approaches are applicable to peptide, non-peptide oligomer or small molecule libraries of compounds (Lam, K. S. Anticancer Drug Des. 1997. 12:145).

In one embodiment, the test compound is a peptide or peptidomimetic. In another, preferred embodiment, the compounds are small, organic non-peptidic compounds.

Other exemplary methods for the synthesis of molecular libraries can be found in the art, for example in: Erb et al. 1994. Proc. Natl. Acad. Sci. USA 91:11422; Horwell et al. 1996 Immunophamacology 33:68; and in Gallop et al. 1994. J. Med. Chem. 37:1233. In addition, libraries such as those described in the commonly owned applications U.S. Ser. No. 08/864,241, U.S. Ser. No. 08/864,240 and U.S. Ser. No. 08/835,623 can be used to provide compounds for testing in the present invention. The contents of each of these applications is expressly incorporated herein by this reference.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404406); (Cwirla et al. (1990)

*Proc. Natl. Acad. Sci.* 87:6378–6382); (Felici (1991) *J. Mol. Biol.* 222:301–310); (Ladner supra.).

In certain embodiments, the test compounds are exogenously added to the yeast cells expressing a recombinant receptor and compounds that modulate signal transduction via the receptor are selected. In other embodiments, the yeast cells express the compounds to be tested. For example, a culture of the subject yeast cells can be further modified to collectively express a peptide library as described in more detail in PCT Publication WO 94/23025 the contents of which is expressly incorporated herein by this reference.

Other types of peptide libraries may also be expressed, see, for example, U.S. Pat. Nos. 5,270,181 and 5,292,646; and PCT publication WO94/02502). In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries. In such embodiments, both compounds which agonize or antagonize the receptor- or channel-mediated signaling function can be selected and identified.

B. Peptide Libraries

In certain embodiments, yeast cells can be engineered to produce the compounds to be tested. This assay system has the advantage of increasing the effective concentration of the compound to be tested. In one embodiment, a method such as that described in WO 94/23025 can be utilized.

Other methods can also be used. For example, peptide libraries are systems which simultaneously display, in a form which permits interaction with a target, a highly diverse and numerous collection of peptides. These peptides may be presented in solution (Houghten (1992) *Biotechniques* 13:412421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.). Many of these systems are limited in terms of the maximum length of the peptide or the composition of the peptide (e.g., Cys excluded). Steric factors, such as the proximity of a support, may interfere with binding. Usually, the screening is for binding in vitro to an artificially presented target, not for activation or inhibition of a cellular signal transduction pathway in a living cell. While a cell surface receptor may be used as a target, the screening will not reveal whether the binding of the peptide caused an allosteric change in the conformation of the receptor.

The Ladner et al. patent, U.S. Ser. No. 5,096,815, describes a method of identifying novel proteins or polypeptides with a desired DNA binding activity. Semi-random ("variegated") DNA encoding a large number of different potential binding proteins is introduced, in expressible form, into suitable yeast cells. The target DNA sequence is incorporated into a genetically engineered operon such that the binding of the protein or polypeptide will prevent expression of a gene product that is deleterious to the gene under selective conditions. Cells which survive the selective conditions are thus cells which express a protein which binds the target DNA. While it is taught that yeast cells may be used for testing, bacterial cells are preferred. The interactions between the protein and the target DNA occur only in the cell (and then only in the nucleus), not in the periplasm or cytoplasm, and the target is a nucleic acid, and not a receptor protein. Substitution of random peptide sequences for functional domains in cellular proteins permits some determination of the specific sequence requirements for the accomplishment of function. Though the details of the recognition phenomena which operate in the localization of proteins within cells remain largely unknown, the constraints on sequence variation of mitochondrial targeting sequences and protein secretion signal sequences have been elucidated using random peptides (Lemire et al., *J. Biol. Chem.* (1989) 264, 20206 and Kaiser et al. (1987) *Science* 235:312, respectively).

In certain embodiments of the instant invention, the compounds tested are in the form of peptides from a peptide library. The peptide library of the present invention takes the form of a cell culture, in which essentially each cell expresses one, and usually only one, peptide of the library. While the diversity of the library is maximized if each cell produces a peptide of a different sequence, it is usually prudent to construct the library so there is some redundancy. Depending on size, the combinatorial peptides of the library can be expressed as is, or can be incorporated into larger fusion proteins. The fusion protein can provide, for example, stability against degradation or denaturation, as well as a secretion signal if secreted. In an exemplary embodiment of a library for intracellular expression, e.g., for use in conjunction with intracellular target receptors, the polypeptide library is expressed as thioredoxin fusion proteins(see, for example, U.S. Pat. Nos. 5,270,181 and 5,292,646; and PCT publication W094/02502). The combinatorial peptide can be attached one the terminus of the thioredoxin protein, or, for short peptide libraries, inserted into the so-called active loop.

In one embodiment, the peptide library is derived to express a combinatorial library of polypeptides which are not based on any known sequence, nor derived from cDNA. That is, the sequences of the library are largely random. In preferred embodiments, the combinatorial polypeptides are in the range of 3–100 amino acids in length, more preferably at least 5–50, and even more preferably at least 10, 13, 15, 20 or 25 amino acid residues in length. Preferably, the polypeptides of the library are of uniform length. It will be understood that the length of the combinatorial peptide does not reflect any extraneous sequences which may be present in order to facilitate expression, e.g., such as signal sequences or invariant portions of a fusion protein.

In another embodiment, the peptide library is a combinatorial library of polypeptides which are based at least in part on a known polypeptide sequence or a portion thereof (not a cDNA library). That is, the sequences of the library is semi-random, being derived by combinatorial mutagenesis of a known sequence. See, for example, Ladner et al. PCT publication WO 90/02909; Garrard et al., PCT publication WO 92/09690; Marks et al. (1992) *J. Biol. Chem.* 267:16007–16010; Griffths et al. (1993) *EMBO J* 12:725–734; Clackson et al. (1991) *Nature* 352:624–628; and Barbas et al. (1992) *PNAS* 89:4457–4461. Accordingly, polypeptide(s) which are known ligands for a target receptor can be mutagenized by standard techniques to derive a variegated library of polypeptide sequences which can further be screened for agonists and/or antagonists. For example, the surrogate ligand identified for FPRL-1, e.g., the Ser-Leu-Leu-Trp-Leu-Thr-Cys-Arg-Pro-Trp-Glu-Ala-Met peptide, can be mutagenized to generate a library of peptides with some relationship to the original tridecapeptide. This library can be expressed in a reagent cell of the present invention, and other receptor activators can be isolated from the library. This may permit the identification of even more potent FPRL-1 surrogate ligands.

In still another embodiment, the combinatorial polypeptides are produced from a cDNA library.

In a preferred embodiment of the present invention, the yeast cells collectively produce a "peptide library", preferably including at least $10^3$ to $10^7$ different peptides, so that diverse peptides may be simultaneously assayed for the ability to interact with the exogenous receptor. In an especially preferred embodiment, at least some peptides of the peptide library are secreted into the periplasm, where they may interact with the "extracellular" binding site(s) of an exogenous receptor. They thus mimic more closely the clinical interaction of drugs with cellular receptors. This embodiment optionally may be further improved (in assays not requiring pheromone secretion) by preventing pheromone secretion, and thereby avoiding competition between the peptide and the pheromone for signal peptidase and other components of the secretion system.

In certain embodiments of the present invention, the peptides of the library are encoded by a mixture of DNA molecules of different sequence. Each peptide-encoding DNA molecule is ligated with a vector DNA molecule and the resulting recombinant DNA molecule is introduced into a yeast cell. Since it is a matter of chance which peptide encoding DNA molecule is introduced into a particular cell, it is not predictable which peptide that cell will produce. However, based on a knowledge of the manner in which the mixture was prepared, one may make certain statistical predictions about the mixture of peptides in the peptide library.

The peptides of the library can be composed of constant and variable residues. If the nth residue is the same for all peptides of the library, it is said to be constant. If the nth residue varies, depending on the peptide in question, the residue is a variable one. The peptides of the library will have at least one, and usually more than one, variable residue. A variable residue may vary among any of two to all twenty of the genetically encoded amino acids; the variable residues of the peptide may vary in the same or different manner. Moreover, the frequency of occurrence of the allowed amino acids at a particular residue position may be the same or different. The peptide may also have one or more constant residues.

There are two principal ways in which to prepare the required DNA mixture. In one method, the DNAs are synthesized a base at a time. When variation is desired, at a base position dictated by the Genetic Code, a suitable mixture of nucleotides is reacted with the nascent DNA, rather than the pure nucleotide reagent of conventional polynucleotide synthesis.

The second method provides more exact control over the amino acid variation. First, trinucleotide reagents are prepared, each trinucleotide being a codon of one (and only one) of the amino acids to be featured in the peptide library. When a particular variable residue is to be synthesized, a mixture is made of the appropriate trinucleotides and reacted with the nascent DNA. Once the necessary "degenerate" DNA is complete, it must be joined with the DNA sequences necessary to assure the expression of the peptide, as discussed in more detail below, and the complete DNA construct must be introduced into the yeast cell.

In embodiments in which the test compounds it may be desirable to express such peptides in the context of a leader sequence. Yeast cells are bounded by a lipid bilayer called the plasma membrane. Between this plasma membrane and the cell wall is the periplasmic space. Peptides secreted by yeast cells cross the plasma membrane through a variety of mechanisms and thereby enter the periplasmic space. The secreted peptides are then free to interact with other molecules that are present in the periplasm or displayed on the outer surface of the plasma membrane. The peptides then either undergo re-uptake into the cell, diffuse through the cell wall into the medium, or become degraded within the periplasmic space.

The test polypeptide library may be secreted into the periplasm by any of a number of exemplary mechanisms, depending on the nature of the expression system to which they are linked. In one embodiment, the peptide may be structurally linked to a yeast signal sequence, such as that present in the α-factor precursor, which directs secretion through the endoplasmic reticulum and Golgi apparatus. Since this is the same route that the receptor protein follows in its journey to the plasma membrane, opportunity exists in cells expressing both the receptor and the peptide library for a specific peptide to interact with the receptor during transit through the secretory pathway. This has been postulated to occur in mammalian cells exhibiting autocrine activation. Such interaction could yield activation of the response pathway during transit, which would still allow identification of those cells expressing a peptide agonist. For situations in which peptide antagonists to externally applied receptor agonist are sought, this system would still be effective, since both the peptide antagonist and receptor would be delivered to the outside of the cell in concert. Thus, those cells producing an antagonist would be selectable, since the peptide antagonist would be properly and timely situated to prevent the receptor from being stimulated by the externally applied agonist.

An alternative mechanism for delivering peptides to the periplasmic space is to use the ATP-dependent transporters of the STE6/MDR1 class. This transport pathway and the signals that direct a protein or peptide to this pathway are not as well characterized as is the endoplasmic reticulum-based secretory pathway. Nonetheless, these transporters apparently can efficiently export certain peptides directly across the plasma membrane, without the is peptides having to transit the ER/Golgi pathway. It is anticipated that at least a subset of peptides can be secreted through this pathway by expressing the library in context of the α-factor prosequence and terminal tetrapeptide. The possible advantage of this system is that the receptor and peptide do not come into contact until both are delivered to the external surface of the cell. Thus, this system strictly mimics the situation of an agonist or antagonist that is normally delivered from outside the cell. Use of either of the described pathways is within the scope of the invention. The present invention does not require periplasmic secretion, or, if such secretion is provided, any particular secretion signal or transport pathway.

IX. Screening and Selection: Assays of Second Messenger Generation

When screening for bioactivity of compounds, intracellular second messenger generation can be measured directly. A variety of intracellular effectors have been identified as being G-protein-regulated, including adenylyl cyclase, cyclic GMP, phosphodiesterases, phosphoinositidase C, and phospholipase $A_2$. In addition, G proteins interact with a range of ion channels and are able to inhibit certain voltage-sensitive $Ca^{++}$ transients, as well as stimulating cardiac $K^+$ channels.

In one embodiment, the GTPase enzymatic activity by G proteins can be measured in plasma membrane preparations by determining the breakdown of $\gamma^{32}P$ GTP using techniques that are known in the art (For example, see *Signal Trans-* duction: A Practical Approach. G. Milligan, Ed. Oxford University Press, Oxford England). When receptors that modulate cAMP are tested, it will be possible to use standard techniques for cAMP detection, such as competitive assays which quantitate [$^3$H]cAMP in the presence of unlabelled cAMP.

Certain receptors stimulate the activity of phospholipase C which stimulates the breakdown of phosphatidylinositol 4,5, bisphosphate to 1,4,5-IP3 (which mobilizes intracellular Ca++) and diacylglycerol (DAG) (which activates protein kinase C). Inositol lipids can be extracted and analyzed using standard lipid extraction techniques. DAG can also be measured using thin-layer chromatography. Water soluble derivatives of all three inositol lipids (IP1, IP2, IP3) can also be quantitated using radiolabelling techniques or HPLC.

The mobilization of intracellular calcium or the influx of calcium from outside the cell can be measured using standard techniques. The choice of the appropriate calcium indicator, fluorescent, bioluminescent, metallochromic, or Ca++-sensitive microelectrodes depends on the cell type and the magnitude and time constant of the event under study (Borle (1990) *Environ Health Perspect* 84:45–56). As an exemplary method of Ca++ detection, cells could be loaded with the Ca++ sensitive fluorescent dye fura-2 or indo-1, using standard methods, and any change in Ca++ measured using a fluorometer.

The other product of PIP2 breakdown, DAG can also be produced from phosphatidyl choline. The breakdown of this phospholipid in response to receptor-mediated signaling can also be measured using a variety of radiolabelling techniques.

The activation of phospholipase A2 can easily be quantitated using known techniques, including, for example, the generation of arachadonate in the cell.

In the case of certain receptors, it may be desirable to screen for changes in cellular phosphorylation. Such assay formats may be useful when the receptor of interest is a receptor tyrosine kinase. For example, yeast transformed with the FGF receptor and a ligand which binds the FGF receptor could be screened using colony immunoblotting (Lyons and Nelson (1984) *Proc. Natl. Acad. Sci. USA* 81:7426–7430) using anti-phosphotyrosine. In addition, tests for phosphorylation could be useful when a receptor which may not itself be a tyrosine kinase, activates protein kinases that function downstream in the signal transduction pathway. Likewise, it is noted that protein phosphorylation also plays a critical role in cascades that serve to amplify signals generated at the receptor. Multi-kinase cascades allow not only signal amplification but also signal divergence to multiple effectors that are often cell-type specific, allowing a growth factor to stimulate mitosis of one cell and differentiation of another.

One such cascade is the MAP kinase pathway that appears to mediate both mitogenic, differentiation and stress responses in different cell types. Stimulation of growth factor receptors results in Ras activation followed by the sequential activation of c-Raf, MEK, and p44 and p42 MAP kinases(ERK1 and ERK2). Activated MAP kinase then phosphorylates many key regulatory proteins, including p90RSK and Elk-1 that are phosphorylated when MAP kinase translocates to the nucleus. Homologous pathways exist in mammalian and yeast cells. For instance, an essential part of the *S. cerevisiae* pheromone signaling pathway is comprised of a protein kinase cascade composed of the products of the STE11, STE7, and FUS3/KSS1 genes (the latter pair are distinct and functionally redundant). Accordingly, phosphorylation and/or activation of members of this kinase cascade can be detected and used to quantitate receptor engagement. Phosphotyrosine specific antibodies are available to measure increases in tyrosine phosphorylation and phospho-specific antibodies are commercially available (New England Biolabs, Beverly, Mass.).

Modified methods for detecting receptor-mediated signal transduction exist and one of skill in the art will recognize suitable methods that may be used to substitute for the example methods listed.

In one embodiment, the indicator gene can be used for detection. In one embodiment an indicator gene is an unmodified endogenous gene. For example, the instant method can rely on detecting the transcriptional level of such pheromone system pathway responsive endogenous genes as the Bar1 or Fus1, Fus 2, mating factor, Ste3 Ste13, Kex1, Ste2, Ste6, Ste7, sSst2, or Chs1. (Appletauer and Zchstetter. 1989. Eur. J. Biochem. 181:243)

In other embodiments, the sensitivity of an endogenous indicator gene can be enhanced by manipulating the promoter sequence at the natural locus for the indicator gene. Such manipulation may range from point mutations to the endogenous regulatory elements to gross replacement of all or substantial portions of the regulatory elements. The previous discussion of mutations with regard to G proteins and G protein coupled receptors is reiterated here.

For example, in the case of the Bar1 gene, the promoter of the gene can be modified to enhance the transcription of Bar1 upon activation of the yeast pheromone system pathway. Bar1 gene transcription is iactivated upon exposure of yeast cells to mating factor. The sequence of the Bar1 gene is known in the art (see e.g., U.S. Pat. No. 4,613,572). Moreover, the sequences required for α-factor-enhanced expression of the Bar1, and other pheromone responsive genes have been identified. (Appeltauer and Achstetter 1989. Eur. J. Biochem. 181:243; Hagen et al. 1991. Mol. Cell. Biol. 11:2952). In an exemplary embodiment, the yeast Bar1 promoter can be engineered by mutagenesis to be more responsive, e.g., to more strongly promoter gene transcription, upon stimulation of the yeast pheromone pathway. Standard techniques for mutagenizing the promoter can be used. In such embodiments, it is desirable that the conserved oligonucleotide motif described by Appeltaure et al. be conserved.

In yet other embodiments, rather than measuring second messenger production or alterations in transcription, the activity of endogenous yeast proteins can be assayed. For example, in one embodiment, the signal transduction pathway of the receptor upregulates expression or otherwise activates an enzyme which is capable of modifying a substrate which can be added to the cell. The signal can be detected by using a detectable substrate, in which case loss of the substrate signal is monitored, or alternatively, by using a substrate which produces a detectable product. In certain embodiments, the substrate is naturally occurring. Alternatively, the substrate can be non-naturally occurring. In preferred embodiments, BAR1 activity can be measured.

In other embodiments, the modulation of a receptor by a test compound can result in a change in the transcription of a gene, which is not normally pheromone responsive. In preferred embodiments, the gene is easily detectable. For example, in a preferred embodiment, the subject assay can be used to measure Pho5, a secreted acid phosphatase. Acid phosphatase activity can be measured using standard techniques.

In other embodiments, reporter gene constructs can be used. Reporter gene constructs are prepared by operatively linking a reporter gene with at least one transcriptional regulatory element. If only one transcriptional regulatory element is included it must be a regulatable promoter, At least one of the selected transcriptional regulatory elements must be indirectly or directly regulated by the activity of the selected cell-surface receptor whereby activity of the receptor can be monitored via transcription of the reporter genes.

Many reporter genes and transcriptional regulatory elements are known to those of skill in the art and others may be identified or synthesized by methods known to those of skill in the art. Reporter genes include any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties.

Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101), human placental secreted alkaline phosphatase (Cullen and Malim (1992) Methods in Enzymol. 216:362–368) and green fluorescent protein (U.S. Pat. No. 5,491,084; WO96/23898).

Transcriptional control elements include, but are not limited to, promoters, enhancers, and repressor and activator binding sites. Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al. (1990) Neuron 4: 477–485), such as c-fos, Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

Other promoters and transcriptional control elements, in addition to those described above, include the vasoactive intestinal peptide (VIP) gene promoter (cAMP responsive; Fink et al. (1988), Proc. Natl. Acad. Sci. 85:6662–6666); the somatostatin gene promoter (cAMP responsive; Montminy et al. (1986), Proc. Natl. Acad. Sci. 8.3:6682–6686); the proenkephalin promoter (responsive to cAMP, nicotinic agonists, and phorbol esters; Comb et al. (1986), Nature 323:353–356); the phosphoenolpyruvate carboxy-kinase gene promoter (cAMP responsive; Short et al. (1986), J. Biol. Chem. 261:9721–9726); the NGFI-A gene promoter (responsive to NGF, cAMP, and serum; Changelian et al. (1989). Proc. Natl. Acad. Sci. 86:377–381); and others that may be known to or prepared by those of skill in the art.

In certain assays it may be desirable to use changes in growth in the screening procedure. For example, one of the consequences of activation of the pheromone signal pathway in wild-type yeast is growth arrest. If one is testing for an antagonist of a G protein-coupled receptor, this normal response of growth arrest can be used to select cells in which the pheromone response pathway is inhibited. That is, cells exposed to both a known agonist and a peptide of unknown activity will be growth arrested if the peptide is neutral or an agonist, but will grow normally if the peptide is an antagonist. Thus, the growth arrest response can be used to advantage to discover peptides that function as antagonists.

However, when searching for compounds which can function as agonists of G protein-coupled receptors, or other pheromone system proteins, the growth arrest consequent to activation of the pheromone response pathway is an undesirable effect since cells that bind agonists stop growing while surrounding cells that fail to bind agonists will continue to grow. The cells of interest, then, will be overgrown or their detection obscured by the background cells, confounding identification of the cells of interest. To overcome this problem the present invention teaches engineering the cell such that: 1) growth arrest does not occur as a result of exogenous signal pathway activation (e.g., by inactivating the FAR1 gene); and/or 2) a selective growth advantage is conferred by activating the pathway (e.g., by transforming an auxotrophic mutant with a HIS3 gene under the control of a pheromone-responsive promoter, and applying selective conditions).

Alternatively, the promoter may be one which is repressed by the receptor pathway, thereby preventing expression of a product which is deleterious to the cell. With a receptor repressed promoter, one screens for agonists by linking the promoter to a deleterious gene, and for antagonists, by linking it to a beneficial gene. Repression may be achieved by operably linking a receptor-induced promoter to a gene encoding mRNA which is antisense to at least a portion of the mRNA encoded by the marker gene (whether in the coding or flanking regions), so as to inhibit translation of that mRNA. Repression may also be obtained by linking a receptor-induced promoter to a gene encoding a DNA binding repressor protein, and incorporating a suitable operator site into the promoter or other suitable region of the marker gene.

In the case of yeast, exemplary positively selectable (beneficial) genes include the following: URA3, LYS2, HIS3, LEU2, TRP1; ADE1,2,3,4,5,7,8; ARG1,3,4,5,6,8; HIS1,4,5; ILV1,2,5; THR1,4; TRP2,3,4,5; LEU1,4,5; MET2,3,4,8,9,14,16,19; URA1,2,4,5,10; HM3,6; ASP3; CHO1; ARO 2,7; CYS3; OLE1; IN01,2,4; PR01,3 Countless other genes are potential selective markers. The above are involved in well-characterized biosynthetic pathways. The imidazoleglycerol phosphate dehydratase (IGP dehydratase) gene (HIS3) is preferred because it is both quite sensitive and can be selected over a broad range of expression levels. In the simplest case, the cell is auxotrophic for histidine (requires histidine for growth) in the absence of activation. Activation leads to synthesis of the enzyme and the cell becomes prototrophic for histidine (does not require histidine). Thus the selection is for growth in the absence of histidine. Since only a few molecules per cell of IGP dehydratase are required for histidine prototrophy, the assay is very sensitive.

In another version of the assay, cells can be selected for resistance to aminotriazole (AT), a drug that inhibits the activity of IGP dehydratase. Cells with low, fixed level of expression of HIS3 are sensitive to the drug, while cells with higher levels are resistant. The amount of AT can be selected to inhibit cells with a basal level of HIS3 expression (whatever that level is) but allow growth of cells with an induced level of expression. In this case selection is for growth in the absence of histidine and in the presence of a suitable level of AT.

In appropriate assays, so-called counterselectable or negatively selectable genes may be used. Suitable genes include: URA3 (orotidine-5'-phosphate decarboxylase; inhibits growth on 5-fluoroorotic acid), LYS2 (2-aminoadipate reductase; inhibits growth on α-aminoadipate as sole nitrogen source), CYH2 (encodes ribosomal protein L29; cycloheximide-sensitive allele is dominant to resistant allele), CAN1 (encodes arginine permease; null allele confers resistance to the arginine analog canavanin), and other recessive drug-resistant markers.

In one example, the reporter gene effects yeast cell growth. The natural response to signal transduction via the yeast pheromone system response pathway is for cells to undergo growth arrest. This is a preferred way to select for antagonists of a ligand/receptor pair that stimulates a the pathway. An antagonist would inhibit the activation of the pathway; hence, the cell would be able to grow. Thus, the FAR1 gene may be considered an endogenous counterselectable marker. The FAR1 gene is preferably inactivated when screening for agonist activity.

The reporter gene may also be a screenable gene. The screened characteristic may be a change in cell morphology, metabolism or other screenable features. Suitable markers include beta-galactosidase (Xgal, $C_{12}FDG$, Salmon-gal, Magenta-Gal (latter two from Biosynth Ag)), alkaline phosphatase, horseradish peroxidase, exo-glucanase (product of yeast exb1 gene; nonessential, secreted); luciferase; bacterial green fluorescent protein; (human placental) secreted alkaline phosphatase (SEAP); and chloramphenicol transferase (CAT). Some of the above can be engineered so that they are secreted (although not β-galactosidase). A preferred screenable marker gene is beta-galactosidase; yeast cells expressing the enzyme convert the colorless substrate Xgal into a blue pigment. Again, the promoter may be receptor-induced or receptor-inhibited.

X. Pharmaceutical Preparations of Identified Compounds

After identifying certain test compounds as potential surrogate ligands, or receptor antagonists, the practitioner of the subject assay will continue to test the efficacy and specificity of the selected compounds both in vitro and in vivo. Whether for subsequent in vivo testing, or for administration to an animal as an approved drug, agents identified in the subject assay can be formulated in pharmaceutical preparations for in vivo administration to an animal, preferably a human.

The compounds selected in the subject assay, or a pharmaceutically acceptable salt thereof, may accordingly be formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the compound, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations". Based on the above, such pharmaceutical formulations include, although not exclusively, solutions or freeze-dried powders of the compound in association with one or more pharmaceutically acceptable vehicles or diluents, and contained in buffered media at a suitable pH and isosmotic with physiological fluids. In preferred embodiment, the compound can be disposed in a sterile preparation for topical and/or systemic administration. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions of compounds in isotonic solutions of the desired volume and include, but not exclusively, the use of buffered saline solutions with phosphate or citrate at suitable concentrations so as to obtain at all times isotonic pharmaceutical preparations of the desired pH, (for example, neutral pH).

All patents, published patent applications and other references disclosed herein are hereby expressly incorporated by reference.

EXEMPLIFICATION

The invention now being generally described will be more readily understood by reference to the following examples, which are included merely for purposes of illustration of certain aspects and embodiments of the present invention and are not intended to limit the invention.

EXAMPLE 1

Construction of Chimeric Yeast/Mammalian Gα Subunits

This Example pertains to the construction of chimeric G protein subunits which are made using a first polypeptide derived from a yeast G protein subunit and a second polypeptide derived from a mammalian G protein subunit. The Gα subunit of heterotrimeric G proteins interacts with both the βγ complex and the receptor. The construction of chimeric α subunits can, therefore, enhance receptor coupling. In this example, various G protein subunit chimeras were constructed using a polypeptide derived from yeast GPA1 and several different mammalian Gα subunits. The nucleotide sequence of GPA1 is known in the art. For example, the gene encoding a G protein homolog of *S. cerevisiae* was cloned independently by Dietzel and Kurjan (supra) (who referred to the gene as SCG1) and by Nakafuku, et al. (1987 *Proc Natl Acad Sci* 84:2140–2144) (who called the gene GPA1). The nucleotide sequence of the human G alpha subunits Gαs, Gαi2, Gαi3 also are available in the art. The following information provides specific examples of the construction of G protein subunit, Gα, chimeras.

The Plasmids Used were Constructed as Follows.

pRS416-GPA1 (Cadus 1069). An XbaI—SacI fragment encoding the entire GPA1 promoter region, coding region and approximately 250 nucleotides of 3' untranslated region was excised from 10 YCplac111-GPA1 (from S. Reed, Scripps Institute) and cloned into YEp vector pRS416 (Sikorski and Hieter, Genetics 122: 19 (1989)) cut with XbaI and SacI.

Site-directed mutagenesis of GPA1 (Cadus 1075, 1121 and 1122). A 1.9 kb EcoRI fragment containing the entire GPA1 coding region and 200 nucleotides from the 5' untranslated region was cloned into EcoRI cut, phosphatase-treated pALTER-1 (Promega) and transformed by electroporation (Biorad Gene Pulser) into DH5αF' bacteria to yield Cadus 1075. Recombinant phagemids were rescued with M13KO7 helper phage and single stranded recombinant DNA was extracted and purified according to the manufacturer's specifications. A new NcoI site was introduced at the initiator methionine of GPA1 by oligonucleotide directed mutagenesis using the synthetic oligonucleotide:

5' GATATATTAAGGTAGGAAA CCATGGGGTGTACAGTGAG 3'. (SEQ ID NO: 13). Positive clones were selected in ampicillin and several independent clones were sequenced in both directions across the new NcoI site at +1. Two clones containing the correct sequences were retained as Cadus 1121 and 1122.

Construction of a GPA1-based expression vector (Cadus 1127). The vector used for expression of full length and hybrid mammalian Gα proteins in yeast, Cadus 1127, was constructed in the following manner. A 350 nucleotide fragment spanning the 3' untranslated region of GPA1 was amplified with Taq polymerase (AmpliTaq; Perkin Elmer) using the oligonucleotideprimers A: 5' CGAGGCTC-GAGGGAACGTATAATTAAAGTAGTG 3' (SEQ ID NO: 14) and B: 5' GCGCGGTACCAAGCTTCAATTC-GAGATAATACCC 3' (SEQ ID NO: 15). The 350 nucleotide product was purified by gel electrophoresis using GeneClean II (Bio101) and was cloned directly into the pCRII vector by single nucleotide overlap TA cloning (InVitrogen). Recombinant clones were characterized by restriction enzyme mapping and by dideoxynucleotide sequencing. Recombinant clones contained a novel XhoI site 5' to the authentic GPA1 sequence and a novel KpnI site 3' to the authentic GPA1 sequence donated respectively by primer A and primer B.

The NotI and SacI sites in the polylinker of Cadus 1013 (pRS414) were removed by restriction with these enzymes followed by filling in with the Klenow fragment of DNA polymerase I and blunt end ligation to yield Cadus 1092. The 1.4 kb PstI-EcoRI 5' fragment of GPA1 from YCplac111-GPA1 containing the GPA1 promoter and 5' untranslated region of GPA1 was purified by gel electrophoresis using GeneClean (Bio101) and cloned into PstI-EcoRI restricted Cadus 1013 to yield Cadus 1087. The PCR amplified XhoI-KpnI fragment encoding the 3' untranslated region of GPA1 was excised from Cadus 1089 and cloned into XhoI-KpnI restricted Cadus 1087 to yield Cadus 1092. The NotI and SacI sites in the polylinker of Cadus 1092 were removed by restriction with these enzymes, filling in with the Klenow fragment of DNA polymerase I, and blunt end ligation to yield Cadus 1110. The region of Cadus 1122 encoding the region of GPA1 from the EcoRI site at −200 to +120 was amplified with Vent DNA polymerase (New England Biolabs, Beverly, Mass.) with the primers 5' CCCGAATCCACCAATTTCTTTACG 3' (SEQ ID NO: 16) and

5' GCGGCGTCGACGCGGCCGCGTAACAGT 3' (SEQ ID NO: 17).

The amplified product, bearing an EcoRI site at its 5' end and novel SacI, NotI and SalI sites at its 3' end was restricted with EcoRI and SalI, gel purified using GeneClean II (Bio101), and cloned into EcoRI and SalI restricted Cadus 1110 to yield Cadus 1127. The DNA sequence of the vector between the EcoRI site at −200 and the KpnI site at the 3' end of the 3' untranslated region was verified by restriction enzyme mapping and dideoxynucleotide DNA sequence analysis.

PCR amplification of $GPA_{41}$-Gα proteins and cloning into Cadus 1127. cDNA clones encoding the human G alpha subunits Gαs, Gαi2, Gαi3, and S. cerevisiae GPA1 were amplified with Vent thermostable polymerase (New England Bioloabs, Beverly, Mass.). The primer pairs used in the amplification are as follows:

For GαS: Primer 1: 5'CTGCTGGAGCTCCGCCTGCT-GCTGCTGGGTGCTGGAG3' (SEQ ID NO: 18) (SacI 5')

Primer 2:

5' CTGCTGGTCGACGCGGCCGCGGGGGTTC-CTTCTTAGAAGCAGC3' (SEQ ID NO: 19) (SalI 3')

Primer 3: 5' GGGCTCGAGCCTTCTTAGAG-CAGCTCGTAC3' (SEQ ID NO: 20) (XhoI 3')

For Gαi2: Primer 1: 5' CTGCTGGAGCTCAAGTTGCT-GCTGTTGGGTGCTGGGG3' (SEQ ID NO: 21) (SacI 5')

Primer 2: 5' CTGCTGGTCGACGCGGCCGCGCCCCT-CAGAAGAGGCCGCGGT CC3' (SEQ ID NO: 22) (SalI3')

Primer 3: 5 ' GGGCTCGAGCCTCAGAAGAGGCCG-CAGTC3' (SEQ ID NO: 23) (XhoI 3')

for Gαi3: Primer 1: 5' CTGCTGGAGCTCAAGCT-GCTGCTACTCGGTGCTGGAG3' (SEQ ID NO: 24) (SacI 5')

Primer 2: 5' CTGCTGGTCGACGCGGCCGCCACTAA-CATCCATGCTTCTCAATAAAGTC3' (SEQ ID NO: 25) (SalI 3')

Primer 3: 5' GGGCTCGAGCATGCTTCT-CAATAAAGTCCAC3' (SEQ ID NO: 26) (XhoI 3')

After amplification, products were purified by gel electrophoresis using GeneClean II (Bio101) and were cleaved with the appropriate restriction enzymes for cloning into Cadus 1127.

The hybrid $GPA_{41}$-$G_\alpha$ subunits were cloned via a SacI site introduced at the desired position near the 5' end of the amplified genes and a SalI or XhoI site introduced in the 3' untranslated region. Ligation mixtures were electroporated into competent bacteria and plasmid DNA was prepared from 50 cultures of ampicillin resistant bacteria.

Construction of Integrating Vectors Encoding $GPA_{41}$-$G_\alpha$ Subunits. The coding region of each $GPA_{41}$-$G_\alpha$ hybrid was cloned into an integrating vector (pRS406=URA3 AmpR) using the BssHII sites flanking the polylinker cloning sites in this plasmid. Cadus 1011 (pRS406) was restricted with BssHII, treated with shrimp alkaline phosphatase as per the manufacturer's specifications, and the linearized vector was purified by gel electrophoresis. Inserts from each of the $GPA_{41}$-$G_\alpha$ hybrids were excised with BssHII from the parental plasmid, and subcloned into gel purified Cadus 1011.

Construction of $GPA_{BAM}$-$G_\alpha$ Constructs. A novel BamHI site was introduced in frame into the GPA1 coding region by PCR amplification using Cadus 1179 (encoding a wildtype GPA1 allele with a novel NcoI site at the initiator methionine) as the template, VENT polymerase, and the following primers: Primer A=5' GCATCCATCAATAATC-CAG 3' (SEQ ID NO: 27) and Primer B=5' GAAACAATG-GATCCACTTCTTAC 3' (SEQ ID NO: 28). The 1.1 kb PCR product was gel purified with GeneClean II (Bio101), restricted with NcoI and BamHI and cloned into NcoI-BamHI cut and phosphatased Cadus 1122 to yield Cadus 1605. The sequence of Cadus 1605 was verified by restriction analysis and dideoxy-sequencing of double-stranded templates. Recombinant GPA$_{Bam}$-G$_\alpha$ hybrids of Gαs, Gαi2, and Gα16 were generated. Construction of Cadus 1855 encoding recombinant GPA$_{Bam}$-Gα16 serves as a master example: construction of the other hybrids followed an analogous cloning strategy. The parental plasmid Cadus 1617, encoding native Gα16, was restricted with NcoI and BamHI, treated with shrimp alkaline phosphatase as per the manufacturer's specifications and the linearized vector was purified by gel electrophoresis. Cadus 1605 was restricted with NcoI and BamHI and the 1.1 kb fragment encoding the amino terminal 60% of GPA1 with a novel BamHI site at the 3' end was cloned into the NcoI- and BamHI-restricted Cadus 1617. The resulting plasmid encoding the GPA$_{Bam}$-Gα16 hybrid was verified by restriction analysis and assayed in tester strains for an ability to couple to yeast Gβγ and thereby suppress the gpa1 null phenotype. Two additional GPA$_{Bam}$-Gα hybrids, GPA$_{Bam}$-Gαs and GPA$_{Bam}$-Gαi2, described in this application were prepared in an analogous manner using Cadus1606 as the parental plasmid for the construction of the GPA$_{Bam}$-Gαi2 hybrid and Cadus 1181 as the parental plasmid for the construction of the GPA$_{Bam}$-Gαs hybrid.

EXAMPLE 2

Identification of Critical Regions of Gα and Improvement of the Interaction of Mammalian Gαs with Yeast βγ by Mutation In this Example, critical regions of various mammalian Gα subunits were identified by making the following series of mutations:

D229S in rat Gαs, S270P in human Gα16, S280P in Gpa1-Gαi2-GαoB and S288P in GPA1-Gα12.

The specificity of coupling of a receptor to a heterotrimeric G-protein is largely determined by the α subunit of the G-protein. This fact has been exploited by expressing human 7 transmembrane receptors in yeast and functionally coupling them into the yeast pheromone response pathway, as a path to drug discovery. In order to accomplish this goal mammalian Gα subunits were expressed in yeast cells whose own pheromone-responsive Gα subunit (GPA1), has been disrupted. As the predominant role of GPA1 is to bind to and sequester the effector-signaling βγ component of the heterotrimer, the effector activity of the. mammalian Gα is irrelevant; the activity sought is the ability to bind yeast βγ in the quiescent state, and to release it upon receptor activation.

In general, mammalian Gα subunits couple poorly to the βγ subunits of Saccharomyces cerevisiae. When these Gα s are expressed in yeast that lack their own endogenous Gα subunit, this failure to couple results in the constitutive activation of the pheromone pathway, due to the effector activity of the unbound yeast βγ. The interaction of mammalian Gα s with yeast βγ can be improved through a variety of random and semirandom mutagenesis techniques in conjunction with various genetic selection and screening methods. Such an analysis has highlighted critical regions for α-βγ coupling, as well as identifying residues in Gα that do not directly bind to βγ but that nevertheless mediate this coupling.

Yeast Strains

The following yeast strains were used in these experiments:

CY7757 (MATα ste1 4::trpl ::LYS2 gpal ::LEU2fusl-HIS3farl-1 trpl his3 ura3 leu2 lys2 ade2–1), and CY1316 (MATα gpalΔ1163 farlΔ1442 tbtl-1 fusl-HIS3 can1stel4::trpl ::LYS2 ste3Δ1156 lys2 ura3 leu2 trpl his3) were constructed using standard genetic techniques. The stel4::TRPl, gpal ::LEU2, farl-1 and fusl-HIS3 alleles were derived from GMZ809 (Hrycyna et al. 1991. EMBO J. 10:1699), D111 (Kujan et al. 1987. Cell 50:1001), IH2512 (Chang et al. 1990. 63:999), and SY1390 (Stevenson et al. 1992. Genes and Development 6:1293), respectively. The gpaΔ1163 (a deletion of the internal SphI fragment of GPA1), ste3Δ1156 (a deletion extending from the start codon to the stop codon of STE3), and farlΔ1442 (a deletion from codon 50 through 696 of FAR1) alleles were introduced by two-step gene disruption using 5-fluoroorotic acid (Rothstein. 1991. Methods in Enzymol. Vol. 194). The ste14::trpl ::LYS2 lesion was constructed using pRS624 (Sikorski and Hieter. 1989. Genetics).

Plasmids

For expression of the various Gα constructs, an expression plasmid derived from the centromere plasmid C p1127 was used. This plasmid contains the TRP1 gene as a selectable marker and the GPA1 promoter and terminator separated by an NcoI and XhoI site that act as 5' and 3' cloning sites respectively. Cp3098 contains the rat Gαs subunit subcloned from pYSK136 (Dietzel and Kuian, 1987. Cell. 50:1001), using the 5' NcoI site contained therein and a 3' XhoI site introduced by PCR using the oligonucleotide "gsxhorev" (5'-CCCCTCGAGTTCCCTTCTTAGAGCAGCT) (SEQ ID NO:45). Cp3222 was constructed by replacing the 917 bp HindIII fragment containing the TRP1 gene with a 2.4 kb BbsI-digested PCR fragment encoding the ADE2 gene amplified from genomic wild type yeast DNA using the oligonucleotides "ADE2FWD" (5'-CCCGAAGACCAAGCTTTTGACCAGGTTATTATA) (SEQ ID NO:46) and "ADE2REV" (5'-AAGGAAGACTTAGCTTTATAATTTGGGCTTTAGTT) (SEQ ID NO:47); the ADE2 gene in this plasmid is transcribed in the opposite direction from the Gαs cassette.

The mutation D229S in the wild type rat Gαs was made by amplifying two fragments from the rat Gαs template Cp3098, using the oligo pairs 523 (TTT CTT GTC ACT CCG TTT CTA AC) (SEQ ID NO:48) and D229S reverse (CCCCGTCTCAAGAGCGCTGGCCGCCCACATC) (SEQ ID NO:49); and D229S forward (CCCCGTCTCACTCTGAACGCCGCAAGTGGATCC) (SEQ ID NO:50) and 759 (AGC AAG CAG ATC TTG CTT GTT G) (SEQ ID NO:51). The fragment resulting from the former pair was digested with NcoI and BsmBI, and the fragment from the latter pair was digested with BglII and BsmBI, and together they were ligated into Cp3098 digested with NcoI and BglII to create Cp3390. This plasmid harbored the sequence:

GAT GTG GGC GGC CAG CGC TCT GAA CGC CGC AAG TGG ATC (SEQ ID NO:52)

D V G G Q R S̲ E R R R W I (SEQ ID NO:53)

Thereby encoding rat Gαs having a substitution of serine for the wild-type aspartic acid at position 229.

The plasmid Cp3699, encoding a Gpa1-Gα16 chimera with the S270P mutation, was constructed as follows. KS5714 (5'TCGTCTGGAGCTCAAGCTGCTGCTTTTGGG CCCAGGCGAGAGCGG GAAGAGC3') (SEQ ID NO:54) and KS 4661 (5'CTGCTGGTCGACGCGGCCGCGGGTCACAGC GGTTGAT CTCGTCCAG3) (SEQ ID NO:55) were used to amplify the human Gα16 gene from the 45th to the 374th codon, and this fragment was digested with SacI and SalI, ligated to Cp1127 digested with the same enzymes, yielding Cp3233, encoding a Gpa1 (1–43)-Gα16(45–374) chimera. This plasmid was mutated (S270P) by amplification with the primer pairs G16-271F (GCTAGGTCTCAACCAGTCATCCTCTTTCTCAAC AAAACC) (SEQ ID NO:56) and 524 (ACC CGG AAC GAT TTA ACG AG) (SEQ ID NO: 84), and G16-271R (ACGTGGTCTCATGGTGTGCTTTTGAACCAGGGT AGT) (SEQ ID NO:57) and 713 (AGC GGC TGC AGA TTC CAT TC) (SEQ ID NO:58), digestion of the resulting fragments with BsaI and XhoI, or with BsaI and NheI, respectively, and ligation together into Cp3233 digested with NheI and XhoI to yield Cp3699, harboring the following mutated sequence:

CTA CCC TGG TTC AAA AGC ACA CCA GTC ATC CTC TTT CTC AAC AAA (SEQ ID NO:59)

L P W F X S T P V I L F L N K (SEQ ID NO:60)

thereby encoding human Gα16 having a substitution of proline for the wild-type serine at position 270.

Plasmid Cp3635, encoding a Gpa1-Gαi2-GαoB chimera with the S280P mutation, was constructed as follows. GαoB was amplified from Cp 1131 using the primers ob forward (GGGCGTCTCACATGGGATGTACGCTGAGCG) (SEQ ID NO:61) and ob reverse (GGGGTCGACTCAGTAGAGTCAACAGCCC) (SEQ ID NO:62), and the resulting fragment was digested with BsmBI and SalI, and ligated into Cp1127 digested with NcoI and SalI, yielding Cp3332. The S280P mutation was introduced by amplification with the primer pairs 565 (GAT TGG AGC CGG TGA CTA CC) (SEQ ID NO: 85) and obsp reverse (CCCCCGTCTCATAGGGGTATCAATGAAAAACTT GTTGTTA) (SEQ ID NO:63), and 524 (supra.) and obsp forward (CCCCCGTCTCACCTATCATCCTCTTCCTCAACAAG) (SEQ ID NO:64), digestion of the resulting fragments with AatII and BsmBI, or with BsmBI and SalI, respectively, and ligation together into Cp3332 digested with AatII and SalI to yield Cp3709, harboring the following mutated sequence:

AAC AAC AAG TTT TTC ATT GAT ACC CCT ATC ATC CTC TTC CTC AAC AAG (SEQ ID NO:65)

N N K F F I D T P I I L F L N K (SEQ ID NO:66)

The italicized nucleotides and amino acids indicated above refer to polymorphisms derived from GαoA. (The corresponding GαoB amino acids are W and T rather than F and I.) An SphI-XhoI fragment from Cp3709 was ligated into Cp1183 digested with the same enzymes, to yield Cp3635, encoding a Gpa1(1–43)-Gαi2(36–242)-GαoB(243–354) chimera containing the above changes.

Plasmids encoding GPA1-Gα12 chimerae were constructed as follows. The single PstI site in Cp1127 was eliminated by digesting with BamHI and PstI, blunting the overhangs with T4 DNA polymerase, and ligating the resulting linear DNA; the resulting plasmid (Cp3326) was digested with NcoI and SacI, allowing insertion of a synthetic oligonucleotide encoding the N-terminas 41 amino acids of GPA1p. The synthetic oligonucleotide, which contains a PstI site at condons 18 and 19 of GAP1, was made by annealing phosphorylated oligonucleotide o207 (AAAAGAGCCAATGATGTCATCGAGCAATCGTT GCAGCTGGAGAAACAACGTGACAAGAATG AGCT) (SEQ ID NO:67) with oligonucleotide o208 (CATTCTTGTCACGTTGTTTCTCCAGCTGCAACG ATTGCTCGATGACATCATTGGCTCTTTT GTTC) (SEQ ID NO:68) and oligonucleotide o209 (CATGGGGTGTACAGTGAGTACGCAAACAATAG GAGATGAAAGTGATCCTTTTCTGCAGAAC) (SEQ ID NO:69) with phosphorylated oligonucleotide o210 (TGCAGAAAAGGATCACTTTCATCTCCTATTG TTTGCGTACTCACTGTACACCC) (SEQ ID NO:70), followed by their ligation. The plasmid resulting from the insertion of this approximately 120 bp synthetic DNA fragment, Cp3363, was then digested with SacI and XhoI, permitting the insertion of a PCR-amplified, SacI- and XhoI-digested fragment encoding amino acids 43 through the stop codon of wild-type Gα12. The resulting plasmid Cp3435 thus encodes a chimeric GPA1-Gα12 protein in which the N-terminal 41 residues of GPA1 replace the N-terminal 42 amino acids of wild-type Gα12. An equivalent PCR-amplified, SacI- and XhoI-digested fragment encoding amino acids 43 through the stop codon of the GTPase-deficient mutant of Gα12 was also inserted into Cp3363. The resulting plasmid Cp3436 encodes a chimeric protein in which the N-terminal 41 residues of GPA1 replace the N-terminal 42 amino acids of the Q229L mutant of Gα12.

Cp3435 was used as the template for mutagenesis by Stratagene's Quik-Change protocol using oligonucleotides o286 (CTTCTTCAACGTCCCCATCATCCTC) (SEQ ID NO:71) and o287 (GAGGATGATGGGGACGTTGAAGAAG) (SEQ ID NO:72) to create Cp3822. Cp3822 encodes a GPA1-Gα12 chimera in which the serine corresponding to residue 288 of wild-type Gα12 has been changed to a proline. Cp3435 was also the template for mutating the glycine corresponding to residue 228 of wild-type Gα12 to alanine using oligonucleotides o293 (GGATGTGGGCGCCCAGAGGTCACAG) (SEQ ID NO:73) and o294 (CTGTGACCTCTGGGCGCCCACATCC) (SEQ ID NO:74). This mutant encodes a chimeric Gα subunit that is not likely capable of assuming an activated conformation (E. Lee, R. Taussig, and A. G. Gilman, J. Biol. Chem. 267, 1212 (1992); R. T. Miller, et al., Nature 334, 712 (1988)).

Finally, a 1.9 kb fragment containing the ADE8 gene was cloned into the Hpa I site to Cp3435 to create Cp3506. The unique PstI and SacI sites of Cp3506 were then used to introduce oligonucleotide libraries that encode variable amino acids. That is, Cp3506 was digested with PstI and SacI for the insertion of a library of semi-random oligonucleotides constructed as follows: oligonucleotides o221 (GCGGAGCT CTTTTCTAATTGCAAGGATTGTTC-GATAACGTCAT TAGCTCTCTTATTCTGCAGGG, where M is C or A and N is A, G, C, or T) (SEQ ID NO:75) and o222 (CCCTGCAGAATAAGAGAGCTAATGACGTTATC GAACAATCCTTGCAATTA) (SEQ ID NO:76) were annealed, the partially double-stranded oligonucleotides were filled in with Sequenase, and the fully double-stranded product was cut with SacI and PstI. The resulting library encodes Gα chimerae with the following sequence: The N-terminal 35 amino acids are those of GPA1, followed in succession by 5 completely random amino acids in place of residues 36–40 of GPA1, residues 41–44 of GPA1, and residues 59–380 (stop) of G α2. The random region corresponds to the C-terminal border of the predicted N-terminal α helix. This library was used as a possible source of chimerae that may exhibit improved coupling with STE4/STE18 as a result of optimal positioning of the N-terminal α helix relative to the rest of the Gα subunit.

Wild-type Gα12 shows no greater ability to couple to STE4/STE18 than empty vector. GPA1-Gα12, however, shows clearly improved coupling when assayed at 2.5 mM aminotriazole, with barely detectable improvement at 1 mM aminotriazole. Thus, replacement of the N-terminal Gα helix of Gα12 with the equivalent region of GPA1 increases the coupling of the Gα subunit with STE4/STE18. Even greater coupling is seen with the GPA1-Gα12 S288P mutant: coupling is clear at 0.5 mM AT. In contrast, neither the likely GTPase-deficient GPA1-Gα12 Q227L chimera nor the GPA1-Gα12 G228A chimera show greater coupling than wild-type Gα12.

The library of GPA1-Gα12 chimerae that vary in amino acid sequence at the C-terminal border of the predicted N-terminal α helix was screened for proteins that show improved coupling to STE4/STE18. No such proteins were found.

Media. For the propagation of yeast cells harboring chimeric G protein subunits, standard recipes were used for yeast media. SCA and contains a mixture of amino acids and uracil (See e.g., Rose et al. Methods in Yeast Genetics, 1990), and lacks adenine; the pH was adjusted to 6.8 using 4.5 ml 1M KOH and 25 ml 1M K-Pipes pH6.8 per liter. SCAH1 is the same except it lacks histidine and contains 1 mM (1,2,4)3-aminotriazole, a competitive inhibitor of the His3 gene product. SCH1(1oA) is identical to SCAH1 except that it contains 6.25 μg/ml adenine.

Mutant Libraries. The rat Gαs protein was mutagenized by taking advantage of the error-prone nature of Taq polymerase in the presence of dITP. Rat Gαs was amplified from p3098 for 30 cycles (30 sec 94; 30 sec 50; 90 sec 72) using 705 (5'-GCATCACATCAATAATCCAG) (SEQ ID NO:77) and 386 (5'-AACCCGGAACGATTTAACGAGATCAAGAAC) (SEQ ID NO:78) as primers(these oligonucleotides correspond to the GPA1 promoter and terminator, respectively) and 200 μM dATP, dGTP, dTTP and dITP, and 40 pM dCTP, and the buffer supplied by the manufacturer (Fisher). The PCR product was digested with NcoI and XhoI and ligated into the ADE2 vector described above. Approximately 20,000 DH10B transformants were pooled to create a library of rat Gαs mutants.

Screening Results

The screen for Gαs mutants that show improved binding to yeast Gβγ takes advantage of the fact that a gpa1 fus1-H1S3 colony expressing wild type Gαs can grow upon replica plating to media lacking histidine and containing 1 mM 3-AT, due to the partially constitutive state of the pheromone pathway, which leads to partial derepression of the fus1-HIS3 reporter gene. A colony containing the desired βγ-coupling Gαs mutant will presumably fail to grow on this media due to the inactivation of the pheromone pathway mediated by tight any association. However, if the selection for the Gαs -bearing plasmid is relaxed, in this case by the addition of limiting amounts of adenine, then the desired mutant colony will only produce growth from that fraction of cells in the colony (usually 5–10%) that have lost the Gαs plasmid. Such a colony will appear red due to the buildup of an intermediate of the adenine pathway. The nonmnutated Gαs-containing colonies will appear white on an adenine-limiting plate, since the presence of the Gαs-ADE2 plasmid has no appreciable negative effect on the ability of the cells to grow in 1 mM 3-AT, but confers a selective advantage under adenine-limiting conditions. The visual aspect of the screen allows the facile identification of potential mutants, and eliminates potential unwanted mutations, such as Ste-, because the screen demands a plasmid-dependent phenotype.

A library of mutagenized rat Gαs genes under the control of the GPA1 promoter was introduced into a gpa1 fus1-HIS3far1 ade2 strain (CY7757) and approximately 10,000 colonies were selected on 40 SCA plates. After 2 days of growth at 30°, the colonies were replica plated to SCH1 (1oA) plates to identify those bearing mutant Gαs proteins capable of suppressing the pheromone pathway through a tighter interaction with endogenous yeast βγ; such colonies appear red due to the outgrowth of Ade-cells, because the Ade+ component of the colony is incapable of overcoming the selection for His+, which demands a pheromone pathway at least partially derepressed. As expected, colonies that produce red replicas on SCH1(1oA) are unable to grow on SCAH1, where the ADE2-Gαs plasmid is strictly required.

Plasmid DNA was recovered from putative mutant-bearing cells, amplified in *E. coli* DH10B, retransformed into CY7757 and retested on SCAH1 to confirm the plasmid linkage of the mutation. Sequencing of the mutants revealed single or double point mutations as described in Table 1 below. In all cases, subcloning of the mutations into a wild type Gαs-TRP1 plasmid (p3098) as performed to rule out the possibility that mutations in noncoding sequences confer the His+phenotype. These subcloned plasmids were tested in a different gpa1 fus1-HIS3 strain, CY1316.

TABLE 1

| Mutant | Mutations |
|---|---|
| rN5-4; hN7; hN8-1; rI7-5 | E10K (GAG→AAG) |
| hI-8 | D229V (GAT→GTT); S82N (AGC→AAC) |
| hN8-2 | S286P (TCT→CCT); E75V (GAG→GTG) |
| rA | S286P (TCT→CCT) |
| rJ | N254D (AAC→GAC) |

For those mutants with two mutations, the bold type indicates the mutation that confers the improved coupling to Gαs, as determined by subcloning into Cp3098. FIG. 2 depicts the behavior of the Gαs mutations. All except S286P eliminate the growth of the gpa1 fus1-HIS3 strain on 0.2 mM 3-AT, indicating efficient suppression of the pheromone pathway. This effect may result from an improved affinity of Gαs·GDP for yeast Gβγ, without discounting other possible explanations, such as a reduction in GTP affinity or an augmented GTPase activity.

Examination of the alignments between various families of Gα subunits revealed that despite the high degree of conservation in the "Switch 2" region among different Gα subunits, Gαs possesses an aspartate at position 229, whereas all other Gα subunits possess a serine at this position. As one of the mutants had altered this aspartate to a valine, suggesting its importance in βγ binding, it was asked whether simply changing the aspartate to the more common serine residue would also serve to improve the αβγ interaction, while preserving a "natural" Switch 2 structure. FIG. 2 shows that the D229S allele confers a phenotype nearly as dramatic as that conferred by the original D229V mutation. It is also worthy of note that one of the other mutations, N254D, is analogous to D229S in that all Gα subunits except that Gαs possess an aspartate at this position.

In order to improve further on the αβγ interaction, a double mutant E10K D229S was constructed using standard molecular biology techniques. In FIG. 2 it can be seen that the two mutations act synergistically in that the double mutant possesses a phenotype drastically improved over that of either single mutation, to a level comparable with the endogenous yeast Gpa1.

In order to avoid the inherent instability (~5% per cell division) of episomal plasmids in yeast, mutant Gαs genes were integrated (E10K, D229S, S286P, and N254D, as well as the double mutant E10K D229S) at the gpa1 locus of CY1316, thereby preserving the promoter and terminator used in the episomal version. The resultant strains mimic the behavior of the analogous strains carrying mutant Gαs on an episome.

In order to show that the mutant Gαs subunits can not only associate tightly with yeast βγ, but also dissociate from βγ upon receptor stimulation, the human adenosine A2a receptor was introduced under the control of the PGK promoter into the various integrated Gαs mutant backgrounds, along with an episomal fus1-lacZ reporter plasmid. As expected, the addition of the exogenous adenosine analog NECA results in a ~10 fold increase in β-galactosidase units, demonstrating the ability of the mutant Gαs to interact productively with receptor, and to dissociate from βγ upon ligand addition.

The S286P mutation suggested a possible method for expanding the spectrum of Gα subunits that can interact with yeast Gβγ. It was reasoned that because all mammalian Gα subunits possess a serine at this position and a proline is found in Gpa1, the S286P substitution might be extrapolated to other mammalian Gα subunits to improve their apparent Gβγ affinity. It has previously been shown that the substitution of the first 43 amino acids of yeast Gpa1, corresponding to the amino terminal alpha-helical domain, for the corresponding segment of Gαi2 results in a dramatic increase in the apparent affinity of Gαi2 for the yeast Gβγ subunit, as revealed by suppression of the constitutive Gβγ pheromone signal ("41-i2"). This modification to Gα16 and Gα12 improved their ability to sequester yeast βγ, and this affinity is further strengthened by the substitution of the appropriate serine residue (corresponding to position 286 in Gαs) with proline. In addition, the apparent βγ affinity of the triple chimera Gpa1(1–43)-Gαi2(36–242)-GαoB(243–354) was also significantly improved by the appropriate S→P substitution.

EXAMPLE 3

Construction of STE18/Mammalian Gγ Chimeric Proteins

Chimeric proteins comprising STE18, the wild type Gγ subunit of yeast, were also made. The wild type STE18 nucleotide sequence is available in the art. The carobxy terminal 34 amino acids of STE18 are as follows:

GYPVAGSNHFIEGLKNAQKNSQMSNSNSVCCTLM (SEQ ID NO: 29)

The wild type human Gγ nucleotide sequences are available in the art. The carboxy terminal 24 amino acids of human Gγ are as follows:

DPLLTPVPASENPFREKKFFCAIL (SEQ ID NO:30)

The underlined residues shown are conserved among all of the mammalian Gγ subunits The STE18-mammalian Gγ chimeras were constructed using standard molecular biology techniques. The following is a list of the Gγ chimeras which were generated, all are modified forms of yeast STE 18 which comprise a portion of a Gγ subunit. The sequences shown below represent a carboxy terminal alignment of the sequences. The two dots before the first amino acid shown in each of the sequences in the following list indicate that the wild type STE18 amino terminal sequence is present in all cases before the first amino acid shown. The residues of yeast STE18 origin are in normal type, while those of mammalian Gγ origin appear in bold. The last amino acid shown represents the carboxy terminus of each chimera.

| Name of Chimera | Amino Acid Sequence | Mammalian γ subunit | | |
|---|---|---|---|---|
| Sγ0 | ..GYPVAGSNHFIEGLKNAQKNSQMSNSNSVCAIL | Gγ2 | $E^{-/+}$ | (SEQ ID NO:31) |
| Sγ4 | ..GYPVAGSNHFIEGLKFFCCTLM | Gγ2 | $E^+$ | (SEQ ID NO:32) |
| Sγ6 | ..GYPVAGSNHFIEGLKNPFREKKFFCCTLM | Gγ2 | $E^+$ | (SEQ ID NO:33) |
| Sγ8 | ..GYPVPASENPFREKKFFCCTLM | Gγ2 | $E^+$ | (SEQ ID NO:34) |
| Sγ10 | ..GYPVAGSNPFREKKFFCCTLM | Gγ2 | $E^+$ | (SEQ ID NO:35) |
| Sγ12 | ..GYPVAGSNHFREKKFFCCTLM | Gγ2 | $E^+$ | (SEQ ID NO:36) |
| Sγ14 | ..GYPVAGSNHFIEKKFFCCTLM | Gγ2 | $E^+$ | (SEQ ID NO:37) |
| Sγ601 | ..GYPVAGSNHFIEGLKNPFKELKGGCCTLM | Gγ1 | $E^+$ | (SEQ ID NO:38) |
| Sγ605 | ..GYPVAGSNHFIEGLENPFRPQKVCCTLM | Gγ5 | $E^+$ | (SEQ ID NO:39) |
| Sγ607 | ..GYPVAGSNHFIEGLKNPFKDKKPCCTLM | Gγ7 | $E^+$ | (SEQ ID NO:40) |
| Sγ610 | ..GYPVAGSNHFIEGLKNPFREPRSCCTLM | Gγ10 | $E^+$ | (SEQ ID NO:41) |
| Sγ611 | ..GYPVAGSNHFIEGLKNPFKEKGSCCTLM | Gγ11 | $E^+$ | (SEQ ID NO:42) |
| Sγ16 | ..GYPVAGSNHFIEGLKNAQKNPFREKKFFCCTLM | Gγ2 | $E^+$ | (SEQ ID NO:43) |
| Sγ18 | ..GYPVAGSNHFIEGLKNPFREKKFFCTIL | Gγ4 | $E^+$ | (SEQ ID NO:44) |

EXAMPLE 4

Screens for Modulators of G Protein Activity

Screens for modulators of G protein, in this case Gα, activity may be performed as =shown in the following examples for illustration purposes, which are intended to be non-limiting.

Strains CY4874 and CY4877 are isogenic but for the presence of Q205L mutation in the cloned $G\alpha_{i2}$ gene cloned into plasmid 1. Strains CY4901 and CY4904 each have a chromosomally integrated chimeric Gα fusion comprising 41 amino acids of gpa1 at the N terminus of the human $G\alpha_{i2}$ gene and are isogenic but for the presence of a constitutively activating mutation in the C5a receptor gene of CY4901. Strain CY5058 is a gpa1 mutant which carries only the yeast Gβγ subunits and no Gα subunit. This strain is a control strain to demonstrate specificity of action on the Gα subunit.

Suppression of Activation by Mutation of Gα

The Q205L mutation is a constitutively activated GTPase deficient mutant of the human $G\alpha_{i2}$ gene. Antagonist compounds, chemicals or other substances which act on $G\alpha_{i2}$ can be recognized by their action to reduce the level of activation and thus reduce the signal from the fus1-lacZ reporter gene on the second plasmid (Plasmid 2).

A. GTPase $G\alpha_{i2}$ Mutants test component=$gpa_{41}$-$G\alpha_{i2}$ ($Q_{205}L$)

control component=$gpa_{41}$i-$G\alpha_{i2}$

As well as the CY4874 and CY4877 constructs detailed above, similar strains with fus1-His3 or fus2-CAN-1 growth readouts may also be used. The fus1-His3 strains are preferred for screening for agonists and the fus2-CAN1 strains are preferred for antagonist screens.

| Readout | test strain | effect of $G\alpha_{i2}$ antagonist | control strain |
|---|---|---|---|
| fus1-HIS3 | CY4868 | inhibit growth of –HIS +AT (Aminotriazole) | CY4871 |
| fus1-lacZ | CY4874 | reduce β-gal activity | CY4877 |
| fus2-CAN1 | CY4892 | induce growth on canavanine | CY4386 |

In each case an antagonist should cause the test strain to behave more like the control strain.

B. GTPase Gαs Mutants (Gα Specificity)

test component=$G\alpha_s(Q_{227}L)$ control component=$G\alpha_s$

| Readout | test strain | effect of $G\alpha_{i2}$ antagonist | control strain |
|---|---|---|---|
| fus1-HIS3 | CY4880 | none | CY4883 |
| fus1-lacZ | CY4886 | none | CY4889 |
| fus2-CAN1 | CY4895 | none | CY4898 |

In each case a non-specific antagonist would cause the test strain to behave more like the control strain.

Additional media requirements: -TRP for Gα plasmid maintenance in fus1-HIS3 and fus2-CAN1 screens and -TRP -URA for Gα and fus1-lacZ plasmid maintenance in fus1-lacZ screen.

II. Suppression of Activation by Receptors Constitutively Activated C5a Receptors test component=C5aR* ($P_{184}L$, activated C5a Receptor)

control component=C5aR

The C5aR* mutation has a Leucine residue in place of the Proline residue of the wild-type at position 184 of the amino acid sequence.

| Readout | test strain | effect of $G\alpha_{i2}$ antagonist | control strain |
|---|---|---|---|
| fus1-HIS3 | CY4029 | inhibit growth of –HIS +AT (Aminotriazole) | CY2246 |
| fus1-lacZ | CY4901 | reduce β-gal activity | CY4904 |
| fus2-CAN1 | CY4365 | induce growth on canavanine | CY4362 |

In each case an antagonist should cause the test strain to behave more like the control strain.

Additional media requirements: -LEU for receptor plasmid maintenance in fus1-HIS3 and fus2-CAN1 screens and -LEU-URA for receptor and fus1-lacZ plasmid maintenance in fus1-lacZ screen, non-buffered yeast media (pH 5.5).

The data presented below show a Summary of various Gα Families Coupled in Yeast

| | | min [AT]i (mM) | Coupling |
|---|---|---|---|
| Gαi: | GPA1(41)-Gαi2 | 0.5 | yes |
| | GPA1(41)-Gαi3 | 0.5 | yes |
| | Gαi1 | 1.5 | yes |
| | GPA1(41)-Gαi1 | 0.5 | yes |
| Gαs: | various point mutants | 0–0.5 | yes |
| Gα16: | GPA1(41)-Gα16(S-P) | 1.0 | yes |
| | GPA1(20)-Gα16 | 1.0 | yes |
| | GPA1(20)-Gα16(S-P) | 0.5 | yes |
| Gαo: | GPA1(41)-Gαi2-Gαo(40) | 1.0 | yes |
| | GPA1(41)-Gαi2-Gαo(110)(S-P) | 1.0 | yes |
| | GPA(41) with STE4Dins | 0.5 | |
| Gα12/13: | GPA1(41)-Gα12 | 2.5–5.0 | LIRMA |
| | GPA1(41)-Gα12(S-P) | 1.0 | |

EXAMPLE 5

The Sγ6 Mutant is Effective in Coupling to Mammalian G Protein Coupled Receptors The effect of the Sγ6 mutant was tested on the coupling of mammalian GPCRs. Results are shown which compare the ability of the wild-type STE18 and Sγ6 mutant in the context of four different Gαs. Note that GPA41Gα12 is a chimera containing the amino terminal 41 amino acids of yeast GPA1 in tandem with Gα12; GPA41Gα16(S27P) contains the amino terminal 41 amino acids of yeast GPA1 fused to Gα16 which has a Pro for Ser substitution at position 27; Gαs (D229S) is the mammalian Gαs with a Ser for Asp substitution at position 229.

| | gpa$_{41}$Gαi2 | | gpa$_{41}$ Gα16(S27P) | | Gαs(D229S) | | GPA1 | |
|---|---|---|---|---|---|---|---|---|
| | STE | | STE | | | | | |
| Receptor | 18 | Sγ6 | 18 | Sγ6 | STE18 | Sγ6 | STE18 | Sγ6 |
| FPR1 and Galanin | – | +++ | – | | – | | – | |
| Rat VIP | – | – | – | | – | +++ | | |
| ML1b | – | | – | | – | | ++ | |
| C5a | +++ | +++ | +/– (L) | ++ | | | – | |
| FPRL | +++ | +++ | +(L) | ++ | | | – | |
| IL-8 (rabbit) | +++ | +++ | LIR-MA | ++ | | | +++ | |
| A2a | – | – | ++(L) | ++ | +++ | | ++ | |

(L) indicates a low level of ligand independent receptor activation (LIRMA) that does not obscure ligand dependent signal.
LIRMA indicates a high level of LIRMA that totally obscures any ligand dependent effect
+ indicates ligand dependent growth
– indicates no ligand dependent growth The following abbreviations are used in the Table. VIP (vasoactive intestinal peptide); ML1b (melatonin receptor); C5a (complement cascade component); FPRL (formyl peptide related receptor); IL-8 (interleukin 8); A2a (Adenosine 2a receptor)

EXAMPLE 6

Development of Four Yeast Strains for Orphan Receptor Expression

This Example illustrates the development of four yeast strains, each expressing different chimeric G protein subunits, for use in drug screening assays. The use of four different types of G protein subunits in the yeast cells provides an opportunity to achieve optimal G protein receptor coupling in at least one of the yeast strains. The genotypes of four exemplary yeast strains are illustrated in the table below:

| Genotypes of Four exemplary yeast strains for Orphan Receptor Expression | |
|---|---|
| CY10103 | MATα ste 18γ6-3841 gpa1 (41)-Gαi2 far1Δ1442 cyh2 tbt1—1 fus1-HIS3 can1 ste14::trp1::LTS2 ste3Δ1156 lys2 ura3 leu2 trp1 his3 ade2Δ3447 ade8Δ3457 |
| CY10132 | MATα ste 18γ6-3841 gpa1 (41)-Gα16(S270P) far1Δ1442 tbt-1 fus1-HIS3 can1 ste14::trp1::LYS2 ste3Δ1156 lys2 ura3 leu2 trp1 his3 ade2Δ3447 ade8Δ3457 |
| CY10150 | MATα ste 18γ6-3841 gpa1 (41)-Gαs(D229S) far1Δ1442 tbt1—1 fus1-HIS3 can1 ste14::trp1::LYS2 ste3Δ1156 lys2 ura3 leu2 trp1 his3 ade2Δ3447 ade8Δ3457 |
| CY10560 | MATα ste 18γ6-3841 far1Δ1442 tbt1—1 fus1-HIS3 can1 ste14::trp1::LYS2 sst2Δ2 ste3Δ1156 lys2 ura3 leu2 trp1 his3 ade2Δ3447 ade8Δ3457 |

As discussed above, Gα and Gγ chimeras are integrated at the gpa1 and ste18 loci respectively. Fus1-HIS3 is integrated at the fus1 locus and is phenotypically fus1 minus. A listing of phenotypes associated with the genotypes listed above is provided below.

| | |
|---|---|
| MATα | mating type resulting in production of α-factor and responsiveness to a-factor |
| ste18γ6 | chimeric yeast Gγ/Human Gγ2, enchances interaction with receptor |
| gpa1(41)-Gαi2 | chimeric yeast Gα/Human Gαi2, enchances interaction witn receptor |
| gpa1(41)-Gα16(S270P) | chimeric yeast Gα/mutant Human Gα16, enchances interaction with yeast βγ |
| gpalp-Gαs(D229S) | mutant Human Gαs, enchances interaction with yeast βγ |
| far1Δ1442 | eliminates growth arrest response in pheromone pathway |
| cyh2 | recessive resistance to cycloheximide |
| tbt1-1 | poorly characterized enhanced transformation by electroporation |
| fus1-HIS3 | pheromone responsive histidine prototrophy (aminotriazole resistance) |
| can1 | recessive resistance to canavinine |
| ste14::trp1::LYS2 | eliminates carboxymethylation of isoprenylated proteins leading to reduced background through the pheromone response pathway |
| sst2Δ2 | supersensitivity resulting from GAP activity on GPA1 |
| ste3Δ1156 | deletion of a-factor receptor gene |
| lys2 | lysine auxotrophy and resistance to α-aminoadipate |
| ura3 | uracil auxotrophy, complementation by ligand plasmids |
| leu2 | leucine auxotrophy, complementation by receptor plasmids |
| trp1 | tryptophan auxotrophy, complementation by fus1-lacZ plasmid |
| his3 | histidine auxotrophy, complementation by fus1-HIS3 |
| ade2Δ3447 | adenine auxotrophy, leads to generation of red pigment |
| ade8Δ3457 | adenine auxotrophy, eliminates generation of red pigment in ade2 cells, complemented by receptor plasmid leading to colorimetric verification of its presence | primers provided XbaI and NheI restriction sites at the 5'-and3'-terminus of the amplified fragment, respectively. The total of 30 cycles of PCR was performed; each cycle included denaturation at 94° C. for 45 sec, annealing at 53° C. for 1 min, and polymerization at 72° C. for 1.5 min. The amplified fragment was digested with XbaI and NheI and subcloned into XbaI site of the plasmid Cadus 1289 (pLPX$_t$) (LEU2 PGKp 2mu-ori REP3 AmpR) in appropriate orientation. This gave rise to the plasmid Cadus 4257 (pPP5) (LEU2 PGKp PHO5t 2mu-ori REP3 AmpR).

Example 7

Construction of the α-Factor Leader-based Expression Vectors

A yeast vector for the expression of mammalian G protein-coupled receptors fused to a leader sequence of prepro-α-factor has been constructed as follows. A 0.38-kb fragment including a transcription terminator of yeast gene PH05 was amplified by PCR using a plasmid pTER as a template. The latter plasmid was constructed by subcloning of a Sau3A-PstI fragment of PH05 gene (GenBank accession number A07173) into the vector pUC19 digested with BamHI and PstI. PCR primers used were TER1, 5'-GGATCTAGAGGATCCTGGTACGTTCCTC-3' (SEQ ID NO: 6), and TER2, GTCGCTAGCCAAGCTTGCATGCCTGCAG-3' (SEQ ID NO: 7) (BRL, Life Technologies, Gaithersburg, Md.). The A 0.27-kb fragment of yeast gene MFα1 encoding the entire preproregion and a first spacer peptide KREAEA (SEQ ID NO: 86) of the α-factor precursor was amplified by PCR using a plasmid pAC109 (Ostanin et al. 1994. J. Biol. Chem. 269:897 1) as a template together with a pair of oligonucleotide primers, MF5, 5'-GCAGTCATGAGATTTCCTTCAATTTTACTGC-3', (SEQ ID NO: 8) and MF3, 5'-CAGCCCATGGCTTCAGCCTCTC=TATCC-3' (SEQ ID NO: 9). PCR was performed under the same conditions as those described above for the amplification of PHOO5 terminator. As a result, the BspHI and NcoI restriction sites were generated at the 5'-and 3'-terminus of the amplified fragment, respectively. The fragment was treated with BspHI and NcoI and subcloned into an NcoI site of plasmid Cadus 4257 in appropriate orientation.

The resulting plasmid Cadus 4258 (PPMP15) (LEU2 PGKp Mfα1 prepro PHO5t REP3 AmpR) carries a strong constitutive promoter of PGK gene followed by the α-factor leader-encoding sequence, as well as the PHO5 transcription terminator. The unique restriction sites NcoI situated at the 3'-terminus of the leader sequence, as well as XbaI and BamHI localized at the 5'-terminus of the terminator can be used for sublconing of the G protein-coupled receptor-encoding sequences. The presence of a transcription terminator in the expression vector may allow avoidance of heterogeneity of the receptor specific mRNA and, therefore, to increase its stability.

In addition, a vector Cadus 4431 (PPMP15-HA) has been constructed which can be used for the expression of receptors tagged with hemagglutinin (HA) epitope at their C-termini. A synthetic adaptor composed of two oligonucleotides, HAtop, 5'-GATCCGCTTACCCATACGATGTTCCAGATTACG CTGCTTGA-3'(SEQ ID NO: 10), and HAbot, 5'-GATCTCAAGCAGCGTAATCTGGAACATCGTA-3' (SEQ ID NO: 11), was introduced into a BamHI site of the plasmid Cadus 4258 in the orientation that restores this site only on the side proximate to the leader-encoding sequence. Insertion of the receptor-encoding sequence lacking a stop codon into the NcoI and BamHI sites of the resulting vector encode a receptor bearing a C-terminal extension SAYPY-DVPDYAA (SEQ ID NO: 12).

EXAMPLE 8

Development of a Functional Assay for the Human Nociceptin Receptor

The prepro sequences of yeast α-factor were inserted 3' to the PGK promoter and just 5' to the receptor cloning site of the standard yeast expression vector pLPXt (a PGK promoter expression vector, using the NcoI and XbaI sites) to create the vector pMP15. This results in the synthesis of a chimeric receptor that matures to receptor devoid of α-factor sequences in the Golgi.

This vector was used to develop a yeast-based human nociceptin receptor assay. The prepro-α-factor-nociceptin receptor expression plasmid was introduced into several isogenic strains differing in expression of chimeric STE18-human Gγ proteins, as described herein.

The nociceptin receptor expressed as a fusion to the α-factor leader exhibited a cell surface staining pattern which was similar to that observed for the Ste2 receptor. Consistent with this, the fusion receptor was shown to undergo both outer chain glycosylation and processing by Kex2 protease that occur in Golgi. Thus, the leader sequence of the α-factor precursor appears to direct efficient transport of the receptor to the cell surface.

Receptor activity was also tested in an additional Cadus yeast strain, CY2120. CY2120 contains a deletion of the endogenous yeast Gα protein GPA1, but carries the intact yeast Gγ. Similar to other Cadus yeast strains, the endogenous HIS3 gene is defective and FUS1-HIS3 is integrated into the genome. This strain contains a novel mutation in the SST2 gene. SST2 encodes a protein that increases the rate at which GPA1 undergoes GTP hydrolysis. Thus in the absence of SST2, GPA1 stays in the GTP-bound state longer. Functionally, this means that GPA1 is active for a longer period of time and is therefore capable of transmitting the signal from a seven transmembrane receptor for a longer period of time (if the particular seven transmembrane receptor is capable of interacting with GPA1). This discovery was further corroborated by the results of a functional growth assay. The strain CY2120 (MTAα sst2*2far1*1442 tbt1-1 fus1-HIS3 can1 ste14::trp1::LYS2 ste3*1156 lys2 ura3 leu2 trp1 his3) coexpressing the α-factor leader-nociceptin receptor fusion protein and the Gpa1Gα subunit have been shown to exhibit nociceptin-induced growth as well as approximately 10-fold activation of the β-galactosidase expression in response to nociceptin. No ligand-induced growth was observed for the same strain expressing the nonfusion receptor.

EXAMPLE 9

Improvement of a Growth Assay for the Human Melanocortin 4 Receptor

The human melanocortin 4 receptor (MC4R) was shown to be functional in yeast when expressed as a nonfusion protein. It couples to the mating pheromone response pathway through $G\alpha_s$ D229S subunit, as demonstrated by growth activation of strain CY9438 (MATα ste18γ6-3843 far1*1442 tbt1-1fus1-HIS3 can1 ste14::trp1::LYS2 ste3*1156 lys2 ura3 leu2 trp1 his3) in response to six different MC4R-specific agonists. However, the sensitivity of the growth assay is considerably improved when this receptor is expressed as a fusion to the α-factor leader, presumably, due to the elevated level of the receptor at the cell surface.

The human Melanocortin 4 receptor cDNA was cloned into three yeast expression vectors under control of the PGK promoter. The full-length receptor cDNA expressed from the plasmid pLPXt was used in all biological-response assays. The plasmid pMP15, which appends the prepro sequences of α-factor to the N-terminus of the receptor was also used in a subset of biological-response experiments. Finally, the plasmid pLPXt-FLU was used to append a hemagglutinin epitope to the C-terminus of the receptor. This final construct was utilized to verify MC4 receptor expression by Western blot analysis.

The melanocortin receptors have been demonstrated to interact with multiple ligands arising from the processing of pro-opiomelanocortin. All of these natural ligands are relatively small peptides. α-MSH is a 13 amino acid peptide acylated at the amino-terminus and amidated at the carboxyl-terminus. A synthetic analog of α-MSH with enhanced resistance to proteolysis is [Nle4, D-Phe7]-α-MSH (NDP-MSH). The lower potency agonists include β-MSH, which is 22 amino acids in length, and the family of γ-MSH peptides which vary in length from 11–27 amino acids (11 amino acid γ1, 12 amino acid γ2, and 27 amino acid γ3).

The MC4 receptor is well characterized as signaling through $G_{\alpha s}$. Therefore, upon confirmation of receptor expression by Western blot, the full-length MC4 receptor was introduced along with several $G_{\alpha s}$ expression plasmids, into a series of isogenic strains varying only in $G_\gamma$ chimera composition. Similarly, MC4 receptor expressed with the prepro-α-factor leader was introduced into one of the Gγ chimera strains with the series of $G_{\alpha s}$ expression plasmids.

Ligands were applied to cell monolayers, and receptor activation was examined by the FUS1-HIS3 growth assay. Upon ligand addition, the unmodified receptor proved to be most active in CY9800. Only two ligands however, were capable of receptor stimulation, α-MSH and NDP-MSH. In contrast, when α-factor prepro leader sequences were appended to the N-terminus of the receptor all ligands activated the receptor in the sole strain assayed, CY9438. Quantitation of ligand-dependent activation of the yeast mating pathway was measured through induction of FUS1-

EXAMPLE 10

Yeast Expression of the Rat Metabotropic Glutamate Receptor 2(mGluR2)

Metabotropic glutamate receptors, in contrast to other seven transmembrane receptors, possess the unusually long first extracellular domains. Specifically, the N-terminal domain of rat mGluR2 consists of 567 amino acid residues.

The rat mGlu2 receptor cDNA was sequenced and found to be identical to that in the published literature (GenBank accession number D16817). Thereafter, the cDNA was subcloned into eight yeast expression vectors.

The plasmid pLPXt was modified for expression of the mGlu2 receptor from the PGK promoter. Transcription of receptors in this vector is normally terminated approximately 400 nucleotides 3' from the end of the cDNA insert. Increasing evidence however, suggested that it might be possible to increase the steady state level of transcript by including a transcriptional terminator adjacent to the carboxyl-terminus of the cDNA. Thus pLPXt was modified by the addition of a transcriptional terminator from the PHO5 gene. This construct is referred to as mGlu2. Two constructs were also prepared using the previously described prepro-α-factor leader. In the construct designated ppαF-mGluR2, the leader sequences were inserted adjacent to the N-terminus of the receptor. In contrast, the postulated signal sequence of the mGlu2 receptor was deleted, and replaced by the prepro-αfactor leader in the construct ppαF-mGluR2Δ. Finally, the construct invmGluR2 directs synthesis of the mGlu2 receptor with the leader of the invertase protein appended to the N-terminus of the receptor. Like the α-factor leader, this leader has also been demonstrated to promote entrance of heterologous proteins into the secretory pathway of yeast. These four constructs were used to investigate the biological activity of the mGlu2 receptor in yeast. In order to evaluate expression by Western blot, the mGlu2 receptor was also cloned into a set of vectors identical to those just described, but with the hemagglutinin epitope attached to the carboxyl-terminus of the protein.

Plasmids expressing hemmaglutinin-tagged receptors were transfected into yeast, and receptor levels were determined by Western blot analysis of total membrane protein preparations. In the absence of yeast leader sequences no receptor was detected, even with prolonged exposure of the nitrocellulose membrane. In contrast, when expressed with the prepro-α factor or invertase leader, dark doublet bands of high molecular weight were detected. These results indicated that receptor expression could be dependent upon the presence of yeast sequences.

There was however, an alternative interpretation. Large, highly glycosylated proteins transfer to nitrocellulose with low efficiency. Therefore, it was a formal possibility that receptor lacking a yeast leader was hyper-glycosylated, rendering it resistant to detection by Western blot. To address this possibility, protein samples were treated with Endoglycosidase H (Endo H), which cleaves the high mannose structures on N-linked oligosaccharides. Removal of oligosasccharides did not improve visualization of the leader receptor, suggesting that in the vector, the mGlu2R was not synthesized. Furthermore, the Endo H results indicated the presence of oligosaccharides on receptor made form constructs with leaders, once again indicating transport into the secretory pathway. Together, these data underscore the important role yeast leader sequences play in mGlu2 receptor expression.

Several agonists are available for research on the mGlu2 receptor. The agonists used in these studies included L-CCG-I, 1S,3R-ACPD, and L-glutamic acid, with $EC_{50}$ values of 0.75 µM, 7.7 µM and 11.8 µM, respectively. Stimulation of the mGlu2 receptor has been demonstrated to promote inhibition of adenylyl cyclase, thus initial attempts to couple the receptor focused primarily upon the use of proteins from the $G_{\alpha i}$ family.

CY9437 expresses a unique Ste18-Gγ2 chimera. To date, most receptors that have been developed into successful assays have shown the ligand independent receptor activation, LIRMA, phenotype in this strain when presented with an appropriate $G_\alpha$ subunit. Therefore in the absence of receptor coupling, CY9437 can be loosely used as a diagnostic indicator of the capacity of a receptor to couple in yeast. When compared with other mGlu2 receptor constructs, only ppαF-mGluR2Δ induced LIRMA. However, it is possible that rather than LIRMA, this is actually ligand-dependent activation arising from glutamate released into the growth media by the yeast. Glutamate oxidase, which converts glutamate to α-ketoglutarate, was used in an attempt to diminish glutamate levels. Nonetheless, additional glutamate metabolizing enzymes (which may be more potent under yeast growth conditions) are available including L-glutamate dacarboxylase and L-glutamate dehydrogenase.

β-galactosidase in a non-optimized microtitre format. In this assay, maximal stimulation was roughly 5-fold with an $EC_{50}$ of approximately 12 nM.

---

What is claimed is:

1. A yeast cell comprising:
   (i) a heterologous G protein coupled receptor; and
   (ii) a non-naturally occurring G protein subunit, wherein the G protein subunit is a mammalian Gα protein subunit comprising a mutation selected from the group consisting of: human Gα16(S270P); rat Gαs(D229S); rat Gαs(D229V); rat Gαs(N254D); rat Gαs(S286P); rat Gαs(E10K); mouse Gαi2-GαoB(S280P); human Gαl2(Q229L); human Gαl2(G228A); and human Gαi2(S288P);

such that expression of said non-naturally occurring G protein subunit functionally integrates said heterologous G protein coupled receptor into the yeast cell pheromone signaling pathway.

2. The yeast cell of claim 1, wherein said non-naturally occurring G protein subunit is a yeast-mammalian G protein subunit chimera comprising a first polypeptide from a yeast G protein subunit and a second polypeptide from a mutant mammalian G protein subunit.

3. The yeast cell of claim 2, wherein said second polypeptide comprises a mammalian Gα subunit comprising a mutation selected from the group consisting of: human Gα16(S270P); rat Gαs(D229S); rat Gαs(D229V); rat Gαs(N254D); rat Gαs(S286P); rat Gαs(E10K); mouse Gαi2-GαoB(S280P); human Gα12(Q229L); human Gα12(G228A); and human Gαi2(S288P).

4. The yeast cell of claim 1, further comprising an indicator gene that produces a detectable signal upon functional coupling of the heterologous G protein coupled receptor to the G protein.

* * * * *